United States Patent [19]
Keller

[11] Patent Number: 5,356,796
[45] Date of Patent: Oct. 18, 1994

[54] **REPRESSOR PROTEIN AND OPERON FOR REGULATING EXPRESSION OF POLYPEPTIDES AND ITS USE IN THE PREPARATION OF 2,2-DIALKYGLYCINE DECARBOXYLASE OF *PSEUDOMONAS CEPACIA***

[75] Inventor: John W. Keller, Fairbanks, Ak.

[73] Assignee: The University of Alaska, Fairbanks, Ak.

[21] Appl. No.: 952,817

[22] Filed: Sep. 28, 1992

Related U.S. Application Data

[63] Continuation-in-part of Ser. No. 501,814, Mar. 30, 1990, Pat. No. 5,210,025.

[51] Int. Cl.$^5$ .................. C12N 15/31; C12N 15/63; C12N 15/67; C12N 15/70
[52] U.S. Cl. .................. 435/69.1; 435/232; 435/252.3; 435/252.33; 435/320.1; 530/358; 536/23.7; 536/24.1; 935/11; 935/29; 935/33; 935/40; 935/43; 935/68; 935/72; 935/73
[58] Field of Search ................. 435/69.1, 232, 252.3, 435/252.33, 320.1; 530/358; 536/237, 24.1

[56] References Cited

U.S. PATENT DOCUMENTS 5,210,025  5/1993  Keller .................. 435/69.1

OTHER PUBLICATIONS

Keller, J. Biol. Chem., 265:5531–5539 (1990).
Sato et al., Agricultural & Biol. Chem. (Tokyo), 42:2341–2346 (1978).
Aaslested et al., J. Bacteriol., 88:1296–1303 (1964).
Keller et al., FASEB J., 2(5), (Abstr. 6111) (1988).
Keller et al., J. Cell Biol., 107:399A, (Abstr. 2276) (1988).
Keller, J. W. et al., 1990, FASEB Journal, 4():A2318, Abstract 3612.
Toney, M. D., et al., 1991, Journal of Molecular Biology, 222(4):873–875.
Keller, J. W., et al., 1992, FASEB Journal, 6(1):A356, Abstract 2048.
Maxon, M. E., et al., 1989, Proceedings of the National Academy of Sciences, USA, 86(1):85–89.
Neidle, E. L., et al., 1989, Journal of Bacteriology, 171(10):5410–5421.
Bading, H., 1988, Nucleic Acids Research, 16(12):5241–5248.
Mizusawa, S., et al., 1986, Nucleic Acids Research, 14(3):1319–1324.
Corpet, F., 1988, Nucleic Acids Research, 16(22):10881–10890.
Oehler, S., et al., 1990, The EMBO Journal, 9(4):973–979.
Honoré, N., et al., 1986, The EMBO Journal, 5(13):3709–3714.

*Primary Examiner*—Robert A. Wax
*Assistant Examiner*—William W. Moore
*Attorney, Agent, or Firm*—Finnegan, Henderson, Farabow, Garrett & Dunner

[57] ABSTRACT

A nucleotide sequence coding for a repressor protein for regulating gene expression that comprises about a 687 bp nucleotide region beginning about 81 bases upstream from the 2,2-dialkylglycine decarboxylase structural gene shown in FIG. 3. The repressor protein comprises about 229 amino acids. The nucleotide sequence is useful for regulating gene expression in recombinant expression vectors. The vectors and *E. coli* cells transformed with the vectors are useful for preparing *Pseudomonas cepacia* 2,2-dialkylglycine decarboxylase.

40 Claims, 18 Drawing Sheets

```
1331  TCCATCAAAACAGACGGCGCCTAGACTGCAAGCGATCCCTGCCCCTTGCCGGAGAAGCCCGATGTCC
                                                                     MetSer>    2

1401  CTGAACGACGATGCAACCTTCTGGGCGCAACGCCAGGCAGCACCTGGTCCGCTACGGGCACGTTCGAGC
      LeuAsnAspAspAlaThrPheTrpAlaThrAlaArgGlnHisLeuValArgIlyGlyThrPheGlu>     25

1471  CGATGATCATCGAGCGGCGAAGGGCAGCTTCGTCTATGACGGCCGACGGCCGCGATCCTCGATTCAC
      ProMetIleIleGluArgArgLysGlySerPheValTyrAspAlaAspGlyArgAlaIleLeuAspPheThr>   49

1541  GTCGGGGAGATGAGCGGCGGTGCTCGGGCACTGCCATCCGGAGATCTCCGTCATCGGAATACGCG
      SerGlyGluMetSerAlaValLeuGlyHisCysHisProGluIleValSerValIleGlyGluTyrAla>    72

1611  GGCAAGCTCGATCACCTGTTCAGCGGAATCGTGTCGCGGCCCGTCTGCGACCTGCGACGCGCCTGCCA
      GlyLysLeuAspHisLeuPheSerGlyIleValSerArgProValAspLeuAlaThrArgLeuAla>    95

1681  ACATCACGCCGCCCGGGCTCGACCGGCCTGCTCAGCACCGGCGGAATGAACGAAGCGGCAAT
      AsnIleThrProProGlyLeuAspArgLeuLeuLeuSerThrGlyAlaGluSerAsnGluAlaAlaIle>   119

1751  CCGGATGGCGAAGCTCGTCACCGGCAAGTACGAGATCTGTCGGCTTCGGCAGTCGTGGCACGGGATGACG
      ArgMetAlaLysLeuValThrGlyLysTyrGluIleValGlyPheAlaGlnSerTrpHisGlyMetThr>  142

1821  GGCGGGCCCGATCGGCTACAGAGCCGGGCGCAAGGGTGTCGGCGTGCCCGCCGTCGGCTCGTTCG
      GlyAlaAlaAlaSerAlaThrTyrSerAlaGlyArgLysGlyValGlyProAlaAlaValGlySerPhe>  165

1891  CGATTCCGGCGCCCATTCAGCTGCTGAGCCAACGGGCGTACATATATCGACTATCGCCGAACT
      AlaIleProAlaProPheThrTyrArgProAlaArgAsnGlyAlaTyrLeuAlaGluLeu>   189

1961  CGACTACGCGTTCGACGCTGATCGAACTGCCGGAGCTCGAGCGGCCAACCTCGGCATTCATCCGGAGCCGATC
      AspTyrAlaPheAspLeuIleAspArgGlnSerSerGlyAsnLeuAlaAlaPheIleAlaGluProIle>   212

2031  CTCAGTTCGGGCGGGAATCATCGAACTGCCGGACGGCTACATGGCGGCGCTCAAGGCGCTCAAGGCGAAGTGCGAGGCGC
      LeuSerSerGlyIleGlyIleGluLeuProAspGlyTyrMetAlaAlaLeuLysArgLysCysGluAla>  235

2101  GCGGGATGCTGCTGATCCTCGACGAGGCCAGAGCGGCTGAGACAGATCACCGGGTGTAGTTCGCGTGCCA
      ArgGlyMetLeuLeuIleLeuAspGluAlaGlnThrGlyValGlyArgThrGlyMetPheAlaCysGln>   259

2171  GCGCGACGGCGTGACGCCGACATCCTGACGCTGTCGAAAACGCTCGGCGCCCGGCTGCCGCTCGCGGCC
      ArgAspGlyValThrProAspIleLeuThrLeuSerLysThrLeuGlyAlaGlyLeuProLeuAlaAla>  282

2241  ATCGTGACGTCCGGCGATGAGGACGGGAACGCGCGAACTCGGCTGCTTCTATACGACGCACGTGT
      IleValThrSerAlaAlaIleGluGluArgAlaHisGluLeuGlyLeuGlyTyrLeuPheTyrThrThrHisVal>   305
```

```
1410 AGGTTGCATCGTCGTTCAGGGACATCGGGCTTCTCCGGGCAAGGGGGCAGGGATCGCTTG

1350 CAGTCTAGGCGCGCGTCTGTTTTGATGGAAACGAATAGTTCTTATGCAAGGTAGAAAGGG
                                        M  Q  G  R  K  G        5

1290 GGCTAATACCTTGGGACGCTCGCTCGAAATCGACCTGCTGCGTTCGTTCGTCGTGATCGC
      A  N  T  L  G  R  S  L  E  I  D  L  L  R  S  F  V  V  I  A  25

1230 CGAGGTGCGCGCGCTCAGCGCGGCCGCGCGCGTCGGCCGGACGCAGTCCGCGCTCAGCCA
      E  V  R  A  L  S  A  A  A  A  R  V  G  R  T  Q  S  A  L  S  Q  45

1170 GCAGATGAAGCGGCTCGAGGATATCGTCGACCAGCCGCTGTTCCAGCGCACCGGCCGCGG
      Q  M  K  R  L  E  D  I  V  D  Q  P  L  F  Q  R  T  G  R  G  65

1110 CGTGGTGCTGACGCACCCCGGCGAGCGGCTGCTCGTGCATGCGCAGCGCATCCTGCGGCA
      V  V  L  T  H  P  G  E  R  L  L  V  H  A  Q  R  I  L  R  Q  85

1050 GCACGACGAGGCAATGGCCGACCTGTGCGGCACGGGGTTGACGGGGACGATCCGGTTCGG
      H  D  E  A  M  A  D  L  C  G  T  G  L  T  G  T  I  R  F  G  105

990 GTGCCCGGACGATTACGCGGAGGTGTTTCTGCCGCCGCTGCTGCGGCAGTTTTCGAGCCA
      C  P  D  D  Y  A  E  V  F  L  P  P  L  L  R  Q  F  S  S  Q  125

930 GCATCCGCAGGCGATCGTCGAAATCGTATGCGGGCCGACGCCGCGGCTGCTCGAACAGCT
      H  P  Q  A  I  V  E  I  V  C  G  P  T  P  R  L  L  E  Q  L  145

870 CGAGAAGCGCGCGGTCGATCTCGCGATGATTTCATTGCCGGACGATGGGGCGAACGACGA
      E  K  R  A  V  D  L  A  M  I  S  L  P  D  D  G  A  N  D  D  165

810 CATCATTCGTCGCGAGCAGCTGGTCTGGATCGGCTATCCGGGGCTGGAGCCCGCGCATTT
      I  I  R  R  E  Q  L  V  W  I  G  Y  P  G  L  E  P  A  H  F  185

750 CGATCCGCTGCCGCTCGCGCTGTCCGATCCCGATACGCTCGATCACATCGCGGCCTGCGA
      D  P  L  P  L  A  L  S  D  P  D  T  L  D  H  I  A  A  C  D  205

690 CGCGTTGCATCGCGCCGGTCGCGATTACCGCGTCGCGTATGCGAGCAGCAGTCTCGCGGG
      A  L  H  R  A  G  R  D  Y  R  V  A  Y  A  S  S  S  L  A  G  225

630 GCTGATCGCGCTGGTGCGCTCGGGGCAGGCGTTCGCGGTGATGACGCAGACGGCCGTGCC
      L  I  A  L  V  R  S  G  Q  A  F  A  V  M  T  Q  T  A  V  P  245

570 GGCCGACCTGGCGATCGTCAACGGCGATCCGCGGTTGCCGCCGTTGCCGGCGGTGGGCAT
      A  D  L  A  I  V  N  G  D  P  R  L  P  P  L  P  A  V  G  I  265

510 TACGCTGAAGTTCGACCGGAAACGGCCGTCGCATCTGACGGCGGCGTTCGCCGAGCATAT
      T  L  K  F  D  R  K  R  P  S  H  L  T  A  A  F  A  E  H  I  285

450 TCGGGCCGTGTTGCCGATGCTGTGACGCGAAGTCGTCGCGCCGGAAACGCAGGCATCGAC
      R  A  V  L  P  M  L                                         292

390 GCGGGATTCGAGGCGTCGACGTTTGCCGTCCATCTGACCGAGTGCTTCGTTCCGCATCGC
 330 CGAAGCAATAAAAAAACCCGCGAAGCCATGCGCTGTCGCGGGTTTTGCAAATGCACGAAA
 270 CACGGAAAAACCGTATTTGGTGCCGACGGCGAGACTCGAACTCGCACAGCTTTCGCCACT
 210 ACCCCCTCAAGATAGCGTGTCTACCAATTTCACCACGTCGGCACTGCAAGGGGCCGAATT
 150 GTAGCGTTACCATCGCGCGTTTGTGAAGAGGGTGTGACACGGCGAGCGGATGCGTGAAAG
  90 CGATCCCGGTAGAATTCGGACGATCGGTCCGACGACCATCGCTACTGCCATCCGCTTTCT
  30 CCCCGTGACCACCACCCTCGAACAACTGCAG*
```

FIG.4

```
MLSKLASLQTVAALRGLRTSVASATSVATKKTEQGPPSSEYIFERESKYGAHMYHPLPV                                  60
   ::: ::  : : :  :::                                   : :
MSLNDDATFWRNAQHLVRY----------GGTFEPMIIERAK--GSFVDADGR                                        43

ALERGKGIYMWDVEGRQYFDFLSAYGAVSQGHCHPKIIEAMKSGVDKITLTSRAFYNNVL                                 120
 :::  :: ::  :::::   ::: : :::::  :::  ::: : :  :    :
AILDFTSGEMSAVLGHCHPEIVSVIGEYA-GKLDHLFSGIVSRPMVDATRLANITPPGL                                  102

GEYEEYITKLFNYNKVIPMNTGVEAGETACKLARRMGYTVKGIQKYKAKIVFAVGNFWGR                                 180
::    :  :  ::  :    ::    :: :  ::  : ::  : :  ::  : ::
DRALLLSIGAESNEAALRMAKLMTIGKYEIVGFAQSM------HGMTGAAASATVSAGR-KGV                              157

TLSAVSSSTDPTSYDGFGPFMP----GFETIPYNDLP-ALERALQDPNVAAFMVEPIQGEA                                236
    :  ::  ::: ::   :    :  :: :: :: ::  :    ::  :  :::
GPAAVGSFAIBAPETYRPRER-NGAYDYLAELDYAFDLIDRQSSGNLAAFIAEPILSSG                                  216

GVIVPDPGYLTGVRELCTRHQVFIADEIQTGLARTGRWLAVDHENVRPDIVLGKALSG                                   296
 :  :::    ::  :: ::  :  :::  ::::: ::  : :  ::::::  ::
GIIELPDGYMAALKRKCEARGMLLILDEATGVGRTGTMFACQRDGMTPDILTLSKTLGA                                  276

GLYPVSAVLCDDDIMLTIKPGEHGSTYGGNPLG---CR----IATAAAEVIEEEHIAENADK                               351
::  : ::   :  ::   ::  ::::  :     :     :    ::: ::: :: : :
GL-PLAAIVTSAAI--EERAHELGYLFYTTHMSDRCPPAGVGLRVLDVVQRDGIVARANV                                 333

MGAILRKELMKIPS--DVMTAVRGKGLLNAIVIRETKDCDAWKVCRLR-DN---------                                 400
::  :: :: : :   :: : :::  :: :: ::: ::  ::: : :  :
MGDRLRRGLLDLMERFDCIIGDVRGRGLLLGVELIVKDRRTKEPADGLGAKITRECMNLGLS                               393

-GLLAKPTHGDIIRLAPPLVIKEDETRESVEIINKTILSF                                                    439
  :   :  :    :::::  ::: :: ::  :: : :
MNIVQLPGMGGMFRIAPPLIMSEDEIDLGLSLLGQAIERAL                                                   434
```

FIG. 9

| | | | * | | | |
|---|---|---|---|---|---|---|
| P. cepacia DGD[1] | V I P D I L T | - - - - | L S K T L G A G L | - - - | P L A A | - I V T |
| Mammalian OrnAT[2] | V R P D I V L | - - - - | L G K A L S G G L Y | - - - | P V S A | - V L C |
| Yeast OrnAT[3] | A K P D I V L | - - - - | L G K A L S G G V L | - - - | P V S C | - V L S |
| Chick. Mito. AspAT[4] | P G I D V V L | S Q S | Y A K N M | - G L Y G E R | A G A F | - I V C |
| Pig Cyto. AspAT[5] | E G F E L F C | A Q S | F S K N F | - G L Y N E R | V G N L T | V V A |
| Pig Mito. AspAT[6] | M H K E L I V | A S S | Y S K N F | - G L Y N E R | V G A C T | L V A |
| E. coli AspAT[7] | Q G I D I L | - Y S G S Q K | V L V A P P G I S L | I S F N D K A K |
| Rat Mito. SerAT[7] | Q E L A S F H S | V S K G F M G E C | - G F R |
| Pig Heart AlaAT[8] | | | | | | |

FIG.10

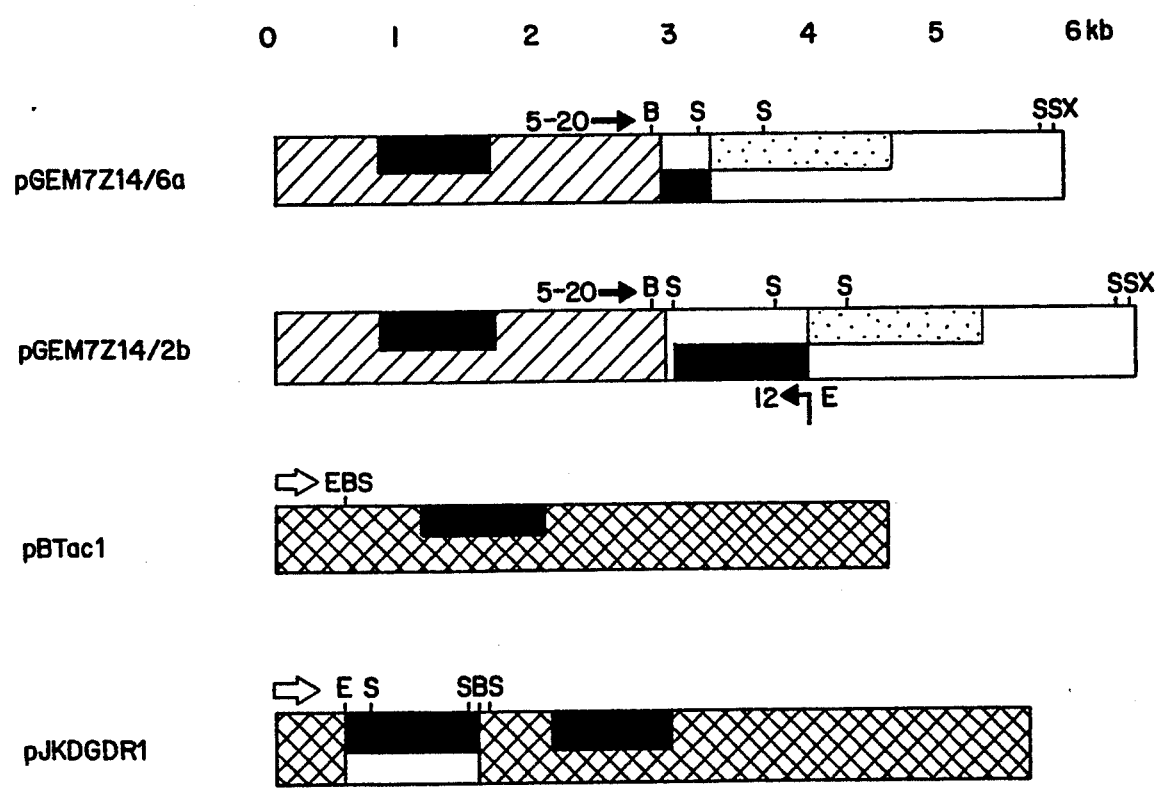
FIG. II

```
              10         20         30         40         50
DGDR    MQGRKGANTLGRSLEIDLLRSFVVLAEV.RALSAAARVGRTQSALSQQMKRLEDI
LYSR            MAAVNLRHIEIFHAVMTAGSLTEAAHLLHTSQPTVSRELARFEKV
CYSB             MKLQQLRYI..VEVVNHNLNVSSTAEGLYTSQPGISKQVRMLEDE
OXYR              MNIRDLEYLVALAKHRHFRRAADSCHVSQPTLSGQIRKLEDE
METR             MIEIKHLKTLQALRNSGSLAAAAAVLHQTQSALSHQFSDLEQR
CATM              MELRHLRYFVTVVEEQSISKAAEKLCIAQPPLSRQIQKLEEE 60         70         80         90        100        110
VDQPLFQRTGRGVV..LTHPGERLLVHAQRILRQHDEAMADLCGT..GLTGTIRFGCPDDYAEV
IGLKLFERVRGR.LHPTVQGLRLFEEVQRSWYGLDRIVSAAESLREFRQ.GELSIACLPVFSQS
LGIQIFSRSGKH.LTQVTPAGQEIIRIAREVLSKVDAIKSVAGEHTWPDKGSLYIATTHTQARY
LGVMLLERTSRK.VL.FTQAGMLLVDQARTVLREVKVLKEMASQQGETMSGPLHIGLIPTVGPY
LGFRLFVRKSQP..LRFTPQGEVLLQLANQVLPQI...SRALQACNEPQQTRLRIAIECHSCIQ
LGIQLFERGFRP..AKVTEAGMFFYQHAVQILT.HTAQASSMAKRIATVSQTLRIGYVSSLLYG 120        130        140        150        160        170        180
FLPPLLRQFSSQHPQAIVEIVCGPTPRLLEQLEKRAVDLAMISLPDDGANDDIIRREQLVWIGY
FLPQLLQPFLARYPDVSLNIVPQESPLLEEWLSAQRHDLGL..TETLHTPAGTERTELLSLDEVC
ALPNVIKGEIERYPRVSLHMHQGSPTQIADAVSKGNADFAIATEALHLYEDLVMLPCYHWNRAI
LLPHIIPMLHQTFPKLEMYLHEAQTHQLLAQLDSGKLDCVILALVKES.ERFIEVPLFDEPMLL
WLTPALENFRASWPQVEMDFTSGVTFDPQPALQQGELDLVMTSDILPRSE.LHYSPMFDFEVRL
LLPEITYLFRQQNPEIHIELIECGTKDQINALKQGKIDLGFGRLKITDPAIRRIVLHKEQLKLA 190        200        210        220        230        240
PGLEPAHFDPLPLALSDPDTLDHIAACDALHRAGRDYRVAYASSSLAGLIALVRSGQAFAVMTQ
VLPPGH.PLAVKKVLTPDDFQGENYISLSRTDSYR.QLLDQLFTEHQVKRRMIVETHSA.ASVC
VVTPDH.PLAGKKAITIEELAQYPLVTYTFGFTGR.SELDTAFNRAGLTPRIVFTATDA.DVIK
AIYEDH.PWANRECVPMADLAGEKLLMLEDGHCLR.DQAMGFCFEAGADEDTHFRATSL.ETLR
VLAPDH.PLASKTQITPEDLASETLLIYPVQRSRL.DVWRHFLQPAGISPLLKSVDNTL..LLI
IHKHHHLNQFAATGVHLSQIIDEPMLLYPVSQKPNFATFIQSLFTELGLVPSKLTEIREIQLAL 250        260        270        280        290
TAVPADLAIVNGDPRLPPLPAVGITL..KFDRKRPSHLTAAFAEHIRAVLPML
AMVRAGVGISVVNPLTALDYAASGLV....VRRFSIAVPFTVSLIRP..LHRPSSALVQAFS..
TYVRLGLGVGVIASMAVDPVADPDLVR.VDAHDIFSHSTTKIGFRRSTFLRSYMYDFIQRFA..
NMVAAGSGITLLPALAVPPERKRDGVVYPCIKPEPRRTIGLVYRPGSPLRSRYEQLAEAIRA..
QMVAARMGIAALPHWVVESVERQGLVVLTKTLGDGLWSRLYAAVRDATSVRR
GLVAAGEGVCIVPASAWILG
```

FIG. 12

```
5' - CGCGCTGCTGCTCAGCACCGGCGCG - 3'
3' - GCGCGACGACGAGTCGTGGCCGCGC - 5'     O1

5' - GCCGAGGTGCGCGCGCTCAGCGCGGC - 3'
3' - CGGCTCCACGCGCGCGAGTCGCGCCG - 5'    O2
```

FIG. 17

SEQUENCE LISTING ( 1 ) GENERAL INFORMATION:

( i i i ) NUMBER OF SEQUENCES: 30

( 2 ) INFORMATION FOR SEQ ID NO:1:

( i ) SEQUENCE CHARACTERISTICS:
   ( A ) LENGTH: 20 base pairs
   ( B ) TYPE: nucleic acid
   ( C ) STRANDEDNESS: single
   ( D ) TOPOLOGY: linear ( i i ) MOLECULE TYPE: other
   ( A ) DESCRIPTION: synthetic DNA ( x i ) SEQUENCE DESCRIPTION: SEQ ID NO:1:

GCTGCAAGGC GATTAAGTTG                                                                                          20

( 2 ) INFORMATION FOR SEQ ID NO:2:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: other
      ( A ) DESCRIPTION: synthetic DNA ( x i ) SEQUENCE DESCRIPTION: SEQ ID NO:2:

AGCTCTCCGG ATCCAACCTT                                                                                          20

( 2 ) INFORMATION FOR SEQ ID NO:3:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: other
      ( A ) DESCRIPTION: synthetic DNA ( x i ) SEQUENCE DESCRIPTION: SEQ ID NO:3:

ATTTCACACA GGAAACAGCT                                                                                          20

( 2 ) INFORMATION FOR SEQ ID NO:4:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: other
      ( A ) DESCRIPTION: synthetic DNA ( x i ) SEQUENCE DESCRIPTION: SEQ ID NO:4:

AGCTCTCCGG ATCCAAGCTT                                                                                          20

( 2 ) INFORMATION FOR SEQ ID NO:5:

( i ) SEQUENCE CHARACTERISTICS:
      ( A ) LENGTH: 33 base pairs
      ( B ) TYPE: nucleic acid
      ( C ) STRANDEDNESS: single
      ( D ) TOPOLOGY: linear ( i i ) MOLECULE TYPE: other
      ( A ) DESCRIPTION: synthetic DNA ( x i ) SEQUENCE DESCRIPTION: SEQ ID NO:5:

CCACAGAATT CTATGCAAGG TAGAAAGGGC GCT                                                                            33

( 2 ) INFORMATION FOR SEQ ID NO:6:

( i ) SEQUENCE CHARACTERISTICS:

(A) LENGTH: 18 base pairs
(B) TYPE: nucleic acid
(C) STRANDEDNESS: single
(D) TOPOLOGY: linear (ii) MOLECULE TYPE: other
(A) DESCRIPTION: synthetic DNA (xi) SEQUENCE DESCRIPTION: SEQ ID NO:6:

TTGCCGCTTC GTTCGATT                                                                           18

(2) INFORMATION FOR SEQ ID NO:7:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: other
(A) DESCRIPTION: synthetic DNA (xi) SEQUENCE DESCRIPTION: SEQ ID NO:7:

ATGTCCCTGA ACGACGATGC                                                                         20

(2) INFORMATION FOR SEQ ID NO:8:

(i) SEQUENCE CHARACTERISTICS:
(A) LENGTH: 2639 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:8:

| | | | | | | |
|---|---|---|---|---|---|---|
| TCCATCAAAA | CAGACGCGCG | CCTAGACTGC | AAGCGATCCC | TGCCCCCTTG | CCCGGAGAAG | 60 |
| CCCGATGTCC | CTGAACGACG | ATGCAACCTT | CTGGCGCAAC | GCCAGGCAGC | ACCTGGTCCG | 120 |
| CTACGGCGGC | ACGTTCGAGC | CGATGATCAT | CGAGCGCGCG | AAGGGCAGCT | TCGTCTATGA | 180 |
| CGCCGACGGC | CGCGCGATCC | TCGATTTCAC | GTCGGGCGAG | ATGAGCGCGG | TGCTCGGCCA | 240 |
| CTGCCATCCG | GAGATCGTCT | CCGTCATCGG | CGAATACGCG | GGCAAGCTCG | ATCACCTGTT | 300 |
| CAGCGGAATC | GTGTCGCGGC | CCGTCGTCGA | CCTCGCGACG | CGCCTCGCCA | ACATCACGCC | 360 |
| GCCCGGGCTC | GACCGCGCGC | TGCTGCTCAG | CACCGGCGCG | GAATCGAACG | AAGCGGCAAT | 420 |
| CCGGATGGCG | AAGCTCGTCA | CCGGCAAGTA | CGAGATCGTC | GGCTTCGCGC | AGTCGTGGCA | 480 |
| CGGGATGACG | GGCGCGGCCG | CATCGGCCAC | GTACAGCGCG | GGCCGCAAGG | GTGTCGGCCC | 540 |
| GGCCGCCGTC | GGCTCGTTCG | CGATTCCGGC | GCCATTCACG | TACCGGCCGC | GCTTCGAGCG | 600 |
| CAACGGCGCG | TACGACTATC | TCGCCGAACT | CGACTACGCG | TTCGACCTGA | TCGACCGCCA | 660 |
| GTCGAGCGGC | AACCTCGCGG | CATTCATCGC | GGAGCCGATC | CTCAGTTCGG | GCGGGATCAT | 720 |
| CGAACTGCCG | GACGGCTACA | TGGCGGCGCT | CAAGCGCAAG | TGCGAGGCGC | GCGGGATGCT | 780 |
| GCTGATCCTC | GACGAGGCGC | AGACGGGCGT | CGGACGCACC | GGCACGATGT | TCGCGTGCCA | 840 |
| GCGCGACGGC | GTGACGCCCG | ACATCCTGAC | GCTGTCGAAA | ACGCTCGGCG | CCGGGCTGCC | 900 |
| GCTCGCGGCC | ATCGTGACGT | CCGCGGCGAT | CGAGGAACGC | GCGCACGAAC | TCGGCTACCT | 960 |
| GTTCTATACG | ACGCACGTGT | CCGATCGCTG | CCCCCCGGCC | GGCGTCGGCC | TGCGCGTGCT | 1020 |
| CGACGTGGTG | CAGCGCGACG | GGCTCGTCGC | ACGCGCGAAC | GTGATGGGCG | ACCGGCTCAG | 1080 |
| GCGCGGCCTG | CTCGACCTGA | TGGAGCGGTT | CGACTGCATC | GGCGACGTGC | GCGGGCGCGG | 1140 |
| GCTGCTGCTC | GGCGTCGAGA | TCGTCAAGGA | TCGACGCACG | AAAGAGCCGG | CGGACGGCCT | 1200 |
| CGGCGCGAAG | ATCACGCGCG | AGTGCATGAA | CCTCGGGCTC | AGCATGAACA | TCGTGCAGTT | 1260 |

```
GCCCGGCATG GGCGGCGTGT TCCGGATCGC GCCGCCGCTG ACGGTCAGCG AGGACGAGAT    1320
CGATCTCGGC TTGTCGCTGC TCGGTCAGGC GATCGAACGC GCGCTGTAAC GCCGCCGCCC    1380
GGTAACGCCC TTCTCCGCAT CGTGCGATTC GTCGCGCCGG TTCGAGCGAC CGGCGCGACG    1440
GATTCCCGAT CGATCAGCGC GTTTCGGCCG CCCACGCTTC GGCATCGGCA CCGGCCGGAA    1500
TGCGCATCGG GCTCGACGGG TCCGTCGCCG CGCGCCACAC GGCGTCGGCA ACATCCTGCG    1560
CACGGGTGAT CGGCCCCGAC GCATCGAGCA TCCTCGCGAC GGCCTTTCCG GCGAACTCCG    1620
CATAAGCCTC GTGTTCGAAG CCATGCATGT GCGCACGCGC GTTGTCGCCG AAACGCGTGT    1680
CCGGGTGCAC GGCCCGGCAG CACGAGATGC GCGCGCACGC CGAACGGTTC GAGTTCGACC    1740
GCCATCGATT CGGTGAACGC ATTGACCGCC GCCTTGCTGG CCCGGTATGC GCCGACCAGC    1800
GGCAACACCT TCAGCGTGAC GCTCGACGTG ACGTTCACGA TCACGCCGGC CCCACGCCGG    1860
CGAAACTGCG GCAGCACGGC CCTGCGTCAC CGCAATCGTG CCGATCGTGT TGGTTTCGAA    1920
CAGCGCACGC ACCGTGTCGA GCGGCGTGAG CTCGGCCGGC GCGGCCGCGC CGAAGCCTGC    1980
GTTATTGACG AGCACGTCGA TCGGGCCGGC CGCGTCGATG GCGGCGCGGA TGCTGTCCGT    2040
GTTCGTCACG TCGAGCGCCA GCACGCGCAG GCGTTCCGAT GGCGGCAGCA CGTCCTCGCG    2100
CGGTGTGCGA TCGTCGCGAC GACCTGCCAG TCGCGGGCCA GGAAATGGCG GCAATCTCG     2160
AGGCCGAAGC CGGAGGAACA GCCGGTGATC AGTACGGTCT TCATGCGAAC TCCTGGGATG    2220
TGTTGGGCAT GTGTCCGTAC GATAGATGGC CGGACCCGTA TTCGCTACAA TCGAAAATCC    2280
GATTTTCTTT TGCGAGAGTC CGGCGATGAT CGACCCGTTG ACCGAAGTCG TGACGCTGCT    2340
GCAACCAGGC GCGCGGTACT CCAAGTCGGT TCACGGCGCG CGCGTGGTCG ATCAACCAGC    2400
CGTTCTATTG CGCGATCCTC AAAGCGGGTG CCGGATCGCC ATCGACGGGA CACGCGCCGA    2460
TCGAGCTGCT GCCCGGCGAT TTCGTGCTGA TTCCGGCGGC CTACGGCGTC GCGATGTCCA    2520
GCCTCGAACC GCCGCCGCCG GGCGTCGAAA CAGGGCCGCC GGTCGCACTC GACAACGGCG    2580
AATACCGGAT CGGCGATCGG GCAACCCGTC GACACGCGGA TGATGGCCGG CAACTGCAG    2639
```

( 2 ) INFORMATION FOR SEQ ID NO:9:

( i ) SEQUENCE CHARACTERISTICS:
        ( A ) LENGTH: 434 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

```
Met Ser Leu Asn Asp Asp Ala Thr Phe Trp Arg Asn Ala Arg Gln His
  1               5                  10                  15

Leu Val Arg Tyr Gly Gly Thr Phe Glu Pro Met Ile Ile Glu Arg Ala
             20                  25                  30

Lys Gly Ser Phe Val Tyr Asp Ala Asp Gly Arg Ala Ile Leu Asp Phe
         35                  40                  45

Thr Ser Gly Glu Met Ser Ala Val Leu Gly His Cys His Pro Glu Ile
     50                  55                  60

Val Ser Val Ile Gly Glu Tyr Ala Gly Lys Leu Asp His Leu Phe Ser
 65                  70                  75                  80

Gly Ile Val Ser Arg Pro Val Val Asp Leu Ala Thr Arg Leu Ala Asn
                 85                  90                  95

Ile Thr Pro Pro Gly Leu Asp Arg Ala Leu Leu Leu Ser Thr Gly Ala
            100                 105                 110

Glu Ser Asn Glu Ala Ala Ile Arg Met Ala Lys Leu Val Thr Gly Lys
        115                 120                 125
```

| | | | | | | | | | | | | | |
|---|---|---|---|---|---|---|---|---|---|---|---|---|---|
|Tyr|Glu|Ile|Val|Gly|Phe|Ala|Gln|Ser|Trp|His|Gly|Met|Thr|Gly|Ala|
| |130| | | | |135| | | | |140| | | |
|Ala|Ala|Ser|Ala|Thr|Tyr|Ser|Ala|Gly|Arg|Lys|Gly|Val|Gly|Pro|Ala|
|145| | | | |150| | | | |155| | | | |160|
|Ala|Val|Gly|Ser|Phe|Ala|Ile|Pro|Ala|Pro|Phe|Thr|Tyr|Arg|Pro|Arg|
| | | | |165| | | | |170| | | | |175| |
|Phe|Glu|Arg|Asn|Gly|Ala|Tyr|Asp|Tyr|Leu|Ala|Glu|Leu|Asp|Tyr|Ala|
| | | |180| | | | |185| | | | |190| | |
|Phe|Asp|Leu|Ile|Asp|Arg|Gln|Ser|Ser|Gly|Asn|Leu|Ala|Ala|Phe|Ile|
| | |195| | | | |200| | | | |205| | | |
|Ala|Glu|Pro|Ile|Leu|Ser|Ser|Gly|Gly|Ile|Ile|Glu|Leu|Pro|Asp|Gly|
| |210| | | | |215| | | | |220| | | | |
|Tyr|Met|Ala|Ala|Leu|Lys|Arg|Lys|Cys|Glu|Ala|Arg|Gly|Met|Leu|Leu|
|225| | | | |230| | | | |235| | | | |240|
|Ile|Leu|Asp|Glu|Ala|Gln|Thr|Gly|Val|Gly|Arg|Thr|Gly|Thr|Met|Phe|
| | | | |245| | | | |250| | | | |255| |
|Ala|Cys|Gln|Arg|Asp|Gly|Val|Thr|Pro|Asp|Ile|Leu|Thr|Leu|Ser|Lys|
| | | |260| | | | |265| | | | |270| | |
|Thr|Leu|Gly|Ala|Gly|Leu|Pro|Leu|Ala|Ala|Ile|Val|Thr|Ser|Ala|Ala|
| | |275| | | | |280| | | | |285| | | |
|Ile|Glu|Glu|Arg|Ala|His|Glu|Leu|Gly|Tyr|Leu|Phe|Tyr|Thr|Thr|His|
| |290| | | | |295| | | | |300| | | | |
|Val|Ser|Asp|Arg|Cys|Pro|Pro|Ala|Gly|Val|Gly|Leu|Arg|Val|Leu|Asp|
|305| | | | |310| | | | |315| | | | |320|
|Val|Val|Gln|Arg|Asp|Gly|Leu|Val|Ala|Arg|Ala|Asn|Val|Met|Gly|Asp|
| | | |325| | | | |330| | | | |335| | |
|Arg|Leu|Arg|Arg|Gly|Leu|Leu|Asp|Leu|Met|Glu|Arg|Phe|Asp|Cys|Ile|
| | | |340| | | | |345| | | | |350| | |
|Gly|Asp|Val|Arg|Gly|Arg|Gly|Leu|Leu|Leu|Gly|Val|Glu|Ile|Val|Lys|
| | |355| | | | |360| | | | |365| | | |
|Asp|Arg|Arg|Thr|Lys|Glu|Pro|Ala|Asp|Gly|Leu|Gly|Ala|Lys|Ile|Thr|
| |370| | | | |375| | | | |380| | | | |
|Arg|Glu|Cys|Met|Asn|Leu|Gly|Leu|Ser|Met|Asn|Ile|Val|Gln|Leu|Pro|
|385| | | | |390| | | | |395| | | | |400|
|Gly|Met|Gly|Gly|Val|Phe|Arg|Ile|Ala|Pro|Pro|Leu|Thr|Val|Ser|Glu|
| | | | |405| | | | |410| | | | |415| |
|Asp|Glu|Ile|Asp|Leu|Gly|Leu|Ser|Leu|Leu|Gly|Gln|Ala|Ile|Glu|Arg|
| | | |420| | | | |425| | | | |430| | |
|Ala|Leu| | | | | | | | | | | | | | |

( 2 ) INFORMATION FOR SEQ ID NO:10:

( i ) SEQUENCE CHARACTERISTICS:
        ( A ) LENGTH: 1411 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:10:

```
AGGTTGCATC GTCGTTCAGG GACATCGGGC TTCTCCGGGC AAGGGGGCAG GGATCGCTTG      60
CAGTCTAGGC GCGCGTCTGT TTTGATGGAA ACGAATAGTT CTTATGCAAG GTAGAAAGGG     120
GGCTAATACC TTGGGACGCT CGCTCGAAAT CGACCTGCTG CGTTCGTTCG TCGTGATCGC     180
CGAGGTGCGC GCGCTCAGCG CGGCCGCGCG CGTCGGCCGG ACGCAGTCCG CGCTCAGCCA     240
GCAGATGAAG CGGCTCGAGG ATATCGTCGA CCAGCCGCTG TTCCAGCGCA CCGGCCGCGG     300
```

-continued

| | | | | | |
|---|---|---|---|---|---|
| CGTGGTGCTG | ACGCACCCCG | GCGAGCGGCT | GCTCGTGCAT | GCGCAGCGCA | TCCTGCGGCA | 360 |
| GCACGACGAG | GCAATGGCCG | ACCTGTGCGG | CACGGGGTTG | ACGGGGACGA | TCCGGTTCGG | 420 |
| GTGCCCGGAC | GATTACGCGG | AGGTGTTTCT | GCCGCCGCTG | CTGCGGCAGT | TTTCGAGCCA | 480 |
| GCATCCGCAG | GCGATCGTCG | AAATCGTATG | CGGGCCGACG | CCGCGGCTGC | TCGAACAGCT | 540 |
| CGAGAAGCGC | GCGGTCGATC | TCGCGATGAT | TTCATTGCCG | GACGATGGGG | CGAACGACGA | 600 |
| CATCATTCGT | CGCGAGCAGC | TGGTCTGGAT | CGGCTATCCG | GGCTGGAGC | CCGCGCATTT | 660 |
| CGATCCGCTG | CCGCTCGCGC | TGTCCGATCC | CGATACGCTC | GATCACATCG | CGGCCTGCGA | 720 |
| CGCGTTGCAT | CGCGCCGGTC | GCGATTACCG | CGTCGCGTAT | GCGAGCAGCA | GTCTCGCGGG | 780 |
| GCTGATCGCG | CTGGTGCGCT | CGGGGCAGGC | GTTCGCGGTG | ATGACGCAGA | CGGCCGTGCC | 840 |
| GGCCGACCTG | GCGATCGTCA | ACGGCGATCC | GCGGTTGCCG | CCGTTGCCGG | CGGTGGGCAT | 900 |
| TACGCTGAAG | TTCGACCGGA | AACGGCCGTC | GCATCTGACG | GCGGCGTTCG | CCGAGCATAT | 960 |
| TCGGGCCGTG | TTGCCGATGC | TGTGACGCGA | AGTCGTCGCG | CCGGAAACGC | AGGCATCGAC | 1020 |
| GCGGGATTCG | AGGCGTCGAC | GTTTGCCGTC | CATCTGACCG | AGTGCTTCGT | TCCGCATCGC | 1080 |
| CGAAGCAATA | AAAAAACCCG | CGAAGCCATG | CGCTGTCGCG | GGTTTTGCAA | ATGCACGAAA | 1140 |
| CACGGAAAAA | CCGTATTTGG | TGCCGACGGC | GAGACTCGAA | CTCGCACAGC | TTTCGCCACT | 1200 |
| ACCCCCTCAA | GATAGCGTGT | CTACCAATTT | CACCACGTCG | GCACTGCAAG | GGGCCGAATT | 1260 |
| GTAGCGTTAC | CATCGCGCGT | TTGTGAAGAG | GGTGTGACAC | GGCGAGCGGA | TGCGTGAAAG | 1320 |
| CGATCCCGGT | AGAATTCGGA | CGATCGGTCC | GACGACCATC | GCTACTGCCA | TCCGCTTTCT | 1380 |
| CCCCGTGACC | ACCACCCTCG | AACAACTGCA | G | | | 1411 |

(2) INFORMATION FOR SEQ ID NO:11:

(i) SEQUENCE CHARACTERISTICS:
 (A) LENGTH: 293 amino acids
 (B) TYPE: amino acid
 (D) TOPOLOGY: linear (ii) MOLECULE TYPE: protein (xi) SEQUENCE DESCRIPTION: SEQ ID NO:11:

```
Met Gln Gly Arg Lys Gly Ala Asn Thr Leu Gly Arg Ser Leu Glu Ile
 1               5                  10                  15

Asp Leu Leu Arg Ser Phe Val Val Ile Ala Glu Val Arg Ala Leu Ser
                20                  25                  30

Ala Ala Ala Arg Val Gly Arg Thr Gln Ser Ala Leu Ser Gln Gln Met
            35                  40                  45

Lys Arg Leu Glu Asp Ile Val Asp Gln Pro Leu Phe Gln Arg Thr Gly
    50                  55                  60

Arg Gly Val Val Leu Thr His Pro Gly Glu Arg Leu Leu Val His Ala
65                  70                  75                  80

Gln Arg Ile Leu Arg Gln His Asp Glu Ala Met Ala Asp Leu Cys Gly
                85                  90                  95

Thr Gly Leu Thr Gly Thr Ile Arg Phe Gly Cys Pro Asp Asp Tyr Ala
           100                 105                 110

Glu Val Phe Leu Pro Pro Leu Leu Arg Gln Phe Ser Ser Gln His Pro
       115                 120                 125

Gln Ala Ile Val Glu Ile Val Cys Gly Pro Thr Pro Arg Leu Leu Glu
   130                 135                 140

Gln Leu Glu Lys Arg Ala Val Asp Leu Ala Met Ile Ser Leu Pro Asp
145                 150                 155                 160

Asp Gly Ala Asn Asp Asp Ile Ile Arg Arg Glu Gln Leu Val Trp Ile
```

|     |     |     |     |     |     |     |     |     |     |     |     |     |     |     |
|---|---|---|---|---|---|---|---|---|---|---|---|---|---|---|
|     |     |     |     | 165 |     |     |     | 170 |     |     |     | 175 |     |     |
| Gly | Tyr | Pro | Gly | Leu | Glu | Pro | Ala | His | Phe | Asp | Pro | Leu | Pro | Leu | Ala |
|     |     |     | 180 |     |     |     |     | 185 |     |     |     | 190 |     |     |
| Leu | Ser | Asp | Pro | Asp | Thr | Leu | Asp | His | Ile | Ala | Ala | Cys | Asp | Ala | Leu |
|     |     | 195 |     |     |     |     | 200 |     |     |     |     | 205 |     |     |
| His | Arg | Ala | Gly | Arg | Asp | Tyr | Arg | Val | Ala | Tyr | Ala | Ser | Ser | Ser | Leu |
|     | 210 |     |     |     |     | 215 |     |     |     |     | 220 |     |     |     |
| Ala | Gly | Leu | Ile | Ala | Leu | Val | Arg | Ser | Gly | Gln | Ala | Phe | Ala | Val | Met |
| 225 |     |     |     |     | 230 |     |     |     |     | 235 |     |     |     |     | 240 |
| Thr | Gln | Thr | Ala | Val | Pro | Ala | Asp | Leu | Ala | Ile | Val | Asn | Gly | Asp | Pro |
|     |     |     |     | 245 |     |     |     |     | 250 |     |     |     |     | 255 |     |
| Arg | Leu | Pro | Pro | Leu | Pro | Ala | Val | Gly | Ile | Thr | Leu | Lys | Phe | Asp | Arg |
|     |     |     | 260 |     |     |     |     | 265 |     |     |     |     | 270 |     |     |
| Lys | Arg | Pro | Ser | His | Leu | Thr | Ala | Ala | Phe | Ala | Glu | His | Ile | Arg | Ala |
|     |     | 275 |     |     |     |     | 280 |     |     |     |     | 285 |     |     |     |
| Val | Leu | Pro | Met | Leu |
|     |     | 290 |     |     |

( 2 ) INFORMATION FOR SEQ ID NO:12:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( i x ) FEATURE:
        ( A ) NAME/KEY: Active-site
        ( B ) LOCATION: 12
        ( D ) OTHER INFORMATION: /note="Xaa is Lysine labeled with pyridoxyl group."

( x i ) SEQUENCE DESCRIPTION: SEQ ID NO:12:

| Asp | Gly | Val | Thr | Pro | Asp | Ile | Leu | Thr | Leu | Ser | Xaa | Thr | Leu | Gly | Ala |
|---|---|---|---|---|---|---|---|---|---|---|---|---|---|---|---|
| 1 |     |     |     | 5 |     |     |     |     | 10 |     |     |     |     | 15 |     |

( 2 ) INFORMATION FOR SEQ ID NO:13:

( i ) SEQUENCE CHARACTERISTICS:
        ( A ) LENGTH: 439 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

| Met | Leu | Ser | Lys | Leu | Ala | Ser | Leu | Gln | Thr | Val | Ala | Ala | Leu | Arg | Arg |
|---|---|---|---|---|---|---|---|---|---|---|---|---|---|---|---|
| 1 |     |     |     | 5 |     |     |     |     | 10 |     |     |     |     | 15 |     |
| Gly | Leu | Arg | Thr | Ser | Val | Ala | Ser | Ala | Thr | Ser | Val | Ala | Thr | Lys | Lys |
|     |     |     | 20 |     |     |     |     | 25 |     |     |     |     | 30 |     |     |
| Thr | Glu | Gln | Gly | Pro | Pro | Ser | Ser | Glu | Tyr | Ile | Phe | Glu | Arg | Glu | Ser |
|     |     | 35 |     |     |     |     | 40 |     |     |     |     | 45 |     |     |     |
| Lys | Tyr | Gly | Ala | His | Asn | Tyr | His | Pro | Leu | Pro | Val | Ala | Leu | Glu | Arg |
|     | 50 |     |     |     |     | 55 |     |     |     |     | 60 |     |     |     |     |
| Gly | Lys | Gly | Ile | Tyr | Met | Trp | Asp | Val | Glu | Gly | Arg | Gln | Tyr | Phe | Asp |
| 65 |     |     |     |     | 70 |     |     |     |     | 75 |     |     |     |     | 80 |
| Phe | Leu | Ser | Ala | Tyr | Gly | Ala | Val | Ser | Gln | Gly | His | Cys | His | Pro | Lys |
|     |     |     |     | 85 |     |     |     |     | 90 |     |     |     |     | 95 |     |
| Ile | Ile | Glu | Ala | Met | Lys | Ser | Gln | Val | Asp | Lys | Leu | Thr | Leu | Thr | Ser |
|     |     |     |     | 100 |     |     |     |     | 105 |     |     |     |     | 110 |     |
| Arg | Ala | Phe | Tyr | Asn | Asn | Val | Leu | Gly | Glu | Tyr | Glu | Glu | Tyr | Ile | Thr |
|     |     |     | 115 |     |     |     |     | 120 |     |     |     |     | 125 |     |     |

```
Lys  Leu  Phe  Asn  Tyr  Asn  Lys  Val  Leu  Pro  Met  Asn  Thr  Gly  Val  Glu
     130                 135                 140

Ala  Gly  Glu  Thr  Ala  Cys  Lys  Leu  Ala  Arg  Arg  Trp  Gly  Tyr  Thr  Val
145                      150                 155                           160

Lys  Gly  Ile  Gln  Lys  Tyr  Lys  Ala  Lys  Ile  Val  Phe  Ala  Val  Gly  Asn
                    165                 170                           175

Phe  Trp  Gly  Arg  Thr  Leu  Ser  Ala  Val  Ser  Ser  Thr  Asp  Pro  Thr
               180                      185                 190

Ser  Tyr  Asp  Gly  Phe  Gly  Pro  Phe  Met  Pro  Gly  Phe  Glu  Thr  Ile  Pro
               195                 200                 205

Tyr  Asn  Asp  Leu  Pro  Ala  Leu  Glu  Arg  Ala  Leu  Gln  Asp  Pro  Asn  Val
     210                 215                 220

Ala  Ala  Phe  Met  Val  Glu  Pro  Ile  Gln  Gly  Glu  Ala  Gly  Val  Ile  Val
225                      230                 235                           240

Pro  Asp  Pro  Gly  Tyr  Leu  Thr  Gly  Val  Arg  Glu  Leu  Cys  Thr  Arg  His
               245                 250                           255

Gln  Val  Leu  Phe  Ile  Ala  Asp  Glu  Ile  Gln  Thr  Gly  Leu  Ala  Arg  Thr
               260                 265                           270

Gly  Arg  Trp  Leu  Ala  Val  Asp  His  Glu  Asn  Val  Arg  Pro  Asp  Ile  Val
          275                 280                      285

Leu  Leu  Gly  Lys  Ala  Leu  Ser  Gly  Gly  Leu  Tyr  Pro  Val  Ser  Ala  Val
     290                 295                      300

Leu  Cys  Asp  Asp  Asp  Ile  Met  Leu  Thr  Ile  Lys  Pro  Gly  Glu  His  Gly
305                      310                 315                           320

Ser  Thr  Tyr  Gly  Gly  Asn  Pro  Leu  Gly  Cys  Arg  Ile  Ala  Ile  Ala  Ala
               325                      330                      335

Leu  Glu  Val  Leu  Glu  Glu  Glu  His  Leu  Ala  Glu  Asn  Ala  Asp  Lys  Met
               340                 345                      350

Gly  Ala  Ile  Leu  Arg  Lys  Glu  Leu  Met  Lys  Leu  Pro  Ser  Asp  Val  Val
               355                 360                 365

Thr  Ala  Val  Arg  Gly  Lys  Gly  Leu  Leu  Asn  Ala  Ile  Val  Ile  Arg  Glu
     370                 375                      380

Thr  Lys  Asp  Cys  Asp  Ala  Trp  Lys  Val  Cys  Leu  Arg  Leu  Arg  Asp  Asn
385                      390                 395                           400

Gly  Leu  Leu  Ala  Lys  Pro  Thr  His  Gly  Asp  Ile  Ile  Arg  Leu  Ala  Pro
                    405                 410                      415

Pro  Leu  Val  Ile  Lys  Glu  Asp  Glu  Ile  Arg  Glu  Ser  Val  Glu  Ile  Ile
               420                 425                      430

Asn  Lys  Thr  Ile  Leu  Ser  Phe
          435
```

( 2 ) INFORMATION FOR SEQ ID NO:14:

( i ) SEQUENCE CHARACTERISTICS:
        ( A ) LENGTH: 434 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Met  Ser  Leu  Asn  Asp  Asp  Ala  Thr  Phe  Trp  Arg  Asn  Ala  Arg  Gln  His
1                   5                   10                          15

Leu  Val  Arg  Tyr  Gly  Gly  Thr  Phe  Glu  Pro  Met  Ile  Ile  Glu  Arg  Ala
          20                      25                          30

Lys  Gly  Ser  Phe  Val  Tyr  Asp  Ala  Asp  Gly  Arg  Ala  Ile  Leu  Asp  Phe
          35                      40                          45
```

-continued

| | | | | | | | | | | | | | |
|---|---|---|---|---|---|---|---|---|---|---|---|---|---|
| Thr | Ser | Gly | Glu | Met | Ser | Ala | Val | Leu | Gly | His | Cys | His | Pro | Glu | Ile |
| | 50 | | | | 55 | | | | | 60 | | | |
| Val | Ser | Val | Ile | Gly | Glu | Tyr | Ala | Gly | Lys | Leu | Asp | His | Leu | Phe | Ser |
| 65 | | | | | 70 | | | | 75 | | | | | 80 |
| Gly | Ile | Val | Ser | Arg | Pro | Val | Val | Asp | Leu | Ala | Thr | Arg | Leu | Ala | Asn |
| | | | | 85 | | | | | 90 | | | | | 95 |
| Ile | Thr | Pro | Pro | Gly | Leu | Asp | Arg | Ala | Leu | Leu | Leu | Ser | Thr | Gly | Ala |
| | | | 100 | | | | | 105 | | | | | 110 |
| Glu | Ser | Asn | Glu | Ala | Ala | Ile | Arg | Met | Ala | Lys | Leu | Val | Thr | Gly | Lys |
| | | 115 | | | | | 120 | | | | | 125 |
| Tyr | Glu | Ile | Val | Gly | Phe | Ala | Gln | Ser | Trp | His | Gly | Met | Thr | Gly | Ala |
| | 130 | | | | | 135 | | | | | 140 |
| Ala | Ala | Ser | Ala | Thr | Tyr | Ser | Ala | Gly | Arg | Lys | Gly | Val | Gly | Pro | Ala |
| 145 | | | | 150 | | | | | 155 | | | | | 160 |
| Ala | Val | Gly | Ser | Phe | Ala | Ile | Pro | Ala | Pro | Phe | Thr | Tyr | Arg | Pro | Arg |
| | | | | 165 | | | | | 170 | | | | | 175 |
| Phe | Glu | Arg | Asn | Gly | Ala | Tyr | Asp | Tyr | Leu | Ala | Glu | Leu | Asp | Tyr | Ala |
| | | | 180 | | | | | 185 | | | | | 190 |
| Phe | Asp | Leu | Ile | Asp | Arg | Gln | Ser | Ser | Gly | Asn | Leu | Ala | Ala | Phe | Ile |
| | | 195 | | | | | 200 | | | | | 205 |
| Ala | Glu | Pro | Ile | Leu | Ser | Ser | Gly | Ile | Ile | Glu | Leu | Pro | Asp | Gly |
| | 210 | | | | | 215 | | | | | 220 |
| Tyr | Met | Ala | Ala | Leu | Lys | Arg | Lys | Cys | Glu | Ala | Arg | Gly | Met | Leu | Leu |
| 225 | | | | | 230 | | | | | 235 | | | | | 240 |
| Ile | Leu | Asp | Glu | Ala | Gln | Thr | Gly | Val | Gly | Arg | Thr | Gly | Thr | Met | Phe |
| | | | | 245 | | | | | 250 | | | | | 255 |
| Ala | Cys | Gln | Arg | Asp | Gly | Val | Thr | Pro | Asp | Ile | Leu | Thr | Leu | Ser | Lys |
| | | | 260 | | | | | 265 | | | | | 270 |
| Thr | Leu | Gly | Ala | Gly | Leu | Pro | Leu | Ala | Ala | Ile | Val | Thr | Ser | Ala | Ala |
| | | 275 | | | | | 280 | | | | | 285 |
| Ile | Glu | Glu | Arg | Ala | His | Glu | Leu | Gly | Tyr | Leu | Phe | Tyr | Thr | Thr | His |
| | 290 | | | | | 295 | | | | | 300 |
| Val | Ser | Asp | Arg | Cys | Pro | Pro | Ala | Gly | Val | Gly | Leu | Arg | Val | Leu | Asp |
| 305 | | | | | 310 | | | | | 315 | | | | | 320 |
| Val | Val | Gln | Arg | Asp | Gly | Leu | Val | Ala | Arg | Ala | Asn | Val | Met | Gly | Asp |
| | | | | 325 | | | | | 330 | | | | | 335 |
| Arg | Leu | Arg | Arg | Gly | Leu | Leu | Asp | Leu | Met | Glu | Arg | Phe | Asp | Cys | Ile |
| | | | 340 | | | | | 345 | | | | | 350 |
| Gly | Asp | Val | Arg | Gly | Arg | Gly | Leu | Leu | Leu | Gly | Val | Glu | Ile | Val | Lys |
| | | | 355 | | | | | 360 | | | | | 365 |
| Asp | Arg | Arg | Thr | Lys | Glu | Pro | Ala | Asp | Gly | Leu | Gly | Ala | Lys | Ile | Thr |
| | 370 | | | | | 375 | | | | | 380 |
| Arg | Glu | Cys | Met | Asn | Leu | Gly | Leu | Ser | Met | Asn | Ile | Val | Gln | Leu | Pro |
| 385 | | | | | 390 | | | | | 395 | | | | | 400 |
| Gly | Met | Gly | Gly | Val | Phe | Arg | Ile | Ala | Pro | Pro | Leu | Thr | Val | Ser | Glu |
| | | | | 405 | | | | | 410 | | | | | 415 |
| Asp | Glu | Ile | Asp | Leu | Gly | Leu | Ser | Leu | Leu | Gly | Gln | Ala | Ile | Glu | Arg |
| | | | 420 | | | | | 425 | | | | | 430 |
| Ala | Leu |

( 2 ) INFORMATION FOR SEQ ID NO:15:

( i ) SEQUENCE CHARACTERISTICS:
        ( A ) LENGTH: 23 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

Val Thr Pro Asp Ile Leu Thr Leu Ser Lys Thr Leu Gly Ala Gly Leu
1               5                   10                  15

Pro Leu Ala Ala Ile Val Thr
                20

( 2 ) INFORMATION FOR SEQ ID NO:16:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

Val Arg Pro Asp Ile Val Leu Leu Gly Lys Ala Leu Ser Gly Gly Leu
1               5                   10                  15

Tyr Pro Val Ser Ala Val Leu Cys
                20

( 2 ) INFORMATION FOR SEQ ID NO:17:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

Ala Lys Pro Asp Ile Val Leu Leu Gly Lys Ala Leu Ser Gly Gly Val
1               5                   10                  15

Leu Pro Val Ser Cys Val Leu Ser
                20

( 2 ) INFORMATION FOR SEQ ID NO:18:

( i ) SEQUENCE CHARACTERISTICS:
        ( A ) LENGTH: 29 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

Pro Gly Ile Asp Val Val Leu Ser Gln Ser Tyr Ala Lys Asn Met Gly
1               5                   10                  15

Leu Tyr Gly Glu Arg Ala Gly Ala Phe Ile Val Ile Cys
                20                  25

( 2 ) INFORMATION FOR SEQ ID NO:19:

( i ) SEQUENCE CHARACTERISTICS:
        ( A ) LENGTH: 29 amino acids
        ( B ) TYPE: amino acid
        ( D ) TOPOLOGY: linear ( i i ) MOLECULE TYPE: protein ( x i ) SEQUENCE DESCRIPTION: SEQ ID NO:19:

Glu Gly Phe Glu Leu Phe Cys Ala Gln Ser Phe Ser Lys Asn Phe Gly
1               5                   10                  15

Leu Tyr Asn Glu Arg Val Gly Asn Leu Thr Val Val Ala
                20                  25

( 2 ) INFORMATION FOR SEQ ID NO:20:

( i ) SEQUENCE CHARACTERISTICS:
   ( A ) LENGTH: 29 amino acids
   ( B ) TYPE: amino acid
   ( D ) TOPOLOGY: linear ( i i ) MOLECULE TYPE: protein ( x i ) SEQUENCE DESCRIPTION: SEQ ID NO:20:

```
Met His Lys Glu Leu Ile Val Ala Ser Ser Tyr Ser Lys Asn Phe Gly
 1               5                  10                  15

Leu Tyr Asn Glu Arg Val Gly Ala Cys Thr Leu Val Ala
                20                  25
```

( 2 ) INFORMATION FOR SEQ ID NO:21:

( i ) SEQUENCE CHARACTERISTICS:
   ( A ) LENGTH: 30 amino acids
   ( B ) TYPE: amino acid
   ( D ) TOPOLOGY: linear ( i i ) MOLECULE TYPE: protein ( x i ) SEQUENCE DESCRIPTION: SEQ ID NO:21:

```
Gln Gly Ile Asp Ile Leu Tyr Ser Gly Ser Gln Lys Val Leu Val Ala
 1               5                  10                  15

Pro Pro Gly Ile Ser Leu Ile Ser Phe Asn Asp Lys Ala Lys
                20                  25                  30
```

( 2 ) INFORMATION FOR SEQ ID NO:22:

( i ) SEQUENCE CHARACTERISTICS:
   ( A ) LENGTH: 20 amino acids
   ( B ) TYPE: amino acid
   ( D ) TOPOLOGY: linear ( i i ) MOLECULE TYPE: protein ( x i ) SEQUENCE DESCRIPTION: SEQ ID NO:22:

```
Gln Glu Leu Ala Ser Phe His Ser Val Ser Lys Gly Phe Met Gly Glu
 1               5                  10                  15

Cys Gly Phe Arg
                20
```

( 2 ) INFORMATION FOR SEQ ID NO:23:

( i ) SEQUENCE CHARACTERISTICS:
   ( A ) LENGTH: 293 amino acids
   ( B ) TYPE: amino acid
   ( D ) TOPOLOGY: linear ( i i ) MOLECULE TYPE: protein ( x i ) SEQUENCE DESCRIPTION: SEQ ID NO:23:

```
Met Gln Gly Arg Lys Gly Ala Asn Thr Leu Gly Arg Ser Leu Glu Ile
 1               5                  10                  15

Asp Leu Leu Arg Ser Phe Val Val Ile Ala Glu Val Arg Ala Leu Ser
                20                  25                  30

Ala Ala Ala Arg Val Gly Arg Thr Gln Ser Ala Leu Ser Gln Gln Met
                35                  40                  45

Lys Arg Leu Glu Asp Ile Val Asp Gln Pro Leu Phe Gln Arg Thr Gly
         50                  55                  60

Arg Gly Val Val Leu Thr His Pro Gly Glu Arg Leu Leu Val His Ala
65                   70                  75                  80

Gln Arg Ile Leu Arg Gln His Asp Glu Ala Met Ala Asp Leu Cys Gly
```

```
                          85                          90                             95
    Thr  Gly  Leu  Thr  Gly  Thr  Ile  Arg  Phe  Gly  Cys  Pro  Asp  Asp  Tyr  Ala
                   100                      105                 110
    Glu  Val  Phe  Leu  Pro  Pro  Leu  Leu  Arg  Gln  Phe  Ser  Ser  Gln  His  Pro
                   115                      120                 125
    Gln  Ala  Ile  Val  Glu  Ile  Val  Cys  Gly  Pro  Thr  Pro  Arg  Leu  Leu  Glu
              130                      135                 140
    Gln  Leu  Glu  Lys  Arg  Ala  Val  Asp  Leu  Ala  Met  Ile  Ser  Leu  Pro  Asp
    145                      150                      155                      160
    Asp  Gly  Ala  Asn  Asp  Asp  Ile  Ile  Arg  Arg  Glu  Gln  Leu  Val  Trp  Ile
                        165                      170                      175
    Gly  Tyr  Pro  Gly  Leu  Glu  Pro  Ala  His  Phe  Asp  Pro  Leu  Pro  Leu  Ala
                   180                      185                      190
    Leu  Ser  Asp  Pro  Asp  Thr  Leu  Asp  His  Ile  Ala  Ala  Cys  Asp  Ala  Leu
              195                      200                      205
    His  Arg  Ala  Gly  Arg  Asp  Tyr  Arg  Val  Ala  Tyr  Ala  Ser  Ser  Ser  Leu
         210                      215                      220
    Ala  Gly  Leu  Ile  Ala  Leu  Val  Arg  Ser  Gly  Gln  Ala  Phe  Ala  Val  Met
    225                      230                      235                      240
    Thr  Gln  Thr  Ala  Val  Pro  Ala  Asp  Leu  Ala  Ile  Val  Asn  Gly  Asp  Pro
                        245                      250                      255
    Arg  Leu  Pro  Pro  Leu  Pro  Ala  Val  Gly  Ile  Thr  Leu  Lys  Phe  Asp  Arg
                   260                      265                      270
    Lys  Arg  Pro  Ser  His  Leu  Thr  Ala  Ala  Phe  Ala  Glu  His  Ile  Arg  Ala
              275                      280                      285
    Val  Leu  Pro  Met  Leu
              290
```

( 2 ) INFORMATION FOR SEQ ID NO:24:

( i ) SEQUENCE CHARACTERISTICS:
        ( A ) LENGTH: 287 amino acids
        ( B ) TYPE: amino acid
        ( D ) TOPOLOGY: linear ( i i ) MOLECULE TYPE: protein ( x i ) SEQUENCE DESCRIPTION: SEQ ID NO:24:

```
    Met  Ala  Ala  Val  Asn  Leu  Arg  His  Ile  Glu  Ile  Phe  His  Ala  Val  Met
    1                   5                       10                       15
    Thr  Ala  Gly  Ser  Leu  Thr  Glu  Ala  Ala  His  Leu  Leu  His  Thr  Ser  Gln
                   20                       25                       30
    Pro  Thr  Val  Ser  Arg  Glu  Leu  Ala  Arg  Phe  Glu  Lys  Val  Ile  Gly  Leu
                   35                       40                       45
    Lys  Leu  Phe  Glu  Arg  Val  Arg  Gly  Arg  Leu  His  Pro  Thr  Val  Gln  Gly
         50                       55                       60
    Leu  Arg  Leu  Phe  Glu  Glu  Val  Gln  Arg  Ser  Trp  Tyr  Gly  Leu  Asp  Arg
    65                       70                       75                       80
    Ile  Val  Ser  Ala  Ala  Glu  Ser  Leu  Arg  Glu  Phe  Arg  Gln  Gly  Glu  Leu
                        85                       90                       95
    Ser  Ile  Ala  Cys  Leu  Pro  Val  Phe  Ser  Gln  Ser  Phe  Leu  Pro  Gln  Leu
                   100                      105                      110
    Leu  Gln  Pro  Phe  Leu  Ala  Arg  Tyr  Pro  Asp  Val  Ser  Leu  Asn  Ile  Val
                   115                      120                      125
    Pro  Gln  Glu  Ser  Pro  Leu  Leu  Glu  Glu  Trp  Leu  Ser  Ala  Gln  Arg  His
              130                      135                      140
    Asp  Leu  Gly  Leu  Thr  Glu  Thr  Leu  His  Thr  Pro  Ala  Gly  Thr  Glu  Arg
    145                      150                      155                      160
```

```
Thr Glu Leu Leu Ser Leu Asp Glu Val Cys Val Leu Pro Pro Gly His
                165                 170                 175
Pro Leu Ala Val Lys Lys Val Leu Thr Pro Asp Asp Phe Gln Gly Glu
            180                 185                 190
Asn Tyr Ile Ser Leu Ser Arg Thr Asp Ser Tyr Arg Gln Leu Leu Asp
        195                 200                 205
Gln Leu Phe Thr Glu His Gln Val Lys Arg Arg Met Ile Val Glu Thr
    210                 215                 220
His Ser Ala Ala Ser Val Cys Ala Met Val Arg Ala Gly Val Gly Ile
225                 230                 235                 240
Ser Val Val Asn Pro Leu Thr Ala Leu Asp Tyr Ala Ala Ser Gly Leu
            245                 250                 255
Val Val Arg Arg Phe Ser Ile Ala Val Pro Phe Thr Val Ser Leu Ile
            260                 265                 270
Arg Pro Leu His Arg Pro Ser Ser Ala Leu Val Gln Ala Phe Ser
    275                 280                 285
```

( 2 ) INFORMATION FOR SEQ ID NO:25:

( i ) SEQUENCE CHARACTERISTICS:
( A ) LENGTH: 292 amino acids
( B ) TYPE: amino acid
( D ) TOPOLOGY: linear ( i i ) MOLECULE TYPE: protein ( x i ) SEQUENCE DESCRIPTION: SEQ ID NO:25:

```
Met Lys Leu Gln Gln Leu Arg Tyr Ile Val Glu Val Val Asn His Asn
1               5                   10                  15
Leu Asn Val Ser Ser Thr Ala Glu Gly Leu Tyr Thr Ser Gln Pro Gly
            20                  25                  30
Ile Ser Lys Gln Val Arg Met Leu Glu Asp Glu Leu Gly Ile Gln Ile
        35                  40                  45
Phe Ser Arg Ser Gly Lys His Leu Thr Gln Val Thr Pro Ala Gly Gln
    50                  55                  60
Glu Ile Ile Arg Ile Ala Arg Glu Val Leu Ser Lys Val Asp Ala Ile
65                  70                  75                  80
Lys Ser Val Ala Gly Glu His Thr Trp Pro Asp Lys Gly Ser Leu Tyr
            85                  90                  95
Ile Ala Thr Thr His Thr Gln Ala Arg Tyr Ala Leu Pro Asn Val Ile
            100                 105                 110
Lys Gly Phe Ile Glu Arg Tyr Pro Arg Val Ser Leu His Met His Gln
        115                 120                 125
Gly Ser Pro Thr Gln Ile Ala Asp Ala Val Ser Lys Gly Asn Ala Asp
    130                 135                 140
Phe Ala Ile Ala Thr Glu Ala Leu His Leu Tyr Glu Asp Leu Val Met
145                 150                 155                 160
Leu Pro Cys Tyr His Trp Asn Arg Ala Ile Val Thr Pro Asp His
            165                 170                 175
Pro Leu Ala Gly Lys Lys Ala Ile Thr Ile Glu Glu Leu Ala Gln Tyr
            180                 185                 190
Pro Leu Val Thr Tyr Thr Phe Gly Phe Thr Gly Arg Ser Glu Leu Asp
        195                 200                 205
Thr Ala Phe Asn Arg Ala Gly Leu Thr Pro Arg Ile Val Phe Thr Ala
    210                 215                 220
Thr Asp Ala Asp Val Ile Lys Thr Tyr Val Arg Leu Gly Leu Gly Val
225                 230                 235                 240
```

-continued

```
Gly  Val  Ile  Ala  Ser  Met  Ala  Val  Asp  Pro  Val  Ala  Asp  Pro  Asp  Leu
               245                      250                      255

Val  Arg  Val  Asp  Ala  His  Asp  Ile  Phe  Ser  His  Ser  Thr  Thr  Lys  Ile
               260                      265                      270

Gly  Phe  Arg  Arg  Ser  Thr  Phe  Leu  Arg  Ser  Tyr  Met  Tyr  Asp  Phe  Ile
               275                      280                      285

Gln  Arg  Phe  Ala
               290
```

( 2 ) INFORMATION FOR SEQ ID NO:26:

( i ) SEQUENCE CHARACTERISTICS:
        ( A ) LENGTH: 291 amino acids
        ( B ) TYPE: amino acid
        ( D ) TOPOLOGY: linear ( i i ) MOLECULE TYPE: protein ( x i ) SEQUENCE DESCRIPTION: SEQ ID NO:26:

```
Met  Asn  Ile  Arg  Asp  Leu  Glu  Tyr  Leu  Val  Ala  Leu  Ala  Glu  His  Arg
1                    5                        10                       15

His  Phe  Arg  Arg  Ala  Ala  Asp  Ser  Cys  His  Val  Ser  Gln  Pro  Thr  Leu
               20                       25                       30

Ser  Gly  Gln  Ile  Arg  Lys  Leu  Glu  Asp  Glu  Leu  Gly  Val  Met  Leu  Leu
               35                       40                       45

Glu  Arg  Thr  Ser  Arg  Lys  Val  Leu  Phe  Thr  Gln  Ala  Gly  Met  Leu  Leu
          50                       55                       60

Val  Asp  Gln  Ala  Arg  Thr  Val  Leu  Arg  Glu  Val  Lys  Val  Leu  Lys  Glu
65                       70                       75                       80

Met  Ala  Ser  Gln  Gln  Gly  Glu  Thr  Met  Ser  Gly  Pro  Leu  His  Ile  Gly
                    85                       90                       95

Leu  Ile  Pro  Thr  Val  Gly  Pro  Tyr  Leu  Leu  Pro  His  Ile  Ile  Pro  Met
               100                      105                      110

Leu  His  Gln  Thr  Phe  Pro  Lys  Leu  Glu  Met  Tyr  Leu  His  Glu  Ala  Gln
               115                      120                      125

Thr  His  Gln  Leu  Leu  Ala  Gln  Leu  Asp  Ser  Gly  Lys  Leu  Asp  Cys  Val
          130                      135                      140

Ile  Leu  Ala  Leu  Val  Lys  Glu  Ser  Glu  Arg  Phe  Ile  Glu  Val  Pro  Leu
145                      150                      155                      160

Phe  Asp  Glu  Pro  Met  Leu  Leu  Ala  Ile  Tyr  Glu  Asp  His  Pro  Trp  Ala
                    165                      170                      175

Asn  Arg  Glu  Cys  Val  Pro  Met  Ala  Asp  Leu  Ala  Gly  Glu  Lys  Leu  Leu
               180                      185                      190

Met  Leu  Glu  Asp  Gly  His  Cys  Leu  Arg  Asp  Gln  Ala  Met  Gly  Phe  Cys
               195                      200                      205

Phe  Glu  Ala  Gly  Ala  Asp  Glu  Asp  Thr  His  Phe  Arg  Ala  Thr  Ser  Leu
          210                      215                      220

Glu  Thr  Leu  Arg  Asn  Met  Val  Ala  Ala  Gly  Ser  Gly  Ile  Thr  Leu  Leu
225                      230                      235                      240

Pro  Ala  Leu  Ala  Val  Pro  Pro  Glu  Arg  Lys  Arg  Asp  Gly  Val  Val  Tyr
                    245                      250                      255

Leu  Pro  Cys  Ile  Lys  Pro  Glu  Pro  Arg  Arg  Thr  Ile  Gly  Leu  Val  Tyr
               260                      265                      270

Arg  Pro  Gly  Ser  Pro  Leu  Arg  Ser  Arg  Tyr  Glu  Gln  Leu  Ala  Glu  Ala
               275                      280                      285

Ile  Arg  Ala
     290
```

( 2 ) INFORMATION FOR SEQ ID NO:27:

( i ) SEQUENCE CHARACTERISTICS:
        ( A ) LENGTH: 276 amino acids
        ( B ) TYPE: amino acid
        ( D ) TOPOLOGY: linear ( i i ) MOLECULE TYPE: protein ( x i ) SEQUENCE DESCRIPTION: SEQ ID NO:27:

```
Met Ile Glu Ile Lys His Leu Lys Thr Leu Gln Ala Leu Arg Asn Ser
 1               5                  10                  15
Gly Ser Leu Ala Ala Ala Ala Ala Val Leu His Gln Thr Gln Ser Ala
                20                  25                  30
Leu Ser His Gln Phe Ser Asp Leu Glu Gln Arg Leu Gly Phe Arg Leu
             35                  40                  45
Phe Val Arg Lys Ser Gln Pro Leu Arg Phe Thr Pro Gln Gly Glu Val
         50                  55                  60
Leu Leu Gln Leu Ala Asn Gln Val Leu Pro Gln Ile Ser Arg Ala Leu
 65                  70                  75                  80
Gln Ala Cys Asn Glu Pro Gln Gln Thr Arg Leu Arg Ile Ala Ile Glu
                 85                  90                  95
Cys His Ser Cys Ile Gln Trp Leu Thr Pro Ala Leu Glu Asn Phe Arg
                100                 105                 110
Ala Ser Trp Pro Gln Val Glu Met Asp Phe Thr Ser Gly Val Thr Phe
            115                 120                 125
Asp Pro Gln Pro Ala Leu Gln Gln Gly Glu Leu Asp Leu Val Met Thr
        130                 135                 140
Ser Asp Ile Leu Pro Arg Ser Glu Leu His Tyr Ser Pro Met Phe Asp
145                 150                 155                 160
Phe Glu Val Arg Leu Val Leu Ala Pro Asp His Pro Leu Ala Ser Lys
                165                 170                 175
Thr Gln Ile Thr Pro Glu Asp Leu Ala Ser Glu Thr Leu Leu Ile Tyr
            180                 185                 190
Pro Val Gln Arg Ser Arg Leu Asp Val Trp Arg His Phe Leu Gln Pro
        195                 200                 205
Ala Gly Ile Ser Pro Leu Leu Lys Ser Val Asp Asn Thr Leu Leu Leu
    210                 215                 220
Ile Gln Met Val Ala Ala Arg Met Gly Ile Ala Ala Leu Pro His Trp
225                 230                 235                 240
Val Val Glu Ser Val Glu Arg Gln Gly Leu Val Val Thr Lys Thr Leu
                245                 250                 255
Gly Asp Gly Leu Trp Ser Arg Leu Tyr Ala Ala Val Arg Asp Ala Thr
            260                 265                 270
Ser Val Arg Arg
        275
```

( 2 ) INFORMATION FOR SEQ ID NO:28:

( i ) SEQUENCE CHARACTERISTICS:
        ( A ) LENGTH: 251 amino acids
        ( B ) TYPE: amino acid
        ( D ) TOPOLOGY: linear ( i i ) MOLECULE TYPE: protein ( x i ) SEQUENCE DESCRIPTION: SEQ ID NO:28:

```
Met Glu Leu Arg His Leu Arg Tyr Phe Val Thr Val Val Glu Glu Gln
 1               5                  10                  15
Ser Ile Ser Lys Ala Ala Glu Lys Leu Cys Ile Ala Gln Pro Pro Leu
                20                  25                  30
```

| | | | | | | | | | | | | | |
|---|---|---|---|---|---|---|---|---|---|---|---|---|---|
| Ser | Arg | Gln<br>35 | Ile | Gln | Lys | Leu | Glu<br>40 | Glu | Leu | Gly | Ile<br>45 | Gln | Leu | Phe |
| Glu | Arg<br>50 | Gly | Phe | Arg | Pro<br>55 | Ala | Lys | Val | Thr | Glu | Ala<br>60 | Gly | Met | Phe | Phe |
| Tyr<br>65 | Gln | His | Ala | Val | Gln<br>70 | Ile | Leu | Thr | His | Thr<br>75 | Ala | Gln | Ala | Ser | Ser<br>80 |
| Met | Ala | Lys | Arg | Ile<br>85 | Ala | Thr | Val | Ser | Gln<br>90 | Thr | Leu | Arg | Ile | Gly<br>95 | Tyr |
| Val | Ser | Ser | Leu<br>100 | Leu | Tyr | Gly | Leu | Leu<br>105 | Pro | Glu | Ile | Ile | Tyr<br>110 | Leu | Phe |
| Arg | Gln | Gln<br>115 | Asn | Pro | Glu | Ile | His<br>120 | Ile | Glu | Leu | Ile | Glu<br>125 | Cys | Gly | Thr |
| Lys | Asp<br>130 | Gln | Ile | Asn | Ala | Leu<br>135 | Lys | Gln | Gly | Lys | Ile<br>140 | Asp | Leu | Gly | Phe |
| Gly<br>145 | Arg | Leu | Lys | Ile | Thr<br>150 | Asp | Pro | Ala | Ile | Arg<br>155 | Arg | Ile | Val | Leu | His<br>160 |
| Lys | Glu | Gln | Leu | Lys<br>165 | Leu | Ala | Ile | His | Lys<br>170 | His | His | His | Leu | Asn<br>175 | Gln |
| Phe | Ala | Ala | Thr<br>180 | Gly | Val | His | Leu | Ser<br>185 | Gln | Ile | Ile | Asp | Glu<br>190 | Pro | Met |
| Leu | Leu | Tyr<br>195 | Pro | Val | Ser | Gln | Lys<br>200 | Pro | Asn | Phe | Ala | Thr<br>205 | Phe | Ile | Gln |
| Ser | Leu<br>210 | Phe | Thr | Glu | Leu | Gly<br>215 | Leu | Val | Pro | Ser | Lys<br>220 | Leu | Thr | Glu | Ile |
| Arg<br>225 | Glu | Ile | Gln | Leu | Ala<br>230 | Leu | Gly | Leu | Val | Ala<br>235 | Ala | Gly | Glu | Gly | Val<br>240 |
| Cys | Ile | Val | Pro | Ala<br>245 | Ser | Ala | Trp | Ile | Leu<br>250 | Gly | | | | | |

( 2 ) INFORMATION FOR SEQ ID NO:29:

( i ) SEQUENCE CHARACTERISTICS:
        ( A ) LENGTH: 25 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:29:

CGCGCTGCTG CTCAGCACCG GCGCG     25

( 2 ) INFORMATION FOR SEQ ID NO:30:

( i ) SEQUENCE CHARACTERISTICS:
        ( A ) LENGTH: 26 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:30:

GCCGAGGTGC GCGCGCTCAG CGCGGC     26

REPRESSOR PROTEIN AND OPERON FOR REGULATING EXPRESSION OF POLYPEPTIDES AND ITS USE IN THE PREPARATION OF 2,2-DIALKYGLYCINE DECARBOXYLASE OF *PSEUDOMONAS CEPACIA*

CROSS-REFERENCE TO RELATED APPLICATION

This application is a continuation-in-part of application Ser. No. 07/501,814 filed Mar. 30, 1990, now U.S. Pat. No. 5,210,025 issued May 11, 1993. The entire disclosure of the parent application is relied upon and expressly incorporated by reference herein.

TECHNICAL FIELD OF THE INVENTION

This invention relates to a purified nucleotide sequence coding for a repressor protein for regulating gene expression. In addition, this invention relates to a recombinant expression vector containing the nucleotide sequence, an *E. coli* cell transformed or transfected with the recombinant expression vector, and the use of the *E. coli* cells for preparing *Pseudomonas cepacia* 2,2-dialkylglycine decarboxylase or a heterologous gene product. Further, this invention provides a repressor protein encoded by the nucleotide sequence, wherein the repressor protein is in a purified form.

In one embodiment of this invention the gene encoding this enzyme in *Pseudomonas cepacia* was cloned, expressed in *E. coli* and sequenced. Another aspect of this invention demonstrates that expression of the decarboxylase gene is controlled by a nearby divergent open reading frame that encodes a repressor protein.

This invention also relates to recombinant vectors comprising elements of the 2,2-dialkylglycine decarboxylase expression system, which comprises the 2,2-dialkylglycine decarboxylase gene (dgdA), the 2,2-dialkylglycine decarboxylase repressor gene (dgdR), and their associated regulatory elements, linked to a structural gene to be expressed. In specific embodiments of this invention such a vector comprises operators O1 and O2 of the decarboxylase gene, a promoter, and the structural gene to be expressed. In other embodiments, a recombinant vector of this invention also comprises the 2,2-dialkylglycine repressor gene.

Another aspect of this invention relates to recombinant vectors comprising elements of the 2,2-dialkylglycine expression system linked to a restriction endonuclease recognition site into which a heterologous structural gene can be inserted. The restriction site is preferably a unique restriction site in the vector and is situated to provide an operable linkage between elements of the vector regulating expression and a heterologous structural gene following insertion of such a gene into the vector at the restriction site. In specific embodiments of this invention such a vector comprises operators O01 and O2 of the decarboxylase gene, a promoter, and a structural gene to be expressed. In other embodiments, such a vector also comprises the 2,2-dialkylglycine carboxylase repressor gene.

BACKGROUND OF THE INVENTION

Soil bacteria metabolize dialkylglycines such as 2-methylalanine via oxidative decarboxylation catalyzed by the vitamin B-6-dependent dialkylglycine decarboxylase (Aaslestad et al., 1984; Bailey et al., 1967; Lamartiniere et al., 1971; Sato et al., 1978).

The 2,2-dialkylglycine decarboxylase of the soil bacterium *Pseudomonas cepacia* was first reported by Aaslestad and Larson (1964) and was later investigated in several laboratories (Bailey and Dempsey, 1967; Bailey et al., 1970; Lamartiniere et al., 1971; Honma et al., 1972; Sato et al., 1978; and Keller and O'Leary, 1979). This pyridoxal 5'-phosphate-dependent enzyme catalyzes decomposition of substrate amino acids such as 2-methylalanine and isovaline in two steps: (i) release of carbon dioxide and ketone with transfer of the amino group to the cofactor to give enzyme-bound pyridoxamine 5'-phosphate and (ii) amino transfer from cofactor to pyruvate forming L-alanine and regenerating the cofactor in the aldehyde oxidation state. The decarboxylation step is analogous to the so-called abortive decarboxylation catalyzed by several pyridoxal 5'-phosphate-dependent amino acid decarboxylases, which competes with the normal hydrogen for carboxylate replacement reaction (Sukhareva, 1986). The dialkylglycine decarboxylase is of interest because it normally catalyzes both decarboxylation and amino transfer. Therefore, the question arises whether this enzyme is an aminotransferase that through evolution has added a decarboxylase capability or is a decarboxylase that has evolved an amino transfer capability. I provide a preliminary answer to this question by showing that the dialkylglycine decarboxylase primary structure is homologous to several aminotransferases but not to decarboxylases.

While the dialkylglycines, 2-methylalanine and isovaline (2-ethylalanine), which are substrates for the enzyme and induce dgdA gene expression, are present in low concentrations in soils, dialkylglycine decomposition is the most likely function of these genes. However, only the dialkylglycines, but no other small- and medium-sized protein-derived amino acids, induce dgdA gene expression. Dialkylglycines may have been introduced into soils by carbonaceous meteorites (Engel et al., 1990) or, at the Cretaceous-Tertiary boundary, by asteroid impact (Zhao et al., 1989). Another source of these amino acids may be soil fungi, such as *Trichodema reesii*, which produce peptide antibiotics, such as alamethicin, that contain 2-methylalanine and isovaline (Bruckner et al., 1984). Whatever the source, the dialkylglycines are rare in the soil environment. Consequently, tight control over biosynthesis of the decarboxylase appears necessary.

The biological role of the dialkylglycine decarboxylase remains unclear. The substrates 2-methylalanine and isovaline occur naturally as major constituents of cytotoxic peptides produced by soil fungi such as *Trichoderma viride* (Bruckner et al., 1980; Bruckner and Pryzbylaki, 1984; Schmitt and Jung, 1985) and as organic components of carbonaceous meteorites (Kvenvolden et al., 1971). Racemic isovaline and 2-methylalanine have been found recently in an iridium-rich Cretaceous-Tertiary boundary layer, further supporting an extraterrestrial source for this material (Zhao and Bada, 1989). Thus, the enzyme may have evolved to use the rare dialkylglycines of cosmic origin, or it may be a part of a metabolic pathway for breaking down cytotoxic peptides and the constituent amino acids.

The available structural information about the 2,2-dialkylglycine decarboxylase is sparse. Lamartiniere et al. (1971) showed by equilibrium sedimentation that a dialkylglycine decarboxylase isolated from *P. cepacia* has a molecular mass of 188 kDa with four identical 47 kDa subunits. They also reported a peptide map and amino acid composition data consistent with a 47 kDa subunit. Sato et al, (1978) also studied the *P. cepacia* dialkylglycine decarboxylase, showing by gel electrophoresis that the 180 kDa holoenzyme contained four identical subunits of approximately 45 kDa and presenting chemical labeling evidence for a catalytically important histidine residue.

Biochemical interest in 2-methylalanine- and isovaline-binding proteins is based in part on the ability of these proteins to discriminate between the stereoisomers of amino acids with small alpha-alkyl substituents such as alanine, isovaline, and 2-methylnorvaline. The amino acid binding sites of the dialkylglycine decarboxylase and the decarboxylase gene repressor may have some common structural features, since they both bind 2-methylalanine and related amino acids. Another enzyme, hog kidney aminoacylase, which hydrolyzes N-acyl-2,2-dialkylglycines with greater than 99% enantioselectivity (Baker et al., 1952; Keller et al., 1986; Jones et al., 1991), may have evolved similar structural features.

SUMMARY OF THE INVENTION

Aaslestad and Larson (1964) found that the *P. cepacia* produced the decarboxylase only when the organism's minimal salts-glucose growth medium was supplemented with 2-methylalanine. This suggested that decarboxylase gene expression is induced in some way by the dialkylglycine substrate. This question has been examined using the cloned and sequenced *P. cepacia* DNA. Based upon these experiments it has been determined that the cloned DNA codes for an intact dialkylglycine decarboxylase repression-induction system that functions in *Escherichia coli*. Functional analysis of partially deleted plasmids and computer analysis of the sequence upstream of the structural gene provide evidence for a repressor gene. Also, several 2,2-dialkylglycine stereoisomers were synthesized and tested as inducers of decarboxylase gene expression.

More particularly, this invention provides a purified nucleotide sequence coding for a repressor protein for regulating gene expression. The nucleotide sequence comprises about a 687 bp nucleotide region beginning about 81 bases upstream from the 2,2-dialkylglycine decarboxylase gene which is shown in FIG. 3 (SEQ ID NO: 8). The gene codes for the repressor protein, which comprises about 229 amino acids.

This invention also provides recombinant expression vectors pKBD6, pUC19C7, pGEM-7Z14 which contain the nucleotide sequence coding for the repressor protein, as well as the recombinant expression vector pGEM-7Z14/3e.

In addition, this invention provides an *E. coli* cell transformed with the recombinant expression vectors of the invention.

Also, this invention provides a process for preparing *Pseudomonas cepacia* 2,2-dialkylglycine decarboxylase. The process comprises providing a biomass comprised of *E. coli* cells of the invention. The *E. coli* cells are cultured in the presence of a gene inducing agent selected from the group consisting of S-isovaline, 2-methylalanine, L-2-aminobutanoic acid, or 1-aminocyclopentane carboxylic acid. The gene inducing agent is employed in the biomass in an amount sufficient to induce transcription of the *Pseudomonas cepacia* 2,2-dialkylglycine decarboxylase gene in the cells.

When *E. coli* cells of the invention transformed with pUC19C7, pGEM-7Z14, or pGEM-7Z14/3e are used in a process for preparing *Pseudomonas cepacia* 2,2-dialkylglycine decarboxylase, they may also be cultured in the presence of isopropyl-1-thio-b-D-galactopyranoside (IPTG) to induce a lac operon and carbenicillin, a penicillin analog, to force *E. coli* cells to maintain the plasmids inside each cell. These plasmids carry a gene for penicillinase, an enzyme that deactivates the carbenicillin antibiotic.

Finally, this invention provides a purified repressor protein comprised of the amino acid sequence of the repressor protein shown in FIG. 4 (SEQ ID NO: 11). In specific embodiments of this invention, the repressor protein is in oligomeric or dimeric form.

In a further embodiment, this invention also relates to a macromolecular complex comprising a recombinant DNA molecule and the repressor protein shown in FIG. 4 (SEQ ID NO: 11), where the recombinant DNA molecule comprises either operator O1 or operator O2 and a promoter. In specific embodiments of this invention, the repressor protein binds the recombinant DNA molecule at operator O1 or operator O2 to form the macromolecular complex. In other embodiments, the promoter of the macromolecular complex is a promoter capable of promoting transcription in bacteria, such as the lac, trp or tac promoter.

An additional embodiment of this invention relates to a DNA molecule consisting essentially of operator O1. This invention also relates to a DNA molecule consisting essentially of operator O2.

This invention also relates to recombinant vectors comprising a nucleotide sequence encoding 2,2-dialkylglycine decarboxylase repressor protein, a nucleotide sequence coding for a ribosome binding site, a promoter, and a restriction endonuclease cleavage site for insertion of a foreign gene downstream from said nucleotide sequence coding for a ribosome binding site.

In an additional embodiment, this invention also relates to a recombinant vector comprising operators O1 and O2, a nucleotide sequence coding for a ribosome binding site downstream of the operators, a first promoter situated between operators O1 and O2, and a heterologous structural gene downstream of the operators, wherein O1 and O2 are able to cooperatively bind 2,2-dialkylglycine decarboxylase repressor protein to prevent binding of polymerase to the first promoter, and the first promoter is operably limited to the heterologous gene for expression of the gene. In a specific embodiment of this invention, the recombinant expression vector also includes the dgdR gene located upstream of the first promoter and operatively linked to a second promoter.

This invention further relates to a method of producing a heterologous protein in a host cell. This method comprises the steps of providing a host cell transformed with a recombinant vector of the invention and containing the 2,2-dialkylglycine decarboxylase repressor protein of *Pseudomonas cepacia*, dissociating repressor protein from operator O1, and expressing a foreign gene inserted in the recombinant vector.

A further aspect of this invention is alignment of the repressor gene product sequence with the LysR family of DNA binding proteins. Yet another aspect of this invention is the expression of the dgdR gene product using a tac-promoter vector. Another aspect of this invention relates to the two dyad-symmetric operator sites that bind repressor located within the dgdA and dgdR genes.

BRIEF DESCRIPTION OF THE DRAWINGS

This invention will be more fully described with reference to the drawings in which:

FIG. 3 shows the nucleotide sequence of the cloned P. cepacia DNA (3' end of the +strand) with the deduced amino acid sequence of the 2,2-dialkylglycine decarboxylase structural gene. The nucleotide sequence is SEQ ID NO: 8: and the amino acid sequence is SEQ ID NO: 9. Underlined amino acid residues were verified by automated sequencing of the purified recombinant dialkylglycine decarboxylase and the active site peptide; low yield or uninterpretable cycles are denoted by dotted lines. A ribosome binding site is underlined, and a possible transcription termination site is overlined.

FIG. 4 shows the nucleotide sequence of the cloned P. cepacia DNA (3' end of the -strand) with the predicted amino acid sequence of the repressor protein. The nucleotide sequence is SEQ ID NO: 10 and the amino acid sequence is SEQ ID NO: 11.

FIG. 9 is an alignment of deduced sequences of 2,2-dialkylglycine decarboxylase (this work) and rat ornithine aminotransferase (Mueckler and Pitot, 1985). A modification of the method of Needleman and Wunsch (1970) with a window of 30, a gap penalty of 10, and a size penalty of 2 was used. Identical residues or conservative substitutions are boxed. Active site lysines are marked by dots. The top sequence (rat ornithine aminotransferase) is SEQ ID NO: 13, and the bottom sequence (2,2-dialkylglycine decarboxylase) is SEQ ID NO: 14.

FIG. 10 is an alignment of active site peptides of several pyridoxal 5'-phosphate-dependent aminotransferases. Positions homologous to either the dialkylglycine decarboxylase or ornithine aminotransferase are boxed. The gaps in the ornithine aminotransferase-aspartate aminotransferase alignment were assigned by Mueckler and Pitot (1985). [1]This work [SEQ ID NO: 15]; Mueckler and Pitot (1985) [SEQ ID NO: 16]; [3]Degols, 1987 [SEQ. ID NO: 17:]; [4]Graf-Hauser et al. (1983) [SEQ. ID NO: 18]; [5]Doonan et al (1975)[SEQ ID NO: 19]; [6]Fotheringham et al. (1986) [SEQ ID NO: 20]; [7]Oda et al. (1987) [SEQ ID NO: 21]; [8]Tanase et al. (1979) [SEQ ID NO: 22].

FIG. 11 depicts plasmids pGEM7Z14/6a, pGEM7Z14/2b, pBTac1, and pJKDGDR1. The clear region is *Pseudomonas cepacia* DNA, the black region is the P. cepacia dgdR gene, the stippled region is the P. cepacia dgdA gene, the cross-hatched regions are vector sequences, the horizontally-lined region is the ampicillin resistance gene. The filled arrows are PCR primers and the open arrow is the tac promoter. Restriction sites are B, BamHI; E, EcoRI; P, PstI; S, SalI; X, XbaI.

FIG. 12 is an alignment of the amino acid sequence deduced from the dgdR gene sequence with the sequences of five LysR-family proteins. The highlighted residues are conservative replacements occurring in at least three proteins at one site. The alignment was made using the Multalin program. The sequence of DGDR is SEQ ID NO: 23, the sequence of LYSR is SEQ ID NO: 24:, the sequence of CYSB is SEQ ID NO: 25:, the sequence of OXYR is SEQ ID NO: 26, the sequence of METR is SEQ ID NO: 27, and the sequence of CATM is SEQ ID NO: 28.

Lane E is a BRL 0.1 kb ladder. The arrow indicates the position of the single shifted DNA band.

Figure 15:
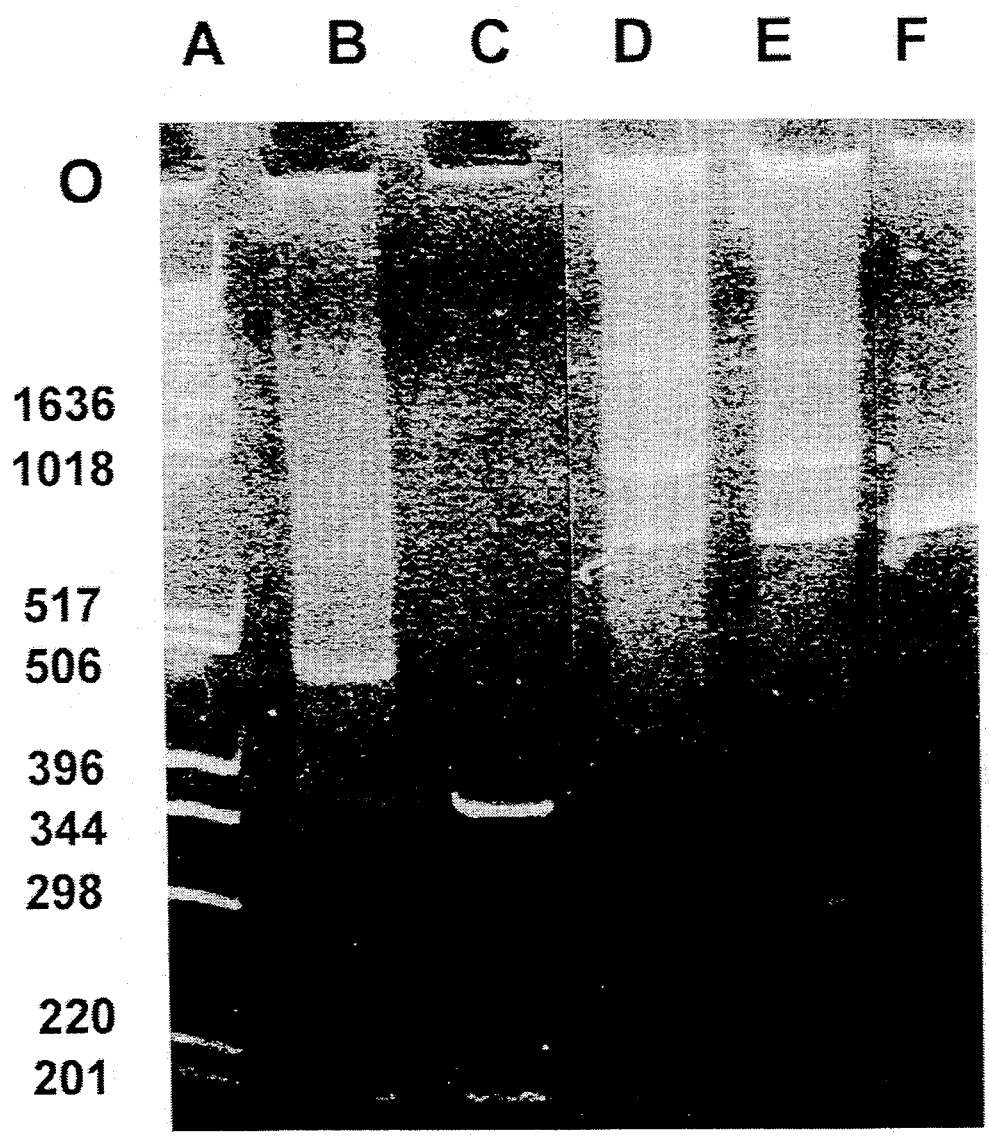

FIG. 15 depicts gel mobility shift assays for the 367 and 788 bp fragments. In lanes C and E, no protein is added; in lanes B and D, 1 μg of dgdR-containing extract is added. Lanes B and C contain 50 ng 367 bp fragment partially digested with SalI. Lanes D and E contain 50 ng of the 788 bp fragment. Lane A contains a BRL 1 kb ladder.

Figure 16:
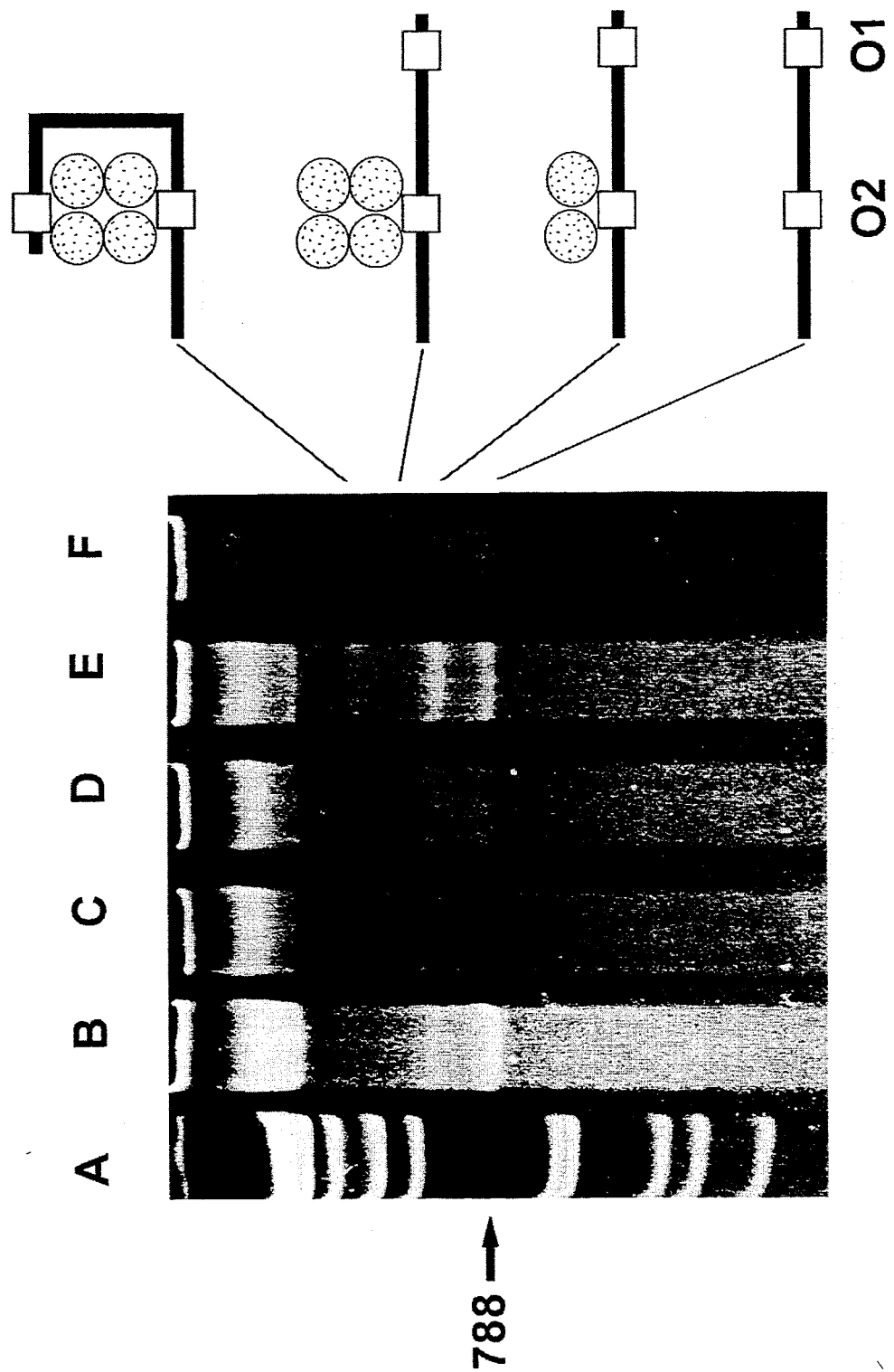

FIG. 16 depicts gel mobility shift assays for the 788 bp fragment in the presence and absence of 2-methylalanine. Lane A is the BRL 1 kb ladder. Lanes B–F contain 50 ng of the 788 bp fragment. Lanes C–E contain 0.1–1 μg of dgdR-containing extract added. Lane F contains 1 μg of dgdR-containing protein and 20 mM 2-methylalanine.

FIG. 17 depicts the sequences of Operators O1 [SEQ ID NO: 29] and O2 [SEQ ID No: 30]. The dyad-symmetric positions are boxed.

DETAILED DESCRIPTION OF PREFERRED EMBODIMENT

The method of this invention will now be described in greater detail. This invention relates to a cloned repressor gene, a cloned expression system, a process for expressing a gene, and a purified repressor protein.

Generally, a gene to be expressed can be inserted into a cloning vector in many ways. The nucleic acid fragment to be ligated can have cohesive ends compatible with any combination of sites in the vector. Alternatively, the nucleic acid fragment can have one or more blunt ends that can be ligated to corresponding blunt ends in the cloning sites of the vector. The nucleic acid fragment to be ligated can be further processed, if desired, by successive exonuclease deletion.

In the event that the nucleic acid fragment to be ligated does not contain a desired combination of cohesive ends, the fragment can be modified by adding a linker, an adaptor, or homopolymer tailing by one of three methods.

The first method involves the use of linkers, which are short pieces of double-stranded DNA of known nucleotide sequence. The linker, which contains a restriction site, can be ligated to the DNA molecules by using an excess quantity of the linker in the ligation reaction. Digestion of the resulting molecules with the appropriate restriction enzyme will cleave the linkers at the restriction sites to form the cohesive ends. The modified fragment is then ready for ligation into a vector having compatible cohesive ends.

The second method of attaching a cohesive end to a blunt-ended DNA molecule is through the use of adaptors, which are also short oligonucleotides. The adaptor has one blunt end and one cohesive end. The blunt end is ligated to the blunt ends of the DNA fragments to produce a new molecule with cohesive ends. Once again, the modified DNA fragment is then ready for ligation into a vector having corresponding cohesive ends.

The third method of producing cohesive ends on blunt-ended molecules involves homopolymer tailing. The homopolymer is a polymer in which all the subunits are the same. In order to ligate two tailed molecules, the homopolymers must be complementary. Thus, for example, poly(dC) tails can be attached to the vector and poly(dC) tails can be attached to the DNA fragment to be expressed. Base pairing between the two will occur when the molecules are mixed.

The expression vector employed in practicing this invention can be any double-stranded DNA molecule capable of transporting the nucleic acid fragment to be expressed into a host cell and capable of replicating within the cell. More particularly, the vector must contain at least one DNA sequence that can act as the origin of replication in a host cell. In addition, the vector must contain one or more sites for insertion of the nucleic acid sequence to be expressed. These sites will ordinarily correspond to restriction enzyme sites at which cohesive ends can be formed, and which are complementary to the cohesive ends on the nucleic acid fragment to be expressed. In general, this invention can be carried out with plasmid, bacteriophage, or cosmid vectors having these characteristics.

The vector can be introduced into the host cell using any technique appropriate for the specific vector. Examples such as transformation or transfection are well known in the art and protocols can be found in standard and widely available texts (Maniatis et al., 1982).

Restriction endonucleases employed in this invention are those that both recognize and cleave a DNA molecule at a specific sequence (Class II endonucleases). It is preferred that the restriction endonucleases employed in this invention be functionally pure; they should be substantially free of phosphatase contamination.

When a plasmid vector is used it is preferred that the plasmid carry one or more genes responsible for a useful characteristic, such as selectable marker, displayed by the host cell. Gene cloning strategies with plasmids often use a drug resistance marker to help locate bacterial colonies in which the genes have been cloned. In one type of strategy, plasmids having genes for resistance to two different drugs are chosen. For example, insertion of the DNA fragment of interest into a gene for an antibiotic inactivates the gene and destroys drug resistance. The second drug resistance gene is not affected when bacterial cells are transformed with the recombinants, and colonies containing the gene of interest can be selected by resistance to the second drug and susceptibility to the first drug.

Preferred antibiotic markers are genes imparting chloramphenicol, ampicillin, or tetracycline resistance to the host cell. It is preferred that antibiotic resistance be employed as the selectable marker to insure that the host cell in a culture contains the plasmid.

When a plasmid is employed, the plasmid can be derived from bacteria or some other organism or the plasmid can be synthetically prepared. The plasmid can replicate independently of the host cell chromosome or an integrative plasmid (episome) can be employed. The plasmid can make use of the DNA replicative enzymes of the host cell in order to replicate or the plasmid can carry genes that code for the enzymes required for plasmid replication. A number of different plasmids can be employed in practicing this invention. Typical of the plasmids that can be utilized are pBR322, pBR325, ColE1, RP4, pUC19, and the 2 μm circle that occurs in many strains of the yeast *Saccharomyces cerevisiae*.

The cloning vehicle can also be a bacteriophage, which is also referred to herein as a phage. The phage can have a head and tail structure or the phage can be characterized by a filamentous structure. It will be understood that this invention can be practiced with phage vectors that proliferate by lytic or by lysogenic infection.

Cloning and expression can be carried in procaryotic or eucaryotic cells. The host will of course be one that is compatible with the vector and the proteins that are expressed. Cloning and expression are preferably carried out in bacterial or yeast cells, although cells of fungal, animal, and plant origin can also be employed. The preferred host cells are bacterial cells, such as *E. coli,* as well as species of *Bacillus* and *Pseudomonas.* The use of *E. coli* cells is particularly preferred because bacterial plasmids and bacteriophages replicate in these cells.

As used herein the term "promoter" is used in its conventional sense to refer to the region of DNA capable of binding RNA polymerase to initiate transcription.

As used herein the term "ribosome binding site" is also used in its conventional sense to refer to the region of mRNA capable of binding ribosomes to initiate translation. This term is meant to include regions of mRNA involved in nucleic acid—nucleic acid as well as protein—nucleic acid interactions.

The term "operator" is used herein to refer to a region of DNA capable of binding repressor protein to inhibit expression from a neighboring promoter.

The process of this invention can be carried out as a batch or as a continuous fermentation. The term "continuous fermentation" is used in its usual sense and means that nutrients are fed to a fermenter substantially continuously and that an output, or effluent, stream is substantially constantly withdrawn from the fermenter. The nutrient stream usually comprises an aqueous organic substrate solution. The effluent stream comprises biomass and the liquid phase from the fermentation medium. The term "batch fermentation" is also used in its conventional sense and refers to fermentation without continuous inflow and outflow.

Fermentation can be carried out in a bioreactor, such as a chemostat, tower fermenter or immobilized-cell bioreactor. Mixing can be supplied by an impeller, agitator or other suitable means and should be sufficiently vigorous that the vessel contents are of substantially uniform composition, but not so vigorous that the microorganism is disrupted or metabolism inhibited.

The identity of the chemical constituents in the nutrient medium and the amount of each constituent should be sufficient to meet the elemental requirements for cell mass and should supply appropriate energy for cell maintenance. The nutrient medium should contain sources of carbon, nitrogen, potassium, phosphorus, sulfur, magnesium, calcium, and iron in required amounts. The chemical constituents should also meet specific nutritional requirements including vitamins and trace minerals. This invention will now be described in greater detail with reference to a specific preferred embodiment.

The cloning and sequencing of the structural gene of the *P. cepacia* 2,2-dialkylglycine decarboxylase was undertaken to establish whether this enzyme is structurally and evolutionarily more closely related to the B-6-dependent decarboxylases than to aminotransferases. It is reported here, among other things, (i) the sequence of a cloned 3969 bp segment of *P. cepacia* DNA containing the 2,2-dialkylglycine decarboxylase structural gene, (ii) purification of the recombinant decarboxylase, (iii) determination of the amino acid sequence of the amino terminus and the active site peptide, and (iv) alignment of the deduced amino acid sequence of the deduced amino acid sequence of this decarboxylase with various aminotransferases.

Figure 1:
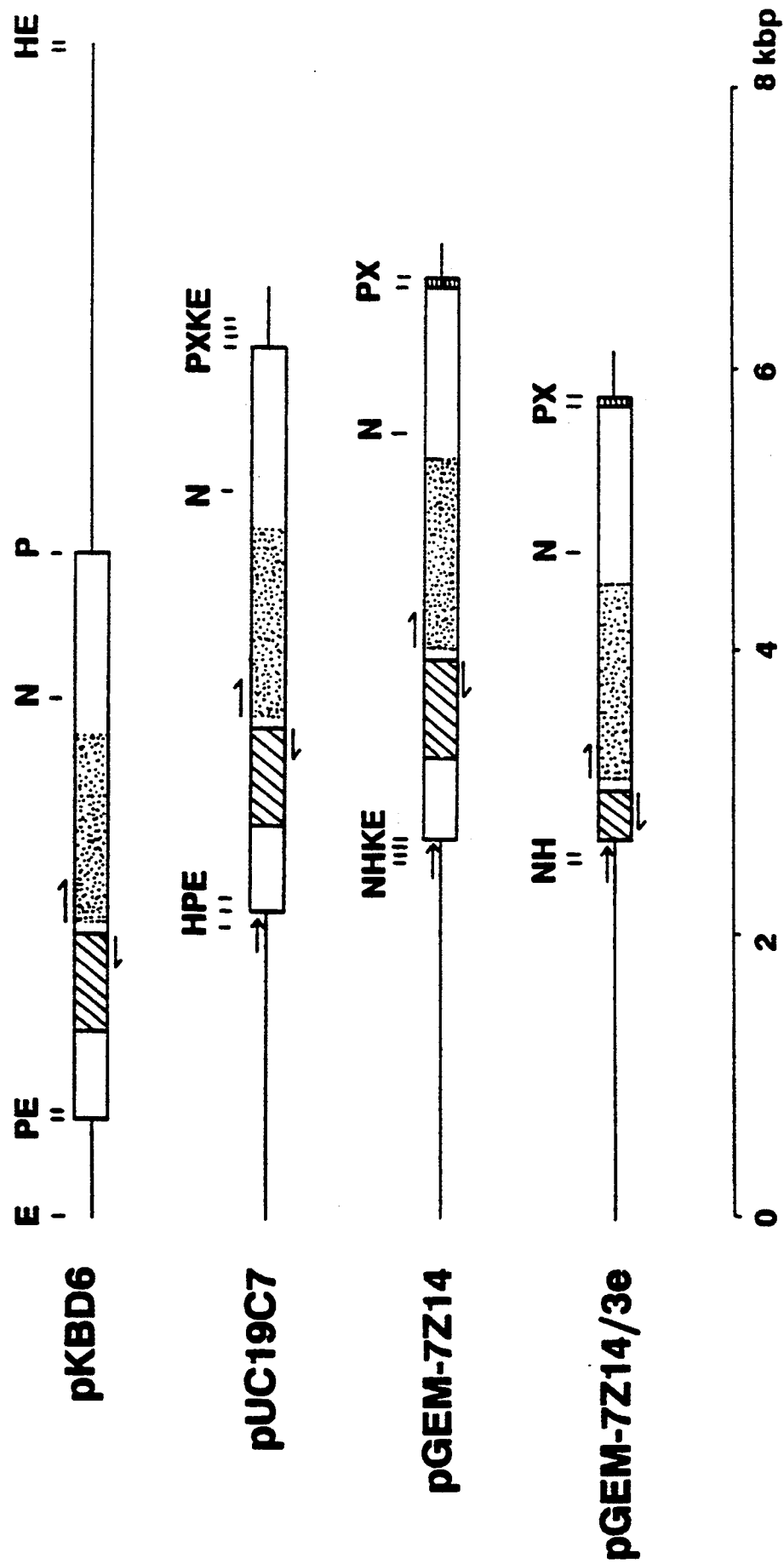
FIG. 1 depicts restriction maps of recombinant plasmids. Lines are vector DNA (pKBD6 is derived from pBR322, pUC19C7 from pUC19, and pGEM-7Z14 from pGEM-7Zf(+), and boxes are inserts of P. cepacia DNA. Stippled region contains 2,2-dialkylglycine decarboxylase structural gene; angle-hatched region contains the repressor gene; horizontally hatched region contains a portion of the pUC19 multiple cloning site. Plasmid pGEM-7Z14/3e is 1 of 10 plasmids derived from pGEM-7Z14 that have a portion of the P. cepacia DNA deleted by exonuclease treatment. Restriction sites: E, EcoRI; P, PstI; N, NsiI; H, HindIII; K, KpnI; X, XbaI. Double-headed arrow, pUC19 lac promoter, single-headed arrows, direction of transcription of *Pseudomonas* genes.

Cloning—Isolation of the dialkylglycine decarboxylase gene was simplified by the inability of *E. coli* to metabolize 2,2-dialkylglycines. Thus, a library created by ligating PstI-restricted *P. cepacia* DNA into the PstI site of pBR322 was screened for the dialkylglycine decarboxylase gene by plating the transformation mixture on LB/tetracycline agar to select transformants and subsequently making a replica transfer to 2-methylalanine/glucose agar. Isolated from one of several colonies that survived the transfer was a 16-kbp (kilobase pairs) recombinant plasmid containing several heterologous PstI fragments. A PstI digest of the plasmid was subcloned back into PstI-cut pBR322 and a pair of smaller recombinant plasmids, pKBD6 and PKBD14, were isolated; these were shown by restriction analysis to differ only in the orientation of a 4.0-kbp insert (FIG. 1). The 4.0-kbp PstI-PstI fragment was transferred into pUC19 to give pUC19C7 and the slightly smaller XbaI-EcoRI fragment of pUC19C7 (sequencing later showed that the EcoRI site is 77 bases away from the end of the insert) was transferred into pGEM-7Zf(+) to give pGEM-7Z14 (FIG. 1). Also, pUC19H1 was constructed from pUC19C7 by deletion of a 1.3-kbp SphI fragment (not shown). All the above recombinant plasmids, pKBD6, pKBD14, pUC19C7, pUC19H1, and pGEM-7Z14, confer on *E. coli* hosts the ability to grow on 2-methylalanine/glucose agar.

DNA Sequence—Sequencing was carried out using a modified Sanger dideoxy method (Sanger et al., 1977; Kraft et al, 1988). The (+)-strand of the insert (the upper strand in FIG. 1 and lower strand in FIG. 2; the coding strand for the decarboxylase structural gene) was sequenced using a 20-mer primer complementary to pGEM-7Z sequences on the left side of the insert and, as templates, plasmids with progressively larger deletions from the left. The -strand of the insert (the lower strand in FIG. 1 and upper strand in FIG. 2; the coding strand for the putative repressor gene) was sequenced using a 20-mer primer complementary to pUC19 sequences on the right side of the insert and, as templates, plasmids with progressively larger deletions from the right. One hundred percent of the control and structural genes was sequenced on both strands; 90% of the remaining sequence was determined on both strands. The 3969-nucleotide sequence is shown in two segments. FIG. 3 (SEQ ID NO: 8) shows the 3' end of the (+)-strand that contains the decarboxylase structural gene; FIG. 4 (SEQ ID NO: 11) shows the 3' end of the (−)-strand that contains the control gene. The cloned fragment contains 68% G+C, which is similar to the 65–68% G+C observed in various *Pseudomonas* species (Sober, 1968).

Figure 5:
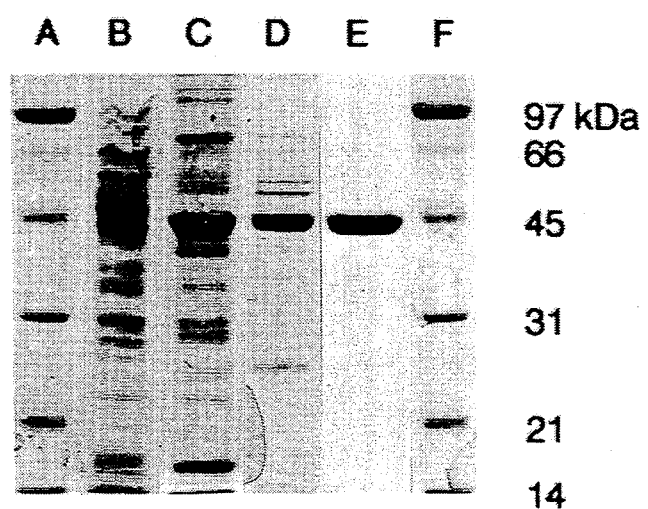
FIG. 5 shows SDS polyacrylamide gel electrophoresis of recombinant 2,2-dialkylglycine decarboxylase at various stages of purification. Lanes A and F, BioRad MW standards; B, sonicate supernatant; C, Butyl-TSK wash D, DEAE 5-PW active fraction; E, size exclusion active fraction.

Enzyme Expression and Purification—The recombinant decarboxylase was purified from *E. Coli* JM 109 carrying pGEM-7Z14/8b, a truncated derivative of pGEM-7Z14 with 1332 base pairs deleted from the left end leaving 63 nucleotides ahead of the decarboxylase gene. In this and other pGEM-7Z14 derivatives, the vector lac promoter lies upstream of and points toward the dialkylglycine decarboxylase gene (FIG. 1). When carbenicillin and IPTG were added to the JM109/pGEM-7Z14/8b growth medium, the dialkylglycine decarboxylase comprised about 0.5% of the cell extract, similar to levels induced by 2-methylalanine in *Pseudomonas* (Keller and O'Leary, 1979; Sato et al., 1978). The decarboxylase was purified from JM109/pGEM7Z14/8b in three steps using ammonium sulfate precipitation, ion exchange chromatography, and FPLC ion exchange chromatography. The purified enzyme was homogeneous as judged by SDS polyacrylamide gel electrophoresis (See Table 1 and FIG. 5).

RESULTS

TABLE 1

Purification of Recombinant 2,2-Dialkylglycine Decarboxylase

| | Protein (mg) | Total $U^a$ | $U^a$/mg protein | Yield (%) |
|---|---|---|---|---|
| Cell Sonicate | 260. | 1710 | 8.6 | 100 |
| Butyl-TSK | 4.8 | 710 | 148. | 42 |
| DEAE-5PW | 0.201 | 669 | 3400 | 39 |
| 300SW | 0.126 | 306 | 2430 | 18 |

$^a$One Unit = 1 nanomole $CO_2$ per min at pH 7.90 and 25° C.

Sequence of the Amino Terminus—The purified protein was sequenced at the amino terminus by automated Edman degradation. The results are included in FIG. 3. In the 14 cycles in which the phenylthiohydantoin-amino acid yields were high enough to make clear identifications, the experimentally determined residues matched the predicted ones. This sequence also shows that the decarboxylase terminal N-formylmethionine has been removed, but no additional amino-terminal proteolysis has occurred.

Figure 6:
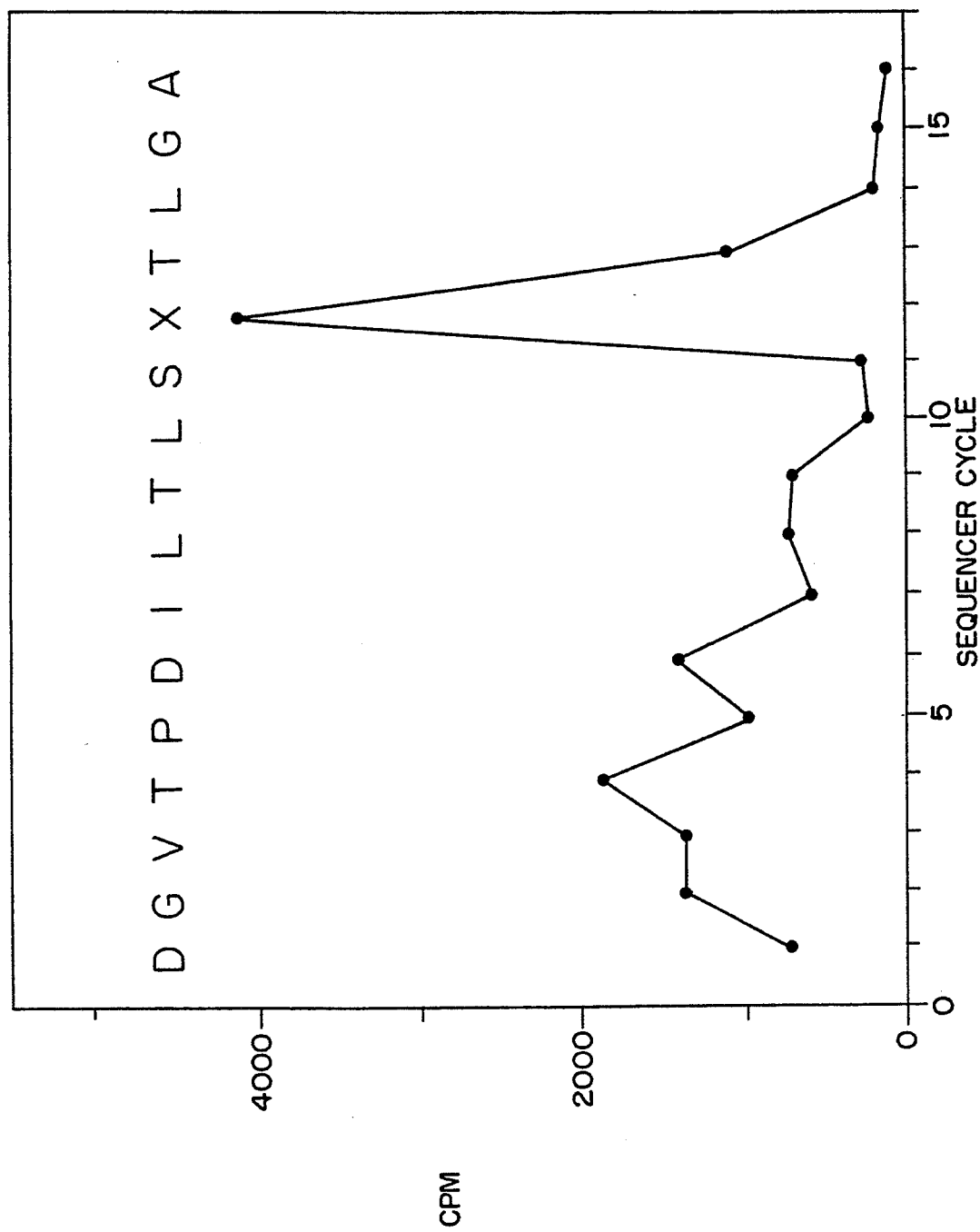
FIG. 6 depicts radioactivity released with each sequencer cycle during sequencing of the $^3$H-pyridoxal 5'-phosphate-labeled tryptic peptide. The sequence of the tryptic peptide is SEQ ID NO: 12.
Figure 7A:
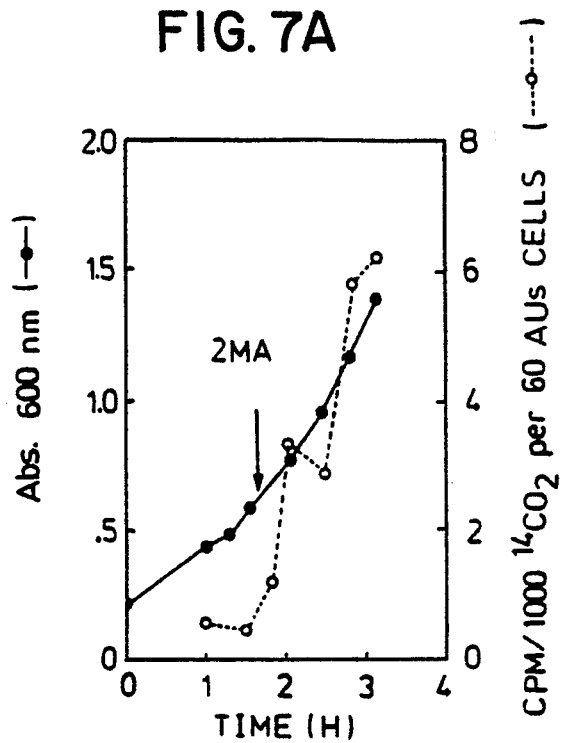
FIG. 7 depicts induction of dialkylglycine decarboxylase activity in E. coli DH5a/pKBD6 cultures by various amino acids. One-liter cultures containing minimal salts, glucose, NH$_4$Cl, and tetracycline (12 μg/ml) were supplemented at the indicated time with amino acid (final concentration, 10 mM). Absorbance of the culture was measured at 600 nm in a 1-cm cell ( — ). Each activity assay contained 60 absorbance units of resuspended bacteria (○—○)
Figure 7B:
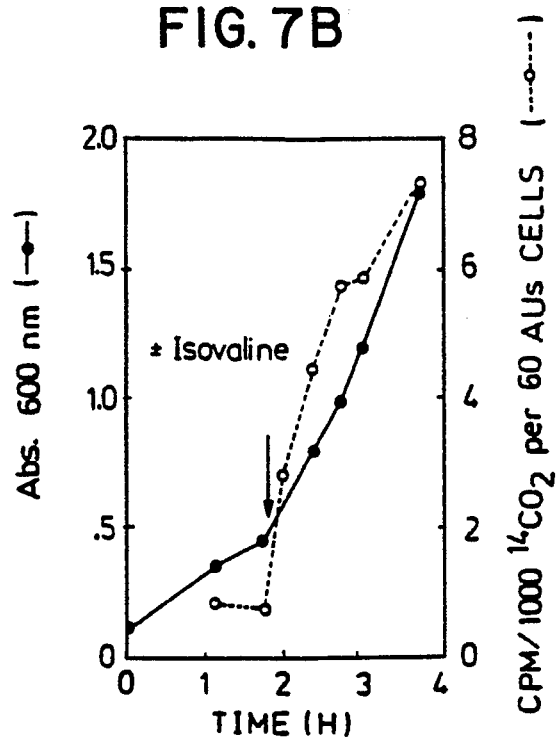
Figure 7C:
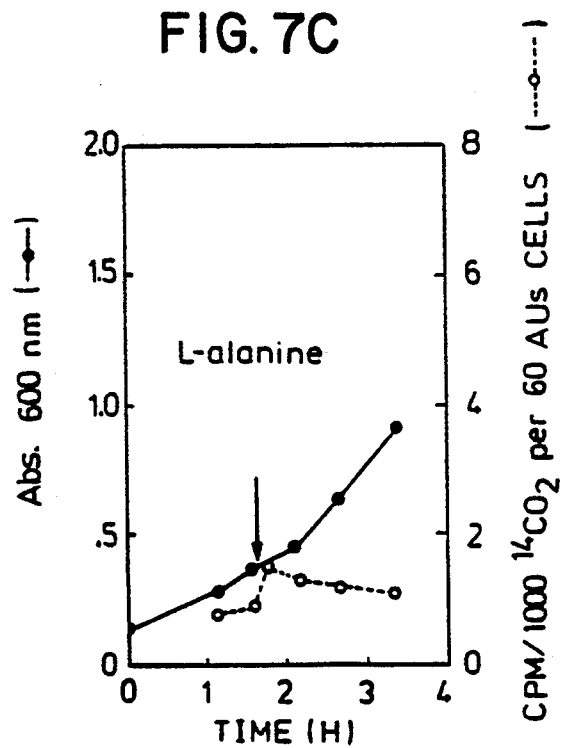
Figure 7D:
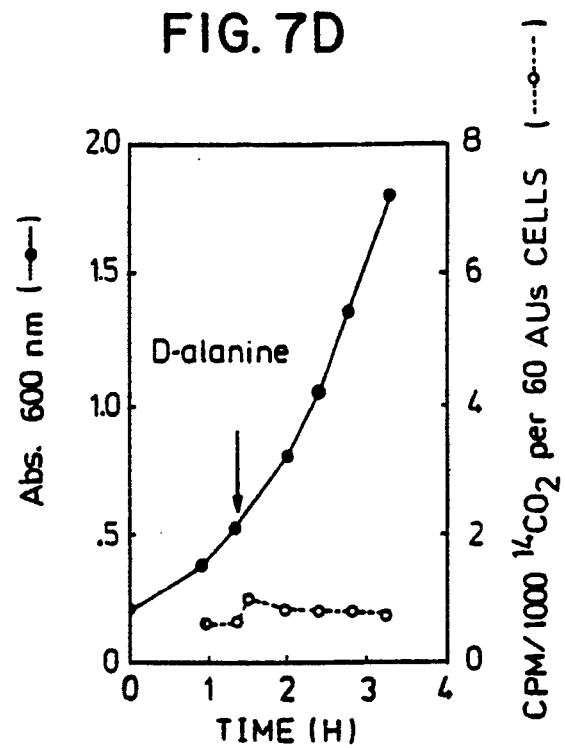

Sequence of the Active Site Peptide—The decarboxylase active site was labeled using a variation of the method first introduced by Fischer et al. (1958). In this procedure, the active site lysine-[4'-$^3$H]pyridoxal 5'-phosphate imine bond of the holoenzyme was reduced with sodium borohydride. The labeled active site peptide was isolated by trypsin digestion followed by reversed phase high performance liquid chromatography separation of the resulting peptides. The major radioactive peptide was sequenced, and the amount of radioactivity released by each cycle of the automated Sequencer was determined. Sixteen cycles were clearly identifiable: all except cycle 12 agreed with the predicted amino acid sequence beginning after R260. Cycle 12 produced the most radioactivity and showed no identifiable peak on the Sequencer (see FIG. 6). This is presumably the cofactor-labeled lysine residue predicted by the DNA sequence.

Figure 2:
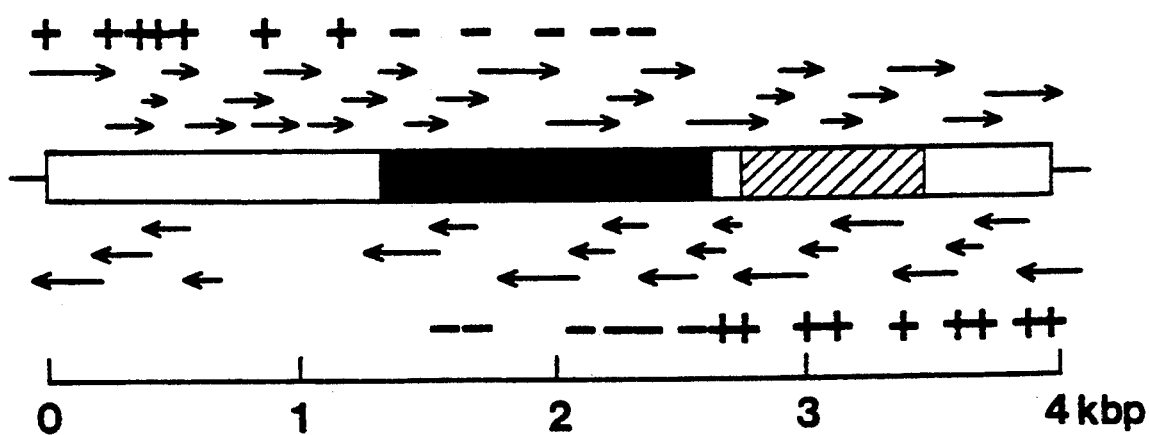
FIG. 2 describes sequencing strategy and growth characteristics of partially deleted plasmids on 2-methylalanine/glucose agar. Arrows begin at the last base of each partially deleted plasmid and point as far as sequence was determined. Arrows above the box refer to unidirectional deletions from pUC19C7; arrows below the box refer to unidirectional deletions from pGEM-7Z14. JM109 carrying a plasmid deleted to the (+) symbol forms large colonies on 2-methylalanine/glucose agar; JM109 carrying a plasmid deleted to the (−) symbol does not grow on 2-methylalanine/glucose agar. The 2,2-dialkylglycine decarboxylase structural gene is on the lower strand in the solid region; the repressor gene is on the upper strand in the crosshatched region.
Figure 3B:
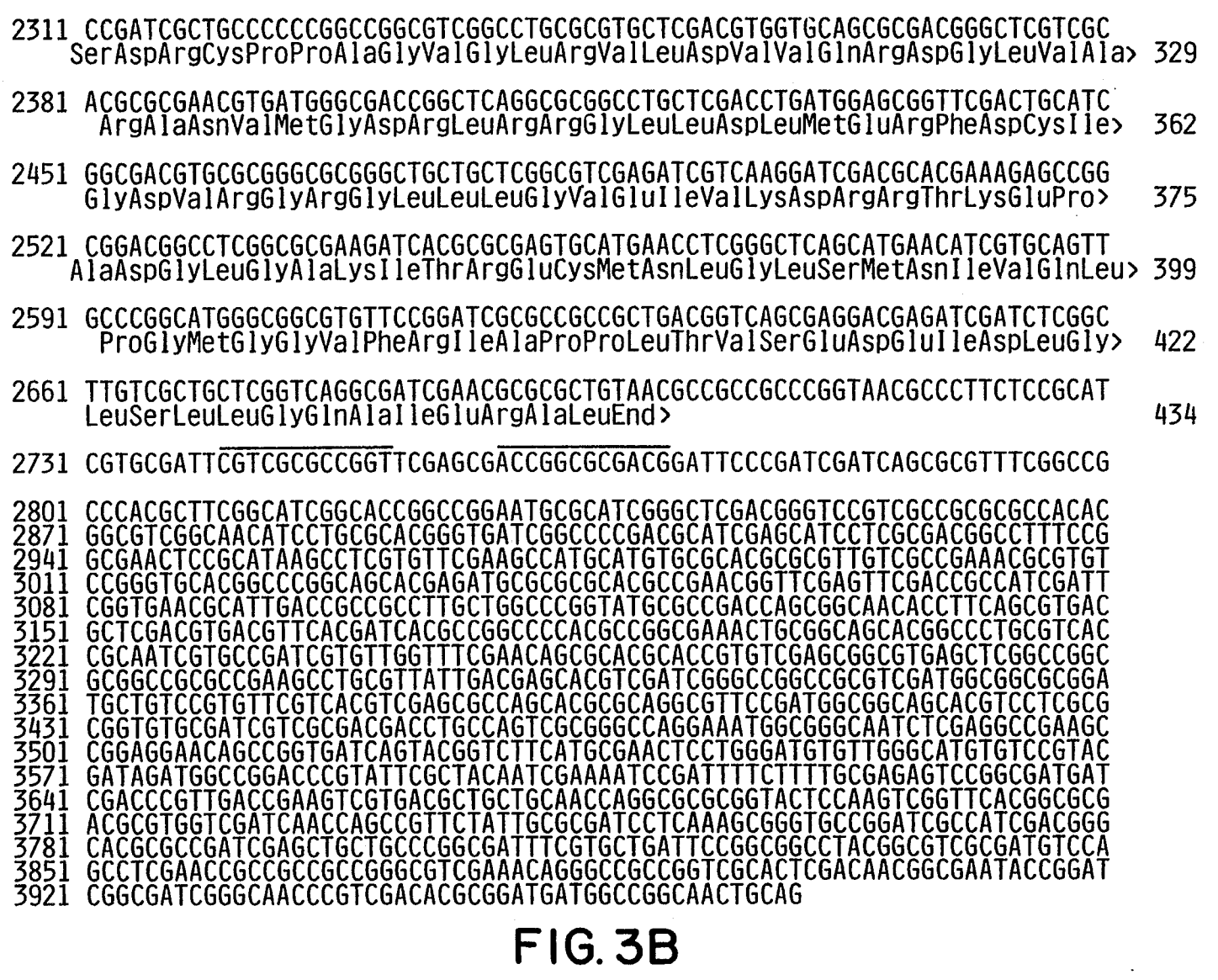

Identification of the Dialkylglycine Decarboxylase Structural Gene—The ATG initiation codon of the 1302-base dialkylglycine decarboxylase structural gene is at position 1395 of the (+)-strand of the insert (FIGS. 1-3). This ATG marks the beginning of the only large reading frame within the region of the insert that is necessary for expression of decarboxylase activity. The predicted amino acid sequence of this coding region matches the experimentally determined sequences at the amino terminus and active site.

Ahead of the structural gene, a CCGGAG sequence was found that is similar to the ribosome binding sites ahead of other bacterial genes (Min et al., 1988; Stormo et al., 1982). Also, 40 nucleotides downstream of the TAA stop codon is a 31-base GC-rich sequence with dyad symmetry that could form a 12-base stem, 7-base loop structure. The sequence immediately downstream of this dyad is not T-rich; thus, this sequence is similar to π-dependent transcription terminators in other bacterial operons (Platt, 1986).

Codon usage within the decarboxylase coding region is strongly biased toward codons with G or C in the third position: 401 out of 434 codons (92%) have G or C in the third position (Table 2).

TABLE 2

Codon Usage in the Pseudomonas cepacia Dialkylglycine Decarboxylase Gene Nucleotides 1395-2699

| | | | | | | | | | | | | |
|---|---|---|---|---|---|---|---|---|---|---|---|---|
| TTT | Phe | 0 | TCT | Ser | 0 | TAT | Tyr | 3 | TGT | Cys | 0 |
| TTC | Phe | 15 | TCC | Ser | 4 | TAC | Tyr | 9 | TGC | Cys | 6 |
| TTA | Leu | 0 | TCA | Ser | 0 | TAA | — | 1 | TGA | — | 0 |
| TTG | Leu | 2 | TCG | Ser | 10 | TAG | — | 0 | TGG | Trp | 2 |
| CTT | Leu | 0 | CCT | Pro | 0 | CAT | His | 1 | CGT | Arg | 0 |
| CTC | Leu | 27 | CCC | Pro | 5 | CAC | His | 6 | CGC | Arg | 25 |
| CTA | Leu | 0 | CCA | Pro | 1 | CAA | Gln | 0 | CGA | Arg | 1 |
| CTG | Leu | 21 | CCG | Pro | 13 | CAG | Gln | 8 | CGG | Arg | 6 |
| ATT | Ile | 1 | ACT | Thr | 0 | AAT | Asn | 0 | AGT | Ser | 1 |
| ATC | Ile | 25 | ACC | Thr | 4 | AAC | Asn | 9 | AGC | Ser | 8 |
| ATA | Ile | 0 | ACA | Thr | 0 | AAA | Lys | 2 | AGA | Arg | 0 |
| ATG | Met | 13 | ACG | Thr | 18 | AAG | Lys | 9 | AGG | Arg | 2 |
| GTT | Val | 0 | GCT | Ala | 0 | GAT | Asp | 6 | GGT | Gly | 2 |
| GTC | Val | 16 | GCC | Ala | 11 | GAC | Asp | 21 | GGC | Gly | 36 |
| GTA | Val | 0 | GCA | Ala | 5 | GAA | Glu | 8 | GGA | Gly | 2 |
| GTG | Val | 12 | GCG | Ala | 33 | GAG | Glu | 16 | GGG | Gly | 9 |

This percentage is consistent with the prediction of Bibb et al. (1984) that 88% of the third positions will have G or C in a gene having 68% G+C. Codon bias analysis was particularly helpful in identifying the reading frame of the decarboxylase structural gene in this GC-rich DNA, since the non-coding reading frames are not nearly as biased toward G and C in the third position.

The length and amino acid content of the decarboxylase polypeptide deduced from the nucleotide sequence is nearly identical with that determined by Lamartiniere et al. (1971) for the dialkylglycine decarboxylase from another Pseudomonas isolate. A sequence identity of 83% is predicted for these two proteins using Cornish-Bowden's method based on amino acid content (Cornish-Bowden, 1979). Considering the possibility of error in the amino acid determination, it is likely that the enzyme studied in this work, which is the same one studied by Sato et al. (1978), is identical with the one studied by Lamartiniere et al. (1971).

Homology Searches—The deduced amino acid sequence of the P. cepacia dialkylglycine decarboxylase was compared with the Protein Identification Resource database (Release 17) and with translations of all six reading frames of each DNA sequence in the GenBank (Release 60) and the EMBL (Release 15) databases (Henikoff and Wallace, 1988). The GenBank search located three sequences that showed significant homology to the dialkylglycine decarboxylase; the 423-amino acid translation of yeast ornithine aminotransferase mRNA (Degois. 1987), and the 439 amino acid translations of rat (Mueckler and Pitot, 1985) and human (Mitchell et al., 1988) ornithine aminotransferase mRNAs. Comparison of these sequences with the deduced dialkylglycine decarboxylase sequence using a moving 30-amino acid window (Wilbur and Lipman, 1983) gives log odds scores of 10.5, indicating a significant sequence similarity (Henikoff and Wallace, 1988). No decarboxylase sequence scored higher than 9.8 in the search procedure and alignments of several decarboxylase sequences with the dialkylglycine decarboxylase sequence showed no noteworthy similarities. Homologies with other aminotransferases were weak except near active site lysines as discussed below. The *E. coli* branched chain aminotransferase (Inoue et al., 1988) and phosphoserine aminotransferase (van del Zel et al., 1989) showed no homology with the dialkylglycine decarboxylase or ornithine aminotransferase even in active site regions.

Dialkylglycine Decarboxylase Gene Induction—The kinetics of decarboxylase induction in *E. coli* host DH5α carrying plasmid pKBD6 were studied with several amino acids that are substrates for the dialkylglycine decarboxylase and that therefore might be expected to be gene inducers. These are racemic isovaline, 2-methylamine, and D-alanine, which are decarboxylated by the enzyme, and L-alanine, which is transaminated (Bailey et al., 1970). As shown in FIG. 7, when DH5α/pKBD6 was grown in minimal media containing ammonium chloride as nitrogen source, decarboxylase specific activity was low. Addition of either 2-methylalanine or racemic isovaline caused an immediate and rapid increase in decarboxylase specific activity, approximately paralleling growth. Decarboxylase production ceased with growth and remained stable for several hours in the induced cells (data not shown). In contrast, when D- or L-alanine was added to growing cell cultures, no decarboxylase production ensued.

Induction Stereochemistry—The induction phenomenon was further investigated by surveying the inducing ability of the separate isovaline stereoisomers and 15 other structurally similar amino acids (Table 3).

boxylase specific activities 10 times the untreated control only if S-isovaline, 2-methylalanine, or L-2-aminobutanoic acid had been added to the culture medium; 1-aminocyclopentanecarboxylic acid induced an intermediate level. The other amino acids tested induced no better than the culture medium itself.

Figure 8:
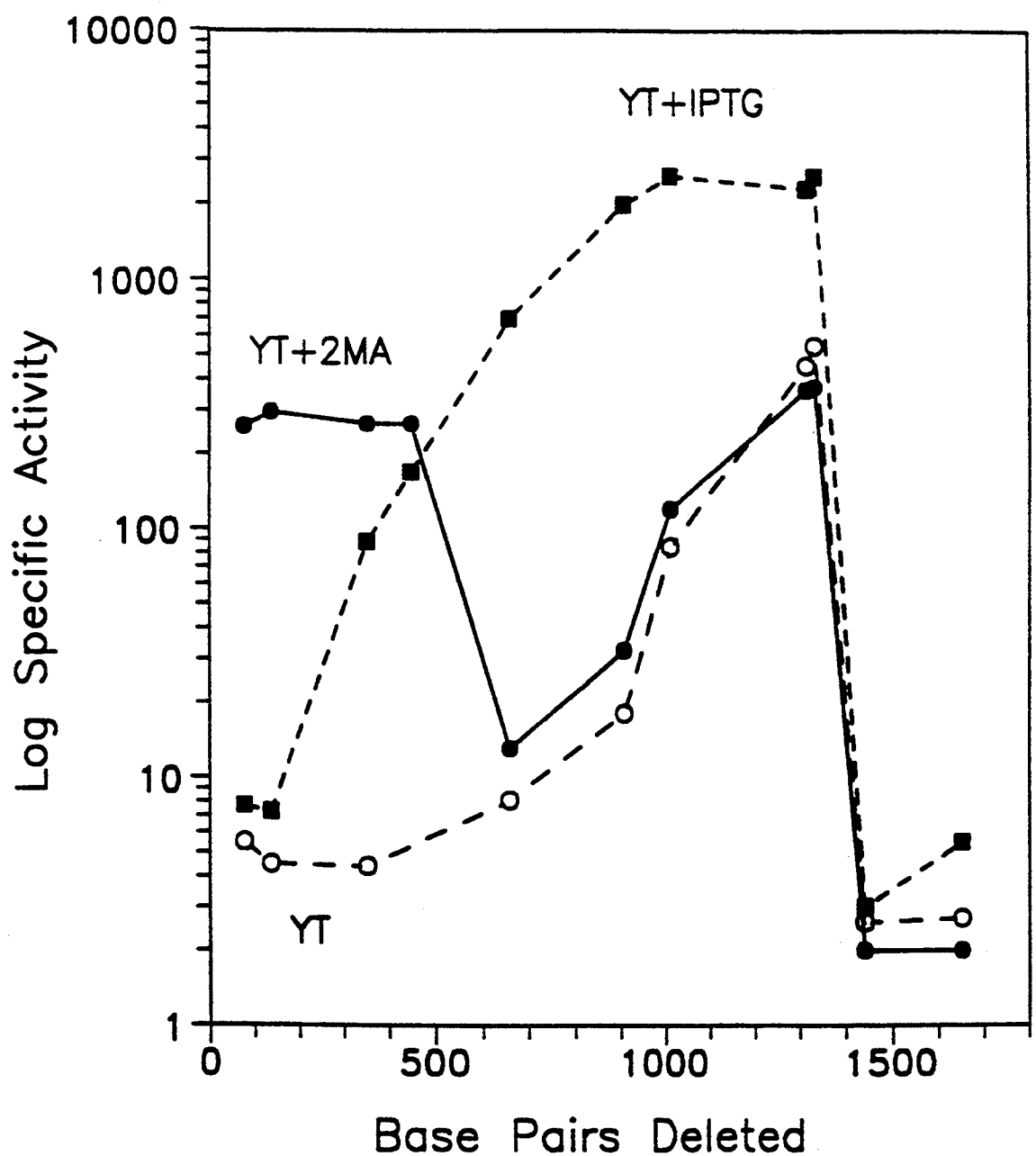
FIG. 8 shows dialkylglycine decarboxylase specific activity in extracts of E. coli JM109 carrying pGEM-7Z14 or a derivative with up to 1651 bp deleted. Cultures were grown over night in YT medium (○—○), YT plus 20 mM 2-methylalanine ( — ), or YT plus 1 mg/ml IPTG ( — ). Units of nmol h$^{-1}$ mg$^{-1}$.

The role of the upstream DNA in controlling decarboxylase gene expression was investigated by determining decarboxylase levels in *E. coli* JM109 carrying PGEM-7Z14 or one of 10 plasmids derived from it with various lengths of insert removed by exonuclease treatment. In these constructs, transcription from the vector lac promoter, which is upstream of the insert and pointing toward it, was controlled by maintaining the plasmids in host strain JM109, an overproducer of the lac repressor (Yanisch-Perron et al., 1985). FIG. 8 shows decarboxylase specific activities of the various JM109 strains grown in YT, YT plus 2-methylalanine, or YT plus IPTG. Most obviously, truncation by 1440 or 1651 bp completely prevented production of active dialkylglycine decarboxylase under all growth conditions. These deletions removed part of the decarboxylase structural gene that has been shown by sequencing to begin at 1395 of the insert. In the presence of IPTG, the strains carrying the next two larger plasmids (1332 and 1314 bp removed) produced high levels of enzyme, about 500-fold over background. When grown in untreated or 2-methylalanine-treated medium, these latter strains produced decarboxylase levels about 30-fold over background. Strains carrying the next three larger plasmids (1012, 907, and 658 bp removed) produced much less decarboxylase activity with or without 2-methylalanine, while the IPTG-induced levels in all three remained over 100 times background. Finally, in strains carrying the four largest plasmids (447, 352, 137, and 77 bp removed from the original insert), 2-methylalanine induced enzyme activities jumped back to 30 times the untreated levels, while the effect of IPTG decreased to nil.

TABLE 3

2,2-Dialkylglycine Decarboxylase Structural and Control Genes
Induction of cloned dialkylglycine decarboxylase
activity by alkyl-substituted amino acids
[C(pro-R) (pro-S) (NH$_2$) (COOH)]

| Amino Acid | pro-R | pro-S | Specific activity nmol h$^{-1}$ mg$^{-1}$ | S.D. (No. of experiments) |
|---|---|---|---|---|
| Control | | | 5.12 | 4.01 (14) |
| Glycine | H | H | 5.20 | 0.20 (2) |
| L-Alanine | H | CH$_3$ | 1.74 | 0.20 (2) |
| L-2-Aminobutanoic acid | H | CH$_2$CH$_3$ | 48.8[b] | 12.00 (4) |
| L-Norvaline | H | CH$_2$CH$_2$CH$_3$ | 4.51 | 0.08 (2) |
| L-Valine | H | CH(CH$_3$)$_2$ | 4.22 | 0.16 (2) |
| L-Isoleucine | H | CH(CH$_3$)CH$_2$CH$_3$ | 4.05 | 0.29 (2) |
| D-Alanine | CH$_3$ | H | 3.76 | 0.20 (2) |
| D-2-Aminobutanoic acid | CH$_3$CH$_2$ | H | 2.56 | 0.08 (2) |
| D-Norvaline | CH$_3$CH$_2$CH$_2$ | H | 4.21 | 0.08 (2) |
| D-Valine | (CH$_3$)$_2$CH | H | 4.59 | 0.25 (2) |
| D-Isoleucine | CH$_3$CH$_2$CH(CH$_3$) | H | 3.39 | 0.12 (2) |
| 2-Methylalanine | CH$_3$ | CH$_3$ | 58.7[b] | 22.70 (16) |
| S-Isovaline | CH$_3$ | CH$_2$CH$_3$ | 41.8[b] | 11.10 (4) |
| S-2-Methylnorvaline | CH$_3$ | CH$_2$CH$_2$CH$_3$ | 12.8 | 5.95 (4) |
| R-Isovaline | CH$_3$CH$_2$ | CH$_3$ | 6.45 | 1.45 (4) |
| R-2-Methylnorvaline | CH$_3$CH$_2$CH$_2$ | CH$_3$ | 5.45 | 1.20 (4) |
| 1-Aminocyclopentane carboxylic acid | CH$_2$CH$_2$ | CH$_2$CH$_2$ | 16.5[b] | 10.70 (4) |

[a]For duplicate experiments (n = 2), the average deviation is given.
[b]Greater than control at the 99% confidence level by the Mann-Whitney test.

JM109/pGEM7Z14 was grown overnight in YT-ampicillin plus 20 mM amino acid, then cell sonicate supernatants were assayed for protein and dialkylglycine decarboxylase activity. The assays showed decar- Alignment of the deduced amino acid sequences of *P. cepacia* 2,2-dialkylglycine decarboxylase and rat ornithine aminotransferase is shown in FIG. 9. The overall homology between these sequences is 24%; however, most of the homologous segments are in the 230-amino acid carboxyl termini: in this region, 56% of the residues are homologous. This region of ornithine aminotransferase is homologous with the carboxyl terminus of aspartate aminotransferase (Mueckler and Pitot, 1985) that, as shown by X-ray crystallography, contains the cofactor binding domain (Ford et al., 1980: Graf-Hausner et al., 1983: Borisov et al., 1980; Kagamiyama et al., 1980). Thus, although direct alignment of dialkylglycine decarboxylase and aspartate aminotransferase sequences shows little sequence similarity, it is likely that the carboxyl termini of both the decarboxylase and ornithine aminotransferase form the major part of pyridoxal 5'-phosphate binding pockets.

The yeast ornithine aminotransferase sequence shows a 14% homology with the dialkylglycine decarboxylase sequence (and is only 50% homologous with the rat or human sequences) (Degols, 1987). The regions of major similarity are around the active site lysines.

The optimum overall alignment of the dialkylglycine decarboxylase and rat ornithine aminotransferase sequences (FIG. 9) aligns only one pair of lysines, K272 of the former and K292 on the latter. Simmaco et al. (1986) have shown that K292 is at the active site of ornithine aminotransferase, while we have shown that K272 is the active site lysine in the dialkylglycine decarboxylase. The amino acid sequences on either side of these lysines are also conserved in several other aminotransferases as shown in FIG. 10. One sequence in particular seems strongly conserved besides the active site lysines: this is a DIVL box six to nine amino acids on the amino side of the lysines. The crystal structure of the chicken mitochondrial AAT shows these residues in one strand of the seven-strand pleated sheet that forms the back wall of the cofactor binding site (Jansonius et al., 1985).

A surprising finding was the lack of an active site histidine-lysine pair in the 2,2-dialkylglycine decarboxylase. All known procaryotic pyridoxal phosphate-dependent decarboxylases, including $E.$ $coli$ arginine, lysine, ornithine, and glutamate decarboxylases (Tanase et al., 1979) and two eucaryotic decarboxylases, the pig kidney L-$\beta$-3,4-dihydroxyphenylalanine decarboxylase (Tanase et al., 1979) and $Morganella$ $morganii$ histidine decarboxylase (Hayashi et al., 1979), have such a sequence at the active site. The $M.$ $morganii$ histidine decarboxylase site-directed mutagenesis studies suggest a hydrogen-bonding role for the histidine next to the active site lysine that can be partially assumed by glutamine (Vaaler and Snell, 1989). Sato et al. (1978) found that diethyl pyrocarbonate modifies one of seven histidines of the dialkylglycine decarboxylase, inhibiting the decarboxylation reaction selectively. Thus, this enzyme probably still requires the histidine catalyst, but it is elsewhere in the active site instead of adjacent to lysine.

Maximum levels of dialkylglycine decarboxylase expression from these plasmids in $E.$ $coli$ was similar, to that in 2-methylalanine-induced $P.$ $cepacia$ (Keller and O'Leary, 1979; Lamartiniere et al., 1971). Steps were taken to maximize expression of the cloned decarboxylase gene by orienting the gene downstream of the strong inducible lac promoter and removing (in pGEM-7Z14/8b) all but 76 base pairs (bp) of cloned DNA upstream of the structural gene. We ascribe the low expression levels to translational barriers. Slow translation could be caused by several arginine codons, namely CGA, AGG, and CGG that are associated with genes weakly expressed in $E.$ $coli$ (Bulmer, 1988). These codons occur, respectively, one, twice, and six times in the decarboxylase structural gene. Another translational barrier could be a ribosome binding sequence that is non-optimal for $E.$ $coli.$ Recent studies have shown that in $E.$ $coli$ the mRNA ribosome binding site occupies positions -13 to -8 relative to the initiation codon and has a consensus sequence of AAGGAG (Min et al., 1988; Stormo et al., 1982) whereas that site ahead of the dialkylglycine decarboxylase gene has the sequence CCGGAG.

Control of decarboxylase gene expression is probably exercised by an upstream repressor gene. The repressor gene was located by decarboxylase gene induction experiments with strains carrying plasmids with the $Pseudomonas$ DNA insert truncated by various amounts (FIG. 8). pGEM-7Z14 and the next three smaller plasmids (from 77 to 447 bp of the insert removed) all show complete repression of decarboxylase gene expression in the absence of 2-methylalanine and complete derepression by 2-methylalanine. Thus, the control system is intact and identical in these four plasmids. Truncation by another 211 bp (658 bp total) results in a dramatic lowering of decarboxylase expression to the background level even in the presence of 2-methylalanine. This 658 bp shortening removes 10 codons from the 3' end of the repressor coding region, with the removed DNA probably encoding all or part of a 2-methylalanine-binding domain at the repressor's carboxyl terminus. The portion of the gene coding for the repressor's DNA binding domain is left untouched in this plasmid and is likely still transcribed from a promoter at the other end. The resulting shortened or modified protein could still bind to an operator sequence, but would no longer be affected by 2-methylalanine. Truncation by 907 or 1012 bp results in partial repression of decarboxylase expression, which in partial repression of decarboxylase expression, which probably is due to synthesis of portions of the DNA binding domain that retain some affinity for the operator site. Finally, removal of 1314 or 1332 bp abolishes all repression by removing all or most of the DNA coding for the DNA binding domain, but still leaves a promoter on both plasmids just ahead of the decarboxylase gene. Expression levels from these latter plasmids are identical with the 2-methylalanine induced levels observed with the larger plasmids, as expected if RNA polymerase had unrestricted access to the $Pseudomonas$ dialkylglycine decarboxylase promoter. While the results indicate that the decarboxylase promoter is within 75 nucleotides of the structural gene, its precise location and sequence have not been established; there are no clear sequence homologies with known $Pseudomonas$ or $E.$ $coli$ promoters.

IPTG-induced decarboxylase gene expression was greater the closer the lac promoter was to the decarboxylase gene (FIG. 8). In pGEM-7Z14 and the next smallest plasmid, transcription from the lac promoter is weak enough that it can be completely blocked by the dialkylglycine decarboxylase repressor. As the intervening DNA is shortened, which may remove transcription-terminating sequences, repressor binding only partially blocks read-through from the lac promoter. Expression was highest when the lac-decarboxylase separation was 500 bp or fewer.

The stereochemical characteristics of the amino acid binding site responsible for modulating DNA binding are apparent in Table 3.

These data suggest that the amino acid binding domain of the repressor incorporates sites for each $\alpha$-alkyl group, besides ionic sites for the α-NH$_3$+ and/or the α-COO−. One alkyl group binding site, the pro-R one, interacts with a pro-r methyl of the substrate, but is too small to accept larger alkyl groups. The other site, the pro-S one, binds either a pro-S methyl or ethyl, but nothing larger. Additionally, since neither glycine nor D- or L-alanine induce, an inducer of this gene must contain at least two methylene groups on the α substituents; for example, two methyls as in 2-methylalanine or an ethyl on one side and a hydrogen on the other side as in 2-aminobutanoic acid. These groups would provide a minimum hydrophobic interaction energy with the repressor binding site. Only 2-methylalanine, S-isovaline, and L-2-amino-butanoic acid satisfy these criteria. 1-Aminocyclopentanecarboxylic acid is a weak inducer, perhaps fitting portions of its ring β-methylenes into both alkyl group binding sites.

The stereospecificity of dialkylglycine decarboxylase gene induction by isovaline is opposite that of the decarboxylase. Aaslestad et al. (1968) reported that the Michaelis constants of the R and S isomers are 1.0 mM and 25 mM, respectively. And relative $V_{max}/K_m$ values, which correlate with affinity of the enzyme for the transition state of the decarboxylation reaction are 7.9 and 1.0 for R and S isomers, respectively. Sterically, the enzyme is more flexible than the repressor: it decarboxylates several amino acids that do not induce decarboxylase gene expression, including D-alanine (Bailey et al., 1970), racemic 2-methylnorvaline (Tahara et al., 1969), and 1-aminocyclo-pentanecarboxylic acid. Also, several other amino acids are decarboxylase substrates but have not been tested for gene induction, including 1-aminocyclobutanecarboxylic acid, 2-amino-2-ethylbutanoic acid, and racemic 2-methylserine.

Another surprising stereochemical consequence of these results is that the only known biological sources of isovaline, the so-called peptaibol antibiotics of soil fungi, contain R-isovaline and not S-isovaline (Bosch et al., 1982). Thus, it is unlikely that the dialkylglycine decarboxylase genes studied here have evolved specifically to metabolize the isovaline occurring in peptide antibiotics. These genes and gene products more likely evolved to metabolize 2-methylalanine, which is achiral and is present in greater amounts than isovaline in the peptaibol antibiotics (Schmitt and Jung, 1985).

These results cannot be explained by operation of a positive control system, since decarboxylase expression returns to depressed levels once all or most of the control gene has been deleted. Nor is it likely that decarboxylase gene expression is controlled in trans from *E. coli* DNA, since (i) the host cannot metabolize dialkylglycines and therefore probably does not have receptors that bind both the dialkylglycines and certain sequences of exogenous DNA and (ii) de-repression is stereospecific and consistent, making the action of a nonspecific DNA binding protein unlikely. Control is not exercised by DNA downstream of the cloned dialkylglycine decarboxylase gene, since plasmids truncated in that region still show the repression-derepression properties of the intact plasmid (data not shown). Finally, the rapid induction kinetics (FIG. 7) indicate that a direct process such as repressor release turns on decarboxylase gene expression, rather than a multiple step process requiring synthesis of other proteins.

This study has outlined evidence for the existence of a new repressor that is regulated by three closely related alkyl-substituted amino acids. While the function of this system closely parallels other classical repressor-gene pairs, the predicted sequence suggests that a unique protein structure is involved. It is also shown that the *P. cepacia* dialkyl glycine decarboxylase has a unique structure that is not homologous to known amino acid decarboxylase sequences, but instead is closely related to the eucaryotic ornithine aminotransferases and other aminotransferases. Thus, it may be more properly described as a decarboxylating aminotransferase rather than an aminotransferring decarboxylase. It is likely that the in vivo function of this enzyme in *Pseudomonas* is to decarboxylate dialkylglycines, since enzyme production in *Pseudomonas* is stimulated by 2-methylalanine (Aaslestad and Larson, 1964).

In summary, a 3969 base pair PstI-PstI fragment of *Pseudomonas cepacia* DNA containing the gene for the pyridoxal 5'-phosphate dependent 2,2-dialkylglycine decarboxylase (pyruvate) (EC 4.1.1.64) was cloned in *Escherichia coli*. The insert was sequenced by the dideoxy method using nested deletions from both ends, revealing a central 1302 base pair region that codes for the decarboxylase subunit. The recombinant enzyme was expressed in *E. coli*, purified to homogeneity, and sequenced at the amino terminus. Also, a cofactor-labeled active site peptide was sequenced. The carboxyl terminus of the deduced amino acid sequence is homologous with the carboxyl terminus of mammalian ornithine aminotransferase; the active site sequence is similar to the active site sequences of several other aminotransferases. No homologies with known decarboxylase sequences could be found. Expression of the decarboxylase gene is negatively controlled by a 687 nucleotide sequence upstream of and diverging from the structural gene. Expression is induced by S-isovaline, 2-methylalanine, and D-2-aminobutanoic acid, but not by glycine, D-or L-alanine, L-2-aminobutanoic acid, R-isovaline, or other alkyl amino acids.

Additional modifications will readily occur to those skilled in the art. One such modification would be to modify the expression vector making it useful for the regulated expression of other genes. Such a recombinant expression vector comprises a bacterial promoter, the nucleotide sequence of the invention coding for the repressor protein, a nucleotide sequence coding for a ribosome binding site, and a restriction endonuclease cleavage site for insertion of a foreign gene. In this vector, the promoter and the nucleotide sequence encoding the repressor protein are arranged for read through transcription by a polymerase, and the restriction endonuclease cleavage site is downstream from the ribosome binding site. As discussed, supra, such an expression system is derepressed by an inducer. The inducers of choice are S-isovaline, 2-methylalanine, L-2-aminobutanoic acid, or 1-aminocyclopentane-carboxylic acid. It is also possible to add a secondary prokaryotic promoter upstream from the gene to be expressed. A preferred secondary promoter would be the lac promoter. In this case the lac promoter is derepressed by IPTG. Thus, it is possible to control the expression of the recombinant protein by inducers for the indigenous (i.e. decarboxylase) promoter, the lac promoter, or both.

dgd Expression System

Specific embodiments of this invention relate to vectors comprising the dgd operators O1 and O2 as depicted in FIG. 17 (O1: SEQ ID NO: 29; O2: SEQ ID NO: 30). In other embodiments of this invention O1 and O2 may be substituted with equivalent operators exhibiting substantially the same nucleotide sequence of O1 and O2 and able to bind 2,2-dialkylglycine decarboxylase repressor. Operators O1 and O2 are positioned on the vector to permit cooperative binding of repressor protein, or an oligomer thereof, to O1 and O2 in the absence of an inducer. Preferably the distance between O1 and O2 is sufficient to form a loop between O1 and O2 that is mediated by the 2,2-dialkylglycine decarboxylase repressor. Smaller loops may be formed using accessory proteins such as CAP-BP. In specific embodiments of this invention the distance between O1 and O2 as it exists in the natural dgd expression system is conserved. In especially preferred embodiments O1 and O2 are separated by about 500 bp.

In specific embodiments a vector of this invention also comprises the dgdR gene. In these embodiments the dgdR gene is positioned within the vector so that O2, which is found within the coding region of the dgdR gene, and O1 can cooperatively bind repressor protein, or an oligomer thereof, in the absence of an inducer.

Several embodiments of this invention relate to a vector comprising a heterologous promoter. The choice of a suitable promoter will be governed by the choice of a host cell to be transformed with the vector. The promoter chosen can be constitutive or regulatable. When $E.$ $coli$ is used as a host cell examples of suitable promoters would include lac, trp, or tac. When a eukaryotic host cell is used examples of suitable promoters would be HSK TK, CMV, and Ad2 MLP. In other embodiments of this invention the native dgdA promoter is included in the vector together with or in place of the heterologous promoter.

The promoter is located between the two operators and is positioned to provide an operable linkage to a structural gene to be expressed. Moreover, the promoter should be sufficiently distant from O2 so that RNA polymerase binding is not prevented. In preferred embodiments of this invention the promoter is more than 100 bp from O2.

In addition to a promoter the vector may also comprise other control sequences that modulate expression. For example, a sequence encoding a ribosome binding site is present within the region surrounding the promoter. In embodiments of this invention the ribosome binding site is encoded by the sequence located immediately upstream of the dgdA structural gene and identified in FIG. 3 (SEQ. ID NO: 8). However, other equivalent ribosome binding sites can be used.

The vectors of this invention can be constructed using molecular cloning techniques well known to the person of ordinary skill in art. For example, the operators of this invention may be obtained by synthetic DNA synthesis. Polymerase chain reaction (PCR) can also be employed to obtain DNA comprising various elements of the vectors.

By way of example, a suitable vector can be assembled using PCR with customized primers. A first DNA sequence comprising the dgdR gene, operator O2, and the natural promoter of dgdA, but not the dgdA ribosome binding site which lies 10 bp ahead of dgdA, may be obtained by amplifying a DNA sequence containing these elements. Such a DNA sequence is found in any plasmid containing the dgd expression system; for example, pGEM7Z14. In specific embodiments of this invention, the first DNA sequence is amplified using a left PCR primer that includes a recognition site for a blunt end-cutting restriction enzyme, such as the SmaI site CCCGGG. The right PCR primer for this first DNA sequence includes the recognition site for an enzyme that makes a compatible end that is uncuttable after annealing. For example, C'TCGAG, the recognition site for XhoI, may be included in the primer. This would permit ligation to a cohesive end obtained by cutting with SalI, G'TCGAC.

A second DNA sequence comprises O1. A 200 bp region around O1, which is found within the dgdA gene, can be amplified using a left PCR primer comprising a T'GATCA BclI site and a right PCR primer with a recognition site for a blunt end-cutting restriction enzyme.

A third DNA sequence comprising a suitable promoter is prepared using PCR or other standard techniques. In specific embodiments of this invention, this fragment contains a SalI site at its 5' end and a BamHI site (G'GATCC) at its 3' end and is about 200 bp in length.

The DNA fragments are cut with the appropriate restriction enzymes, are annealed and are ligated to create a blunt-ended cassette about 1,300 bp long with O1 on the right, the dgdR repressor gene including O2 on the left, and a promoter in the middle. This cassette can then be inserted into a blunt ended gap ahead of any structural gene cloned in a suitable expression vector. The expression vector is used to transform suitable host cells to direct the synthesis of the structural gene.

This invention further relates to a regulated process of producing a heterologous protein using a recombinant vector of this invention. In embodiments of this invention, the process comprises the following steps:
providing a host cell transformed with a vector of the instant invention encoding a heterologous sequence to be expressed;
providing 2,2-dialkylglycine decarboxylase repressor protein in the host cell at a concentration sufficient to bind to O1 and O2;
inducing expression of heterologous protein; and
isolating the expressed protein.

In specific embodiments of this invention, the repressor protein is provided by including the 2,2-dialkylglycine decarboxylase repressor gene in the vector and expressing the repressor gene in the host cell. Inducing expression of the heterologous protein is carried out in accordance with this invention by dissociating repressor from operator O1. In specific embodiments of this invention, induction is carried out by adding a suitable inducer of the 2,2-dialkylglycine decarboxylase expression system such as S-isovaline, 2-methylalanine, L-2-amino-butanoic acid, and 1-aminocyclopentanecarboxylic acid. The use of 2-methylalanine as an inducer is particularly favored. 2-methylalanine is extremely rare in most living systems, it is non-toxic, and it is transported but not metabolized by most prokaryotic and eukaryotic cells.

The repressor protein and the nucleotide sequence encoding the repressor protein of the invention are in concentrated form. By this it is meant that the repressor protein and nucleotide sequence are found in higher levels in the expression system of the invention than in $Pseudomonas$ $cepacia$ cells in which they naturally occur. The repressor protein and the nucleotide sequence encoding the protein can be obtained in a purified form according to this invention. By this it is meant that the repressor protein and the nucleotide sequence are free of other proteins, nucleotide sequences, and other cell components of *Pseudomonas cepacia* strains in which they naturally occur.

A detailed description of the experimental procedures that can be employed in practicing this invention follows.

Experimental Procedures

Bacterial Strains and Media—For transformations with recombinant plasmids the *E. coli* strains used were MM294 (K-12, endA1, thi-1, hsdR17, supE44, λ−) , DH5α (F−, endA1, hsdR17(r−$_k$ m+$_k$), supE44, thi-1, k-, recA1, gyrA96, relA1, φ80dlacSΔM15], and JM109 (recA1, Δlac-pro, endA1, gyrA96, thi-1, hsdR17, supE44, [F':traD36, proAB+, lacI$^q$-ZΔM15]). A *Pseudomonas cepacia* strain obtained from Dr. M. Honma of the Department of Biochemistry, Hokkaido University, was the source of chromosomal DNA. This bacterial culture was clearly identified as *Pseudomonas cepacia* by the API 20E system (identification number 5-206-027-53) and other tests; it has been deposited with the ATCC. *E. coli* strains were grown on LB medium or agar (Maniatis et al., 1982) containing ampicillin or carbenicillin at 50–100 mg/L or tetracycline at 12 mg/L. Selection and growth of clones coding for dialkylglycine decarboxylase was carried out on M9 minimal medium or agar (Maniatis et al., 1982) containing 1 g/L of ammonium chloride or 2-methylalanine as nitrogen source and the appropriate antibiotic. *P. cepacia* was grown on Difco nutrient broth (or agar) and minimal medium (or agar ((9.5 g/L $K_2HPO_4.3H_2O$, 3 g/L $KH_2PO_4$, 40 g/L glycerol, 87 mg/L $K_2SO_4$, 36 mg/L $MgCl_2.6H_2O$, and 2.8 mg/L $FeCl_3.H_2O$ with either 1 g/L $NH_4Cl$ or 2 g/L 2-methylalanine).

Recombinant DNA Techniques—Methods were as described by Maniatis et al. (1982). Restriction enzymes and T4 DNA ligase were obtained from Bethesda Research Laboratories, IBI or Promega and were used as recommended by the supplier. Competent cells were prepared by the calcium chloride or rubidium chloride/calcium chloride methods. (Golub, 1988; Maniatis et al. 1982).

Cloning and Subcloning of *Pseudomonas* DNA—Vector pBR322 was obtained in the *E. coli* strain MM294 as a gift from Dr. Milton Gordon; pUC19 and pGEM-7Zf(+) DNAs were obtained from Bethesda Research Laboratories and Promega Corporation, respectively. Chromosomal DNA was isolated from *Pseudomonas cepacia*, cut with PstI, and ligated to PstI-cut pBR322 DNA (K. B. Baurick, M. S. Thesis, University of Alaska Fairbanks, 1987). A ligation mixture containing 1 μg each of vector and insert was used to transform 200 μL of competent *E. coli* MM294, which was then transferred to 20 ml of LB medium. After 90 min. at 37° C. 50 μl aliquots of a $10^{-1}$ dilution were plated on each of 22 100-mm LB/tetracycline plates. After 12h replica transfers were made to LB/carbenicillin and M9/2-methylalanine plates. After 60 h 5 adjacent colonies were observed on one M9/2-methylalanine plate. One colony was chosen for further study. Replating on appropriate media indicated a stable tet$^r$carb$^s$2MA+- phenotype. Transfer of the 4.0 kbp PstI-PstI fragment or related fragments to other vectors was carried out by ligation of appropriate restriction digests to the restricted vector, followed by host transformation, isolation of mini-prep plasmid DNA (Holmes and Quigley, 1981) and identification of the desired construct by restriction analysis.

Construction of Unidirectional Deletions—Deletions were made from either pUC19C7, pUC19H1, or pGEM-7Z14 by the method of Henikoff (Henikoff, 1984) using reagents and recommended procedures in the Promega Erasabase kit. Plasmid DNA for the deletion reactions was purified from minipreparations (Holmes and Quigley, 1981). Leftward deletions from the right end of the 4.0 kbp insert (FIG. 1) were made in both pUC19C7 and pUC19H1 by initially restricting with KpnI and XbaI within the multiple cloning site. These enzymes were chosen because they do not cut within the *Pseudomonas* DNA insert and because they create ends which are respectively exonuclease III-resistant and exonuclease III-sensitive. The double-cut DNA was then digested with exonuclease III, aliquots were quenched at timed intervals, and the blunted ends ligated. The trimmed plasmids were isolated from hosts transformed with each ligation mixture and were characterized by restriction analysis. Rightward deletions from the left end of the insert in pUC19C7 (FIG. 1) could not be made because the appropriate pair of restriction sites are not available there. Thus, pGEM-7Z14 was constructed by transfer of a XbaI-EcoRI fragment from pUC19C7 to pGEM-7Zf(+); the new construct, pGEM-7Z14, contains three unique sites on the left side which create exonuclease III-resistant and exonuclease III-sensitive ends. This plasmid was cut with EcoRI and KpnI or with EcoRI and BstXI to generate the exonuclease III substrate, and then was treated as above.

DNA Sequencing—Sequence was obtained by the modified Sanger method as overlapping 100 to 300-base segments on both+ and− strands using reagents and protocols recommended by suppliers of Sequenase (U.S. Biochemicals) or Klenow enzyme (Boehringer). Template DNA was prepared by alkaline denaturation of miniprep DNA (Kraft, et al., 1988). Primers were synthesized by Synthetic Genetics, Inc., La Jolla, Calif. on an Applied Biosystems, Inc. Model 380 Synthesizer and were used without further purification. For (−)-strand sequencing (top strand template in FIG. 1) of deletions derived from pUC19C7 or pUC19H1, the 20mer 5'-GCTGCAAGGCGATTAAGTTG-3'[SEQ ID NO: 1] was used; for (+)-strand sequencing (bottom strand template in FIG. 1) of deletions derived from pGEM-7Z14, the 20mers 5'-AGCTCTCCGGATC-CAACCTT-3' [SEQ ID NO: 2] or 5'-ATTTCACACAGGAAACAGCT-3' [SEQ ID NO: 3] were used. Most reactions were run using 7-deaza-dGTP in place of dGTP to minimize compression artifacts during electrophoresis. Reactions were run with $^{35}$S-dATP (New England Nuclear, 5 μCi per labeling reaction), electrophoresed on 6% 40-cm acrylamide gels (BioRad) bonded to the outer plate of the electrophoresis assembly with 3-(trimethoxysilyl)propyl methacrylate (Aldrich), fixed 15 min. in 5% methanol/5% acetic acid, dried 30 min at 100° C., then autoradiographed overnight with Kodak XAR-5 film. Autoradiograms were read manually. Either Genepro (Riverside Scientific Enterprises, Seattle) or Pustell (International Biotechnology, Inc., New Haven) software was used for sequence analysis.

Radiochemical Dialkylglycine Decarboxylase Assay—Dialkylglycine decarboxylase activity was measured under zero-order conditions essentially as described (Dinwoodie and Boeker, 1979). Assay reactions contained 500 μL of protein solution (100 mM MOPS[1], (MOPS=3-(N-morphalino)propanesulfonic acid), 25 mM KCl, 0.05 mM PLP, (PLP=pyridoxal 5'-phosphate), pH 7.00 or 30 mM Tris, 40 mM KCl, 0.05 mM PLP pH 7.90) plus 0.045 mL of substrate solution (245 mM 2-methylalanine, 62 mM sodium pyruvate, containing 0.25 μCi [1-$^{14}$C]2-methylalanine)- Assays were carried out in stoppered 12×220 mm test tubes containing a folded 10×25 mm piece of filter paper soaked with 24 μL of 2:1 ethanolamine/2-ethoxyethanol- After incubation at room temperature (25° C.) for one or two hours, the reaction was quenched with 200 μL of 50% trichloroacetic acid, $^{14}CO_2$ was collected for one hour, and the filter paper was counted in 10 mL of Beckman Ready Safe cocktail. One unit is defined as the amount of activity required to produce 1 nanomole of $CO_2$ per min. at 25° C.

Dialkylglycine Decarboxylase Purification—In a typical preparation four 400-mL cultures of *E. coli* JM109[pGEM-7Z14/8b] (LB containing 100 μg/mL carbenicillin) were grown with shaking at 37° C. until $A_{600}$=4. IPTG (final concentration=20 μg/mL) was added at $A_{600}$=0.9. The cells were cooled on ice, collected by centrifugation, resuspended in 40 mL buffer (30 mM Tris, 40 mM KCl, 500 mM ammonium sulfate, and 0.02 mM PLP), sonicated 3×1 min at 0° C., treated with 2 mg phenylmethylsulfonyl fluoride, and centrifuged for 20 min. at 14,000× g. The clarified extract was passed over at 1.5×5.1 cm column of butyl TSK (Toya Soda) (Shin et al., 1984) equilibrated with the same buffer. The column was washed with 50 mL of the same buffer then eluted with a 200-mL linear gradient to 30 mM Tris, 40 mM KCl, 0.02 mM PLP, pH 7.90. The active fractions (50-100 mL) were concentrated by ammonium sulfate precipitation, desalted on a small BioGel P-6 column (30 mM Tris, 40 KCl pH 7.90), and chromatographed in portions on a 8.0×75 mm DEAE 5-PW column eluted with a linear 40 to 500 mM KCl gradient (1 mL/min, 35 min.). The FPLC (fast protein liquid chromatography) active fractions (22-23 mL) were combined, concentrated with an Amicon centricon-30, and finally chromatographed on a Waters 300SW size exclusion column (10×300 mm, 0.8 mL/min.). The fraction under the major peak eluting at 8.9 min. was concentrated as above.

[4'-$^3$H] Pyridoxal 5'-Phosphate—The labeled cofactor was prepared as described (Tamura and Rakov, 1986; Koga and Cross, 1982; Raibaud and Goldberg, 1974) by reduction of 25 mg PLP with [$^3$H]NaBH$_4$ (25 mCi, 1400 mCi/mmol, in 0.30 mL 0.5 M NaHCO$_3$ at 0° C.), oxidation with fresh MnO$_2$, and chromatography on a 1.5×28 cm Dowex-50 column (acetate form) to give material with a specific radioactivity of 260 mCi/mmol.

Active Site Labeling—Apodecarboxylase was made by incubating 1 mg of purified dialkylglycine decarboxylase with 2-methylalanine (40 mM plus 50 mM potassium phosphate pH 7.90, 50 mM KCl, and 0.020 mM PLP in a total volume 2.0 mL). After 5 h, the UV spectrum had changed from one of the characteristic of PLP ($\lambda_{max}$410,275 nm) to one characteristic of pyridoxamine 5'-phosphate ($\lambda_{max}$320 nm). The reaction was desalted on a 1×16 cm BioGel P6 column (50 mM potassium phosphate plus 50 mM KCl pH 7.90), reduced to 0.50 mL with a Centricon-30, and was treated with 0.20 mL [$^3$H]PLP (1.5 mM). A 3-mg portion of NaBH$_4$ was added and after 1 h the reaction was desalted on a Bio-Gel P6 column (1×16 cm, 50 mM Tris pH 7.8). Finally, the protein-containing fractions were concentrated to 0.70 mL using a Centricon-30.

Tryptic Peptide Mapping—The tritium-labeled and reduced decarboxylase (1 mg in 0.70 mL) was heated to 100° C. for 4 min, then 10 μl of trypsin (Sigma Type XI, DPCC-treated, 4 mg/mL in 50 mM Tris pH 7.5) was added and the reaction was shaken at 37° C. for 3 h; another 10 μl portion was added and the incubation was continued for 2 h. The cooled reaction was filtered through a 0.5-micron filter, then was injected (1 mL injection loop) onto a Vydac C-4 HPLC column (4.5×250 mm equilibrated with 0.12% aqueous trifluoroacetic acid and then eluted at 1 mL/min with a 120 min 0 to 40% acetonitrile, 0.12% trifluoroacetic acid gradient. Absorbance peaks were collected by hand and 50 μL aliquots of each were counted in 5 mL Beckman Ready Safe cocktail. The fraction containing the most radioactivity was rechromatographed under the same conditions and the radioactive fraction (which eluted at the same position) was lyophilized.

Protein Sequencing—A 10 μg sample of purified decarboxylase was desalted on a small BioGel P-6 column equilibrated with 1 mM ammonium acetate, then was lyophilized overnight. The protein was sequenced at the Brigham Women's Hospital of Harvard Medical School, Boston, Mass. The sample was dissolved in 100 μL of deionized water and was bound to a sample disk of an Applied Biosystems Inc. 470A automated protein sequencer. Twenty cycles were carried out with on-line PTH analyses. The labeled peptide was sequenced in the same manner in the Oncology Research Center Protein Sequencing Laboratory of the Bowman Gray School of Medicine in Winston-Salem, N.C. Sixty percent of each sequencer fraction was counted by liquid scintillation.

NMR Spectroscopy—$^1$H-NMR spectra were obtained on a Varian EM-360 spectrometer. $^{13}$C-NMR were obtained on a JEOL FX90Q spectrometer.

Racemic Dialkylglycines—Racemic isovaline and 2-methylnorvaline were prepared by Strecker synthesis (Greenstein and Winitz, 1961) from butanone or 2-pentanone, respectively, and were purified by cation exchange chromatography on Dowex-50 followed by recrystallization from water-acetone, R,S-2-Methylnorvaline: sublimes 265°-270° C.; $^1$H-NMR (D$_2$O):0.86δ (t,3H), 1.4 (s,3H), 0.9-1.9 (m,4H); $^{13}$CNMR (D$_2$O): 60δ(q), 64(t), 70(q), 87(t), 109(s), 224(s).

All other amino acids were obtained from Sigma Chem. Co.

Racemic N-Chloroacetyl Amides—These were prepared by reaction of the racemic amino acid with chloroacetyl chloride (1.5 equivalents) in a stirred aqueous solution at 0° C. maintained at pH>10 by addition of 2 M sodium hydroxide. Amide was recovered by filtration of the acidified reaction mixture and was recrystallized from water. N-Chloroacetyl-R,S-isovaline: mp 161°-162° C.; $^1$H-NMR (d$_6$-DMSO):0.78δ (t,3H), 1.35 (s,3H), 1.80 (q,2H), 4.1 (s,2H), 8.1 (s,1H). N-Chloroacetyl-R,S-2-methylnorvaline: mp 166°-166.5° C.; $^1$H-NMR (d$_6$-DMSO): 1.06δ (t,3H), 1.5 (s,3H), 1.2-2.2 (m,4H), 4.3 (s,2H, 9.4 (s,1H).

S- and R-Dialkylglycines—The amino acid stereoisomers were prepared by partial enzymatic hydrolysis (Baker et al., 1952; Bosch et al., 1982) of the racemic N-chloroacetyl derivatives. Hydrolysis was carried out on the ammonium salt of each amide (0.2 M, pH 7.5, 37° C.) by 3 mg/mL hog kidney aminoacylase (Sigma grade I). The reaction progress was followed by $^1$H-NMR spectroscopy. Integration of the chloroacetyl methylene singlets (amide; 4.36δ; chloroacetate: 4.26δ)

showed that the hydrolyses proceeded to 50% completion after 6–12 h and then stopped. The S isomer released by enzymatic hydrolysis was isolated by precipitating protein with 5% v/v trifluoroacetic acid and centrifuging, evaporating the supernatant, and eluting from Dowex-50 (H form). The R isomer was produced by hydrolyzing amide unretained by the initial Dowex-50 chromatography (2M HCl, 5 h at reflux), neutralizing with base, and again eluting from Dowex-50 (H form).

Induction of Dialkylglycine Decarboxylase—A 15-mL portion of YT (50 μg/mL ampicillin) in a 100-mL conical flask was inoculated with one of several strains of JM109 transformed with either pGEM-7Z14 or a partially deleted derivative. In some experiments 20 mM 2-methylalanine or other amino acid or 1 mg/mL IPTG was added to the growth medium. After growing overnight at 37° C. with shaking, the culture was cooled on ice, and the bacteria were harvested by centrifugation, resuspended in 2 mL MOPS buffer, sonicated 30 s, centrifuged (10,000× g), and 0.50 mL of the supernatant was assayed for decarboxylase activity. Protein concentrations were determined by dye binding (Read and Northcote, 1981).

Time Course of Dialkylglycine Decarboxylase Induction—An 800-mL portion of M9 containing 12 μg/mL tetracycline in a 6-L conical flask was inoculated with DH5α/pKBD6. The flask was shaken at 37° C. and the absorbance at 600 nm was measured periodically. At various times during cell growth aliquots containing 60. AU's (absorbance units) of cells were removed, stored on ice, concentrated by centrifugation, and resuspended in 1.0 mL MOPS buffer. Aliquots of 0.50 mL were assayed for dialkylglycine activity. After the first two samples were taken, an amino acid (2-methylalanine, R,S-isovaline, D-alanine, or L-alanine) was added to a final concentration of 8.0 mM and sampling was continued.

Materials—Plasmids pGEM7Z14 and the nested deletions pGEM7Z14/2b, and pGEM7Z14/6a are described supra (FIG. 1). The pBTac1 vector and alkaline phosphatase may be obtained commercially from Boehringer-Mannheim. Restriction enzymes, Taq polymerase, E. coli strain JM109, and mini-prep filters are available from Promega. DNA fragments were purified after most procedures using a Prep-A-Gene matrix that can be obtained from BioRad. The 1 kb dsDNA ladder was obtained from BRL, S-35 dATP from New England Nuclear, and Sequenase enzyme from USB. Cartridge-purified DNA primers can be synthesized using standard equipment and techniques, such as an Applied Biosystems Model 392 DNA synthesizer. Media were prepared as described in (Sambrook et al., 1989) with carbenicillin replacing ampicillin.

DNA Sequencing—Dideoxy sequencing was carried out on plasmid templates purified using the Promega "Magic Mini-Prep" filters, S-35 dATP, Sequenase enzyme, and custom primers. Stopped termination reactions were stored up to three days at about 20° C., then were heated at about 80° C. for about 2 min and about 3 μl aliquots were run on a 0.4 mm 5% polyacrylamide gel containing about 42% w/v urea. The running gel was kept at about 50° C. and a buffer gradient was used (Sheen et al., 1988). Other procedures were performed as described supra.

Sequence Analysis—DNA and protein sequences were analyzed using Genepro software that may be obtained from Riverside Scientific, Bainbridge Island, Wash. 98110.

Subcloning dgdR in pBTac1—The dgdR gene was subcloned into pBTac1 using DNA amplification (FIG. 11). The amplification template was a pGEM-7Zf(+)-derived plasmid with an inserted Pseudomonas DNA segment truncated by 249 bp at the end nearest the dgdR gene. This plasmid is also identified herein as pGEM7Z14/2b. One primer, JK-5-20 (5'-AGCTCTCCGGATCCAAGCTT3) [SEQ ID NO: 4], was complementary to vector sequences next to the insert and outside of the vector BamHi site. The other primer, JK12 (5'-CCACAGAATTCTATGCAAGG-TAGAAAGGGCGCT-3')[SEQ ID NO: 5], included an EcoRI site correctly spaced relative to the pBTac1 ribosome binding site and the first 15 nucleotides of dgdR. By way of example, typical conditions for amplication are 30 cycles of 95° C. for 2 minutes, 57° C. for 1 minute and 73° C. for 2 minutes, followed by incubation at 4° C. The 1049 bp amplified product was purified, cut with EcoRI and BamHI, and ligated to a vector that had been cut with the same enzymes and dephosphorylated with alkaline phosphatase (Kalvakolanu et al., 1991). Competent JM109 bacteria were prepared by the method of Nishimura et al. (1990) and transformed with the ligated DNA. The transformed cells were selected on LB agar containing 50 μg/mL carbenicillin. The structure of the resulting plasmid pJKDGDR1 was verified by restriction mapping and dideoxy sequencing.

Repressor Preparation—A 100 ml portion of LB medium containing about 50 μg/ml carbenicillin was inoculated with about a 2 ml overnight culture of JM109/pJKDGDR1 and was grown at about 37° C. to an OD600 of 1. IPTG was added to a final concentration of about 1 mM, the culture was shaken another 4 h, and then was pelleted by centrifugation at 4000 xg at about 4° C. The pellet was resuspended in 5 ml buffer (50 mM TrisHCl pH 7.9, 50 mM KCl), sonicated 3×0.5 min at about 0° C., and centrifuged for about 15 min at about 12,000 xg at about 4° C. Aliquots of the supernatant were used for gel shift assays and SDS-PAGE. Other aliquots were partially purified by selective precipitation with 1.0 M ammonium sulfate. Protein concentration was determined by the dye binding method of Read and Northcote (1981).

Figure 13:
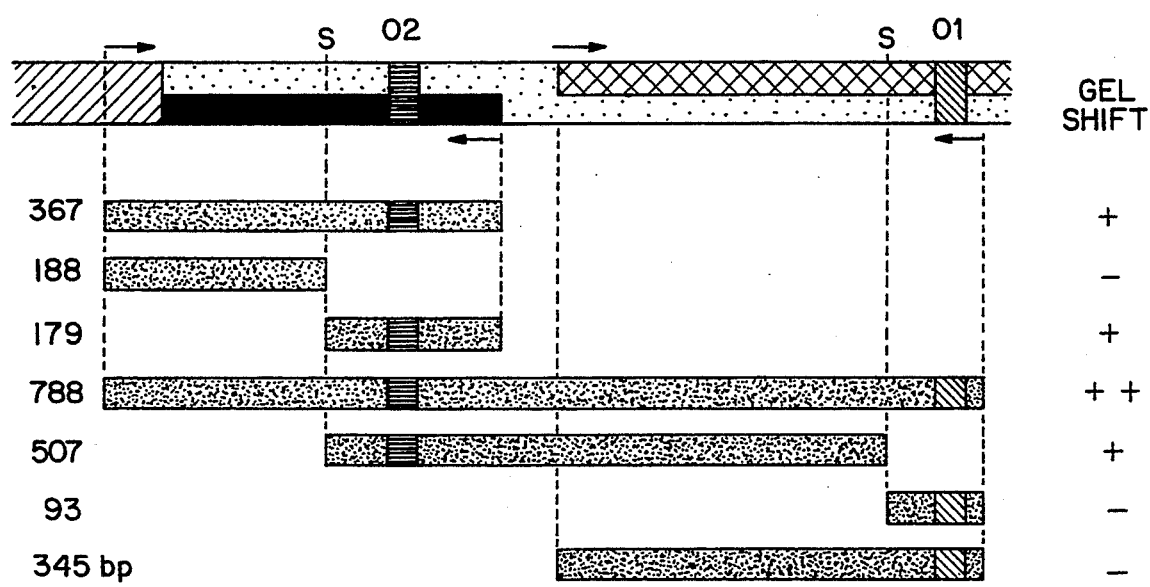
FIG. 13 depicts gel mobility shift results. The template used in amplification reactions is pGEM-7Z14/6a. The black region is the 5' end of dgdR gene; the light stippled region is P. cepacia DNA; the heavy stippled region is the 5' end of dgdA gene; the cross-hatched region is vector DNA. S is a SalI restriction site. Arrows are primers used in the amplification reactions. [−] indicates no shifted band, while [+] is one shifted band and [++] is two shifted bands.

DNA Fragments for Gel Shift Assays—DNA fragments were prepared by DNA amplification using pGEM7Z14/6a as a template (FIG. 13). This plasmid has 328 bp of the 5' end of the dgdR gene supra. The DNA fragments were synthesized using four primers in different combinations: JK5-20; JK12; JK7 (5'-TTGCCGCTTCGTTCGATT-3') [SEQ ID NO: 6], which is complementary to a 20-nucleotide sequence 355 bp into the dgdA gene; and JK5 (5'-ATGTCCCTGAACGACGATGC-3') [SEQ ID NO: 7] which, contains the first 20 nucleotides of the dgdA gene. DNA amplification reactions (about 50 μl total volume) contained about 200 μM dNTPs, 1 μM primer, 5 ng template, 1% formamide, 5 μl 10% Taq buffer (Promega), and 2 units Taq polymerase, all under a 60 μl layer of mineral oil. Twenty-five cycles with set point temperatures of 97° C. (1 min), 54° C. (0.5 min), and 73° C. (20 min) were run in a Coy TempCycler. PCR syntheses were scaled up when necessary by increasing the number of vials. SalI restriction fragments derived from these PCR products were matrix-purified.

Gel Shift Assays—A 10 μl assay mixture contained about 50 ng of DNA fragment, 1.0 μg of repressor extract (or 1.0 μg of extract from a JM109 strain containing a dgdA-pBTac1 recombinant), 10 mM TrisHCl pH 7.6, 5 mM sodium acetate, 2.5% glycerol, and 0.005% bovine serum albumin. The mixture was incubated 5 to 20 min at room temperature, about 3 μl of 50% sucrose/0.1% bromophenol blue was added, and the entire sample was analyzed by electrophoresis in a 1 mm 4% polyacrylamide gel containing about 50 him Tris, 380 mM glycine, 4 mM EDTA, and 2.5% glycerol. Some gels also contained about 20 mM 2-methylalanine. The gel was pre-electrophoresed at 90 V for about 30 min, run with the sample for about 90 min at about 4° C., stained for about 30 min in 1× TAE containing about 0.1 mg/l ethidium bromide, and finally was photographed under UV light.

Sequence of dqdR gene and Alignment With LysR Proteins—The dgdR sequence (SEQ ID NO: 10) and the sequence of its translation product (SEQ ID NO: 11) are shown in FIG. 4. The predicted 293-amino acid dgdR gene product has a MW of 31,955, with about 10% of the residues basic, 11% acidic, and 29% hydrophobic.

Alignment of the repressor sequence with several representative sequences of the LysR family was carried out using the "Multalin" program described in (Corpet, 1988). This alignment is shown in FIG. 12. The sequence homology is minimal near the carboxyl termini but increases near a predicted helix-turn-helix motif near the amino terminus (Henikoff et al., 1988). This alignment is consistent with our previous conclusion, based on the biological properties of a set of nested deletions from the 3' end of the dgdR gene, that the 5' end of dgdR codes for a DNA binding domain. There is no significant homology with the dialkylglycine decarboxylase sequence.

Expression of dgdR—Insertion of the dialkylglycine decarboxylase structural gene dgdA in pBTac1 (de Boer et al., 1985) produces high levels of gene product when induced with IPTG. pBTac1 comprises the hybrid tac promoter, a multiple cloning site next to an $E.$ $coli$ ribosome binding site, a downstream transcription termination sequence, and the ampicillin resistance gene. These results demonstrate that unusual codons do not prevent high level expression of $Pseudomonas$ gene products in $E.$ $coli.$ Consequently, the same strategy was adopted for over-expressing the dgdR gene product. A pBTac1-dgdR recombinant (pJKDGDR1) was constructed using PCR amplification to introduce restriction sites as indicated in FIG. 11. $E.$ $coli$ host JM109 transformed with pJKDGDR1 grew normally in LB medium containing about 80 μg/ml carbenicillin; however, growth was inhibited by micromolar levels of IPTG. 1 mM IPTG, which normally gives maximal expression from lac-related promoters, completely prevented growth of this strain. Growth was not restored by adding 20 mM 2-methylalanine. These results provided the first suggestion that the dgdR repressor may bind to a region within the dgdR gene as such binding would prevent plasmid replication and inhibit antibiotic resistance in the host.

Repressor—Repressor containing extracts were finally obtained by growing JM109/pJKDGDR1 cultures in LB/carbenicillin to reach stationary phase, then adding 1 mM IPTG. The dgdR gene product was detected in cell sonicate supernatants both by gel shift assay and SDS-PAGE. SDS-PAGE gels showed a new band at about 35 kDa that became more intense after IPTG induction. This band is ascribed to the dgdR repressor which migrates slower than expected for a 32 kDa protein. MetR, another member of the LysR family, also migrates somewhat slower that expected based on its gene sequence (Chu et al., 1985; Maxon et al., 1989).

Figure 14:
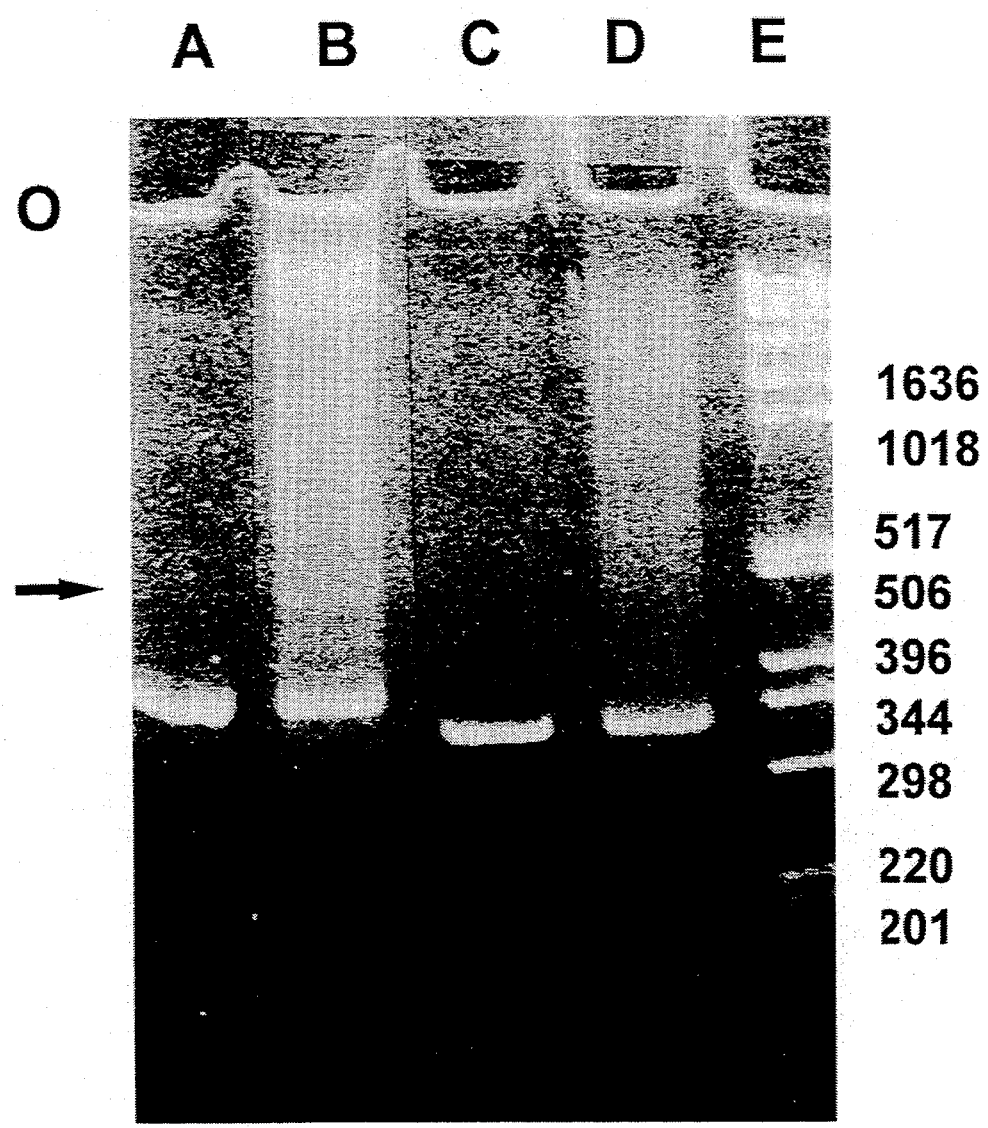
FIG. 14 depicts gel mobility shift assays for the 367 and 345 bp fragments. In lanes A and C, no protein is added; in lanes B and D, 1 μg of dgdR-containing extract is added. Lanes A and B, 50 ng 367 bp fragment (from dgdR gene and contains O2); lanes C and D, 50 ng 345 bp fragment (from dgdA gene and contains O1).

DNA Binding Assays—The dgdR repressor was detected by gel mobility shift assays using DNA fragments encompassing all or part of the 5' ends of the dgdA and/or dgdR genes (FIG. 13). The 367 bp PCR product contains the first 328 nucleotides of the dgdR gene plus 39 bp of unrelated vector DNA; the 345 bp PCR fragment includes the first 345 bp of the divergent dgdA gene; and the 788 bp fragment includes 39 bp from the vector, the first 328 bp of dgdR, the 78 bp intergenic region, and the first 345 nucleotides of dgdA. Addition of cell sonicate supernatant from IPTG-induced JM109/pJKDGDR1 cells to the 367 bp fragment followed by polyacrylamide electrophoresis showed a single slower-moving DNA band in addition to the original unshifted DNA band (FIG. 14) and addition of repressor extract to the 788 bp fragment showed two electrophoretically-related bands (FIG. 15 and 16). Control experiments verified that (i) the JM109/pJKDGDR1 extract did not shift the 345 bp PCR fragment that contains only O1 (FIG. 14) and (ii) Shifted bands were not observed when these fragments treated with a cell extract of $E.$ $coli$ JM109 carrying a pBTac1/dgdA recombinant plasmid.

Since 2-methylalanine derepresses expression of the dgdA gene in vivo, see supra, it should also reverse biologically-significant DNA binding by the dgdR gene product in the electrophoresis gel. Since 2-methylalanine is uncharged at neutral pH, 20 mM 2-methylalanine was included in a gel to test this hypothesis. No effect on repressor binding to the 367 bp fragment was observed. Nor was there any effect on the faster of the two shifted bands formed by repressor binding to the 788 bp fragment, but there was a significant increase in electrophoretic mobility of the slower of these two shifted bands (FIG. 16).

Further information about the location of binding sites was sought by cutting the original fragments with SalI prior to mixing with the repressor preparation (FIG. 13). There is a SalI site at position 166 of dgdR, which cuts the 367 bp PCR fragment into two fragments 188 and 179 bp long. There is another SalI site at position 261 of dgdA; thus SalI cuts the 788-bp fragment into three fragments, 179, 507 and 93 bp long. The repressor preparation shifted only the 179 bp fragment.

Identification of Operator—Candidate repressor binding sites O1 and O2, (FIG. 17) were located by dot matrix analysis of the sequence of the 788 bp PCR fragment in which the sequence of one strand was aligned with its reverse complement and sequence identities within a 12-nucleotide window were determined. No sequences with dyad symmetry were found in the intergenic region, but two regions with strong dyad symmetry were found in the adjacent genes: O1, 335 bp into the decarboxylase gene, and O2, 76 bp into the repressor gene.

Interpretation of Gel Shift Data—The results suggest that the repressor binds to two of the operator sites, O1 and O2, predicted by sequence analysis. O1 and O2 are dyadsymmetric, thus the protein binding unit is probably dimeric, as with other procaryotic DNA binding proteins. Single shifted DNA bands were observed from those fragments containing O2, namely 179 bp, 367 bp, and 507 bp fragments (FIGS. 15 and 16). A comparison of the migration distances of complexed and uncomplexed fragments using the method of Bading (Bading 1988) gives an estimate of approximately 60 kDa for the attached protein, as expected for two 32 kDa dgdR subunits. In contrast, neither the 93 bp or the 355 bp fragments, which contain only O1, formed a shifted band with the repressor extract; thus under these condition the repressor does not bind to O1 by itself. When both O1 and O2 are present on a fragment, such as the 788 bp fragment, two shifted bands are formed. The faster shifted band of these two is probably a DNA-dimer complex with O2, since the degree of retardation is about the same observed for the fragments containing O2 only. The slower shifted band shows increased mobility when electrophoresed in the presence of 20 mM 2-methylalanine, the natural de-repressor of dgdA gene expression (FIG. 16). Consequently, the slow band could have a looped structure formed by a tetrameric (or larger) repressor complex bound to both O1 and O2, and that 2-methylalanine releases O1 from the tetramer with a concomitant increase in flexibility and therefore the mobility of the DNA-protein complex. Mobility analysis of the slower 788 bp repressor complex by the Bading method (1988) suggests attachment of a very large protein, or what is more likely, a protein tetramer with bent or looped DNA. Such structures are known to reduce DNA electrophoretic mobility compared to linear DNA-protein complexes (Oehler et al., 1990). The gel shift data excludes the possibility that two independent repressor dimers bind O1 and O2, since no binding to DNA fragments containing only O1 was observed. Therefore O1 binding by the repressor must be cooperative with O2 binding.

Relationship of dgdR to other LysR sequences—One aspect of this invention is that an open reading frame associated with the negative control of 2-methylalanine metabolism encodes a member of the large LysR family of DNA binding proteins. There is convincing homology within the whole LysR family. Interestingly most of the LysR proteins act as transcriptional activators; only the dgdR, calM (Neidle et al., 1989), and ampR (Honore et al., 1986) gene products seem to act as classic repressors. However, there is no greater sequence homology between these latter three sequences than between dgdR and other members of this family.

Properties of dgdR and its role in controlling dgdA expression—This invention also relates to two operator sites, one in the dgdR gene and another in the dgdA gene that bind the repressor. The binding sites were identified by presenting a variety of DNA fragments from the 5' ends of the two genes to the repressor in gel shift assays. Fragments bearing only O2 (the site within dgdR) are readily shifted by repressor binding. Fragments bearing only O1 (the site within dgdA) are not shifted at all. But the 788 bp fragment which contains both O1 and O2 gave two shifted bands. One band has a mobility corresponding to attachment of a repressor dimer to the fragment; the other, much slower, band probably is due to attachment of a repressor tetramer that bridges O1 and O2.

An additional observation was that 20 mM 2-methylalanine apparently releases O1, but not O2, binding. This was observed in gel shift assays, but also is consistent with our finding that addition of 20 mM 2-methylalanine to IPTG containing cultures of JM109/pJKDGDR1 still did not allow normal growth for this strain, as the repressor continued to bind O2 within the dgdR gene on the plasmid. However, such binding would be useful under natural conditions to prevent dgdR expression and possibly to provide positive control of dgdA expression through an interaction with RNA polymerase. Such positive control is supported by the documented positive control function of LysR proteins, and the fact that the natural host for this genetic system is *P. cepacia,* whose RNA polymerase is similar but not identical to that of *E. coli.*

Following are the citations of publications cited in the foregoing text.

Aaslestad, H. G., and Larson, A. D. (1964) *J. Bacteriol.* 91, 1296–1303.

Aaslestad, H. G., Bouis, Jr., P. J., Phillips, A. T., and Larson, A. D. (1968) in *Pyridoxal Catalysis: Enzymes and Model Systems* (Snell, E. E., Braunstein, A. E., Severin, E. S., and Torchinsky, Yu M., eds) pp. 479–490, Wiley Interscience, New York.

Bading, H. (1988) *Nucleic Acids Res.* 16, 5241–5248.

Bailey, G. B., and Dempsey, W. B. (1967) *Biochemistry* 6, 1526–1533.

Bailey, G. B., Chotamangsa, O. and Vuttivej, K. (1970) *Biochemistry* 9, 3243–3248.

Baker, C. G., Fu, S.-C. J., Birnbaum, S. M., Sober, H. A., and Greenstein, J. P. (1952) *J. Am. Chem. Soc.* 74, 4701–4702.

Baurick, K. B. (1987) M. S. Thesis, University of Alaska, Fairbanks.

Bibb, M. J., Findlay, P. R., and Johnson, M. W. (1984) *Gene (Amst.)* 30, 157–166.

Borisov, V. V., Borisova, S. N., Sofenov, N. L., and Wainshtein, B. K. (1980) *Nature* 284, 189–191.

Bosch, R., Bruckner, G., Jung, G., and Winter, W. (1982) *Tetrahedron* 38, 3579–3583.

Bruckner, H., and Pryzbylski, M. (1984) *J. Chromatog* 296, 263–275.

Bruckner, H., Nicholson, G. J., Jung, G., Kruse, K., and Konig, W. A. (1980) *Chromatographia* 13, 209–214.

Bulmer, M. (1988) *J. Theoret. Biol.* 133, 67–71.

Chu, J., Shoeman, R., Hart, J., Coleman, T., Mazaitis, A., Cornish-Bowden, A. (1979) *J. Theoret. Biol.* 76, 369–386.

Corpet (1988) *Nucleic Acids Res* 16, 10881–10890.

Degols, G. (1987) *Eur. J. Biochem.* 169, 193–200.

Dinwoodie, R. C., and Boeker, E. A. (1979) *Anal. Biochem.* 96, 24–38.

Doonan, S., Doonan, H. J., Hanford, R., Bernon, C. A., Walker, J. M., Airoldi, L., Bossa, F., Barra, D., Carloni, M., Fasella, P., and Riva, F. (1975) *Biochem. J.* 149, 497–506.

Engel, M. H., Macko S. A., and Silfer, J. A. (1990) *Nature* 348, 47–49.

Fischer, E. H., Kent, A. B., Snyder, E. R., and Krebs, E. G. (1958) *J. Am. Chem. Soc.* 80, 2906–2907.

Ford, G. C., Eichele, G., and Jansonius, J. N. (1980) *Proc. Natl. Acad. Sci. U.S.A.* 77, 2559–2563.

Fotheringham, I. G., Dacey, S. A., Taylor, P. P., Smith, T. J., Hunter, M. G., Finlay, M. E., Primrose, S. B., Parker, D. M., and Edwards, R. M. (1986) *Biochem. J.* 234, 593–604.

Golub, E. I. (1988) *Nucleic Acids Res.* 16, 1641.

Graf-Houser, U., Wilson, K. J., and Christen, P. (1983) *J. Biol. Chem.* 258, 8813–8826.

Greenstein, J. P., and Winitz, M. (1961) *Chemistry of the Amino Acids,* Vol. 3, p. 2565, Wiley Interscience, New York.

H. A. de Boer et al. (1983) *Proc. Nat. Acad. Sci.* (U.S.A.) 80, 21.

Hayashi, H., Tanase, S., and Snell, E. E. (1986) *J. Biol. Chem.* 261, 11003–11009.

Henikoff, S. (1984) *Gene (Amst.)* 28, 351–359.

Henikoff, S., Haughn, G. W., Calvo, J. M., and Wallace, J. C. (1988) *Proc. Nat. Acad. Sci.* (U.S.A.) 85, 6602–6606.

Henikoff, S., and Wallace, J. C. (1988) *Nucleic Acids Res.* 16, 6191–6204.

Honore, N., Nicolas, M. H., and Cole, S. T. (1986) *EMBO J.* 5, 3709–3714.

Holmes, D. S., and Quigley, M. (1981) *Anal. Biochem.* 114, 193–197.

Honma, M., Ikeda, M., and Shimomura, T. (1972) *Agric. Biol. Chem. Tokyo* 36, 1661–1666.

Inoue, K., Kuramitsu, S., Aki, K., Watanabe, Y., Takagi, T., Nishigai, A., and Kagamiyama, H. (1988) *J. Biochem. (Tokyo)* 104, 777–784.

Jansonius, J. N., Eichele, G., Ford, G. C., Picot, D., Thaller, C., and Vincent, M. G. (1985) in *Transaminases* (Christen, P., and Metzler, D. E., eds) pp. 109–137, Wiley Interscience, New York.

Jones, W. M., Sealoni, A., Bossa, F., Popowicz, A. M., Schneewind, O., and Manning, J. M. (1991) *Proc. Nat. Acad. Sci.* (U.S.A.) 88, 2194–2198.

Kagamiyma, H., Sakakibara, R., Tanase, S., Morino, Y., and Wada, H. (1980) *J. Biol. Chem.* 255, 6153–6159.

Kalvakolanu, D. V. R., and Livingston III, W. H. Biotechniques 10, 176–177.

Kelker, N., Brot, N., and Neisbach, H. (1985) *Arch. Biochem. Biophys.* 239, 467–474.

Keller, J. W., Baurick, K. B., Rutt, G. C., O'Malley, M. V., Sonafrank, N. L., Reynolds, R. A., Ebbeson, L. O. E., and Vaydos, F. F. (1990) *J. Biol. Chem.* 265, 5531–5539.

Keller, J. W., and Hamilton, B. J. (1986) *Tetrahedron Lett.* 27, 1249–50.

Keller, J. W., and O'Leary, M. H. (1979) *Biochem. Biophys. Res. Commun.* 90, 1104–1110.

Koga, P. G., and Cross, R. L. (1982) *Biochim. Biophys. Acta* 679, 269–278.

Kraft, R., Tardiff, J., Krauter, K. S., and Leinwand, L. A. (1988) *Biotechniques* 6, 544–546.

Kvenvolden, K. A., Lawless, J. G., and Ponnamperuma, C. (1971) *Proc. Natl. Acad. Sci. U.S.A.* 68, 486–490.

Lamartiniere, C. A., Itoh, H., and Dempsey, W. B. (1971) *Biochemistry* 10, 4783–4788.

Maniatis, T., Fritsch, E. F., and Sambrook, J. (1982) *Molecular Cloning: A Laboratory Manual,* Cold Spring Harbor Laboratory, Cold Spring Harbor, N.Y.

Maxon, M. E., Rodfield, B., Cai, X.-Y., Shoeman, R., Fujita, K., Fisher, W., Stauffer, G., Weissbach, H., and Brot, N. (1989) *Proc. Nat. Acad. Sci.* (U.S.A.) 86, 85–89.

Min, T. M., Kim, M. H., and Lee, D. S. (1988) *Nucleic Acids Res.* 16, 5075–5088.

Mitchell, G. A., Looney, J. E., Brody, L. C., Steel, G., Suchanek, M., Engelhardt, J. F., Willard, H. F., and Valle, D. (1988) *J. Biol. Chem.* 263, 14288–14295.

Mueckler, M. M., and Pitot, H. C. (1985) *J. Biol. Chem.* 260, 12993–12997.

Needleman, S. B., and Wunsch, C. D. (1970) *J. Mol. Biol.* 48, 443–453.

Neidle, E. L., Hartnett, C., and Ornston, L. N. (1989) *J. Bacteriol.* 171, 5410–5421.

Nishimura, A., Morita, M., Nishimura, Y., and Sugino, Y. (1990) *Nucleic Acids Res.* 18, 6169.

Oda, T., Miyajima, H., Suzuki, Y., and Ichiyama, A. (1987) *Eur. J. Biochem.* 168, 537–542.

Oehler, S., Eismann, E. R., Kramer, H., and Muller-Hill, B. 1990) *EMBO J.,* 9, 973–79.

Platt, T. (1986) *Annu. Rev. Biochem.* 55, 339–372.

Raibaud, O., and Goldberg, M. E. (1974) *FEBS Lett.* 40, 41–44.

Reed, S. M., and Northcote, P. H. (1981) *Anal. Biochem.* 116, 53–64.

Sambrook, J., Fritsch, E. F., and Maniatis, T. (1989) *Molecular Cloning A Laboratory Manual, Second Edition,* Cold Spring Harbor Laboratory Press, Cold Spring Harbor, N.Y.

Sanger, F., Nicklen, S., and Coulson, A. R. (1977) *Proc. Natl. Acad. Sci. U.S.A.* 74, 5463–5467.

Sato, S., Honma, M., and Shimomura, T. (1978) *Agric. Biol. Chem. Tokyo* 42, 2341–2346.

Schmitt, H., and Jung, G. (1985) *Liebig's Ann. Chem.* 1985, 321–344.

Sheen, J. Y., and Seed, B. (1988) *Biotechniques* 6, 46–48.

Shin, M., Sakihama, N., Oshino, R., and Sasaki, H. (1984) *Anal. Biochem.* 138, 259–261.

Simmaco, M., John, R. A., Barra, D., and Bossa, F. (1986) *FEBS Lett.* 199, 39–42.

Sober, H.A. (1968) *Handbook of Biochemistry,* p. H-31, Chemical Rubber Co., Cleveland.

Stormo, G. D., Schneider, T. D., and Gold, L. M. (1982) *Nucleic Acids Res.* 10, 2971–2996.

Sukhareva, B. (1986) *Vitamin B-6. Chemical, Biochemical, and Medical Aspects* (Dolphin, D., Poulson, R., and Avramovic, O., eds) Part B, pp. 337–343, Wiley Interscience, New York.

Tahara, S., Honma, M., and Shimomura, T. (1969) *Mem. Fac. Agric. Hokkaido Univ.* 7, 12–18.

Tamura, J. K., and Rakov, R. D. (1986) *J. Biol. Chem.* 261, 4126–4133.

Tanase, S., Kojima, H., and Morino, Y. (1979) *Biochemistry* 18, 3002–3007.

Vaaler, G. L., and Snell, E. E. (1989) *Biochemistry* 28, 7306–7313.

van del Zel, A., Lam, H.-M., and Winkler, M. W. (1989) *Nucleic Acids Res.* 17, 8379.

Wilbur, W. J., and Lipman, D. J. (1983) *Proc. Natl. Acad. Sci. U.S.A.* 80, 726–730.

Yanisch-Perron, C., Viera, J., and Measing, J. (1985) *Gene (Amst.)* 33, 103–119.

Zhao, M., and Bada, J. L. (1989) *Nature* 339, 463–465.

---

What is claimed is:

1. A purified repressor protein consisting essentially of the amino acid sequence shown in SEQ ID NO: 11.

2. The purified repressor protein as claimed in claim 1, wherein said repressor protein is in oligomeric form.

3. The purified repressor protein as claimed in claim 2, wherein said repressor protein is in dimeric form.

4. A recombinant vector, wherein said vector comprises:
    a) a nucleotide sequence encoding 2,2-dialkylglycine decarboxylase repressor protein;

b) a nucleotide sequence coding for a ribosome binding site;
c) a promoter; and
d) a restriction endonuclease cleavage site for insertion of a foreign gene downstream from said nucleotide sequence coding for a ribosome binding site.

5. The recombinant vector as claimed in claim 4, wherein said promoter is selected from the group consisting of 2,2-dialkylglycine decarboxylase promoter and lac promoter.

6. The recombinant vector as claimed in claim 5, wherein said promoter and said nucleotide sequence encoding 2,2-dialkylglycine decarboxylase repressor protein are arranged for read-through transcription by a polymerase.

7. A recombinant vector, wherein said vector comprises:
a) operators O1 and O2;
b) a nucleotide sequence coding for a ribosome binding site downstream of said operators;
c) a first promoter situated between operators O1 and O2; and
d) a restriction endonuclease cleavage site for insertion of a foreign gene downstream of said operators;
wherein:
1) O1 and O2 are able to cooperativley bind 2,2-dialkylglycine decarboxylase repressor protein to prevent binding of polymerase to said first promoter; and
2) said first promoter and said restriction endonuclease cleavage site are positioned relative to each other to provide an operable linkage between said first promoter and a foreign gene to be inserted at said restriction site.

8. The recombinant vector as claimed in claim 7, wherein said expression vector further comprises the dgdR gene upstream of said first promoter, wherein said dgdR gene is operatively linked to a second promoter.

9. The recombinant vector as claimed in claim 8, wherein said first promoter is the 2,2-dialkylglycine decarboxylase promoter.

10. The recombinant vector as claimed in claim 8, wherein said first promoter is selected from the group consisting of lac, trp, and tac promoters.

11. A recombinant vector, wherein said vector comprises:
a) operators O1 and O2;
b) a nucleotide sequence coding for a ribosome binding site downstream of said operators;
c) a first promoter situated between operators O1 and O2; and
d) a heterologous structural gene downstream of said operators;
wherein:
1) O1 and O2 are able to cooperatively bind 2,2-dialkylglycine decarboxylase repressor protein to prevent binding of polymerase to said first promoter; and
2) said first promoter and said heterologous gene are operably linked for expression of said gene.

12. The recombinant vector as claimed in claim 11, wherein said expression vector further comprises the dgdR gene located upstream of said first promoter, wherein said dgdR gene is operatively linked to a second promoter.

13. The recombinant vector as claimed in claim 11, wherein said first promoter is the 2,2-dialkylglycine decarboxylase promoter.

14. The recombinant vector as claimed in claim 11, wherein said first promoter is selected from the group consisting of lac, trp, and tac promoters.

15. A method of providing a heterologous protein in a host cell, wherein said process comprises:
a) providing a host cell transformed with a recombinant vector as claimed in claim 11 and containing 2,2-dialkylglycine decarboxylase repressor protein of *Pseudomonas cepacia;*
b) dissociating repressor protein from operator O1 by adding an inducer selected from the group consisting of S-isovaline, 2-methylalanine, L-2-aminobutanoic acid, and 1-aminocyclopentanecarboxylic acid; and
c) expressing the heterologous structural gene.

16. The method of producing a heterologous protein as claimed in claim 15, wherein repressor protein remains bound to operator O2 following dissociation of repressor protein from operator O1.

17. The method of producing a heterologous protein as claimed in claim 15, wherein said host cell is a unicellular eukaryote and said first promoter binds RNA polymerase of said unicellular eukaryote.

18. The method of producing a heterologous protein as claimed in claim 17, wherein said eukaryotic cell is yeast.

19. The method of producing a heterologous protein as claimed in claim 15, wherein said host cell is prokaryotic cell and said first promoter binds RNA polymerase of said prokaryotic cell.

20. The method of producing a heterologous protein as claimed in claim 19, wherein said host cell is *E. coli.*

21. A nucleotide sequence coding for a repressor protein for regulating gene expression, wherein:
(A) the nucleotide sequence comprises about 687 bp nucleotide region on the strand complimentary to the strand containing the 2,2-dialkylglycine decarboxylase structural gene shown in SEQ ID NO: 8;
(B) the nucleotide sequence begins about 81 bp upstream from the 2,2-dialkylglycine decarboxylase structural gene shown in SEQ ID NO: 8; and
(C) the nucleotide sequence codes for said repressor protein, which comprises about 229 amino acids.

22. A nucleotide sequence as claimed in claim 21, wherein the nucleotide sequence consists of nucleotides coding for the amino acid sequence of the repressor protein shown in SEQ ID NO: 11.

23. A recombinant expression vector containing the nucleotide sequence as claimed in claim 21, wherein said recombinant expression vector is pKBD6.

24. A recombinant expression vector containing the nucleotide sequence as claimed in claim 21, wherein said recombinant expression vector is pUC19C7.

25. A recombinant expression vector containing the nucleotide sequence as claimed in claim 21, wherein said recombinant expression vector is pGEM-7Z14.

26. A recombinant expression vector, wherein said recombinant expression vector is pGEM-7Z14/3e.

27. An *E. coli* cell transformed or transfected with the recombinant expression vector claimed in claim 23.

28. An *E. coli* cell transformed or transfected with the recombinant expression vector claimed in claim 24.

29. An *E. coli* cell transformed or transfected with the recombinant expression vector claimed in claim 25.

30. An *E. coli* cell transformed or transfected with the recombinant expression vector claimed in claim 26.

31. A process for obtaining *Pseudomonas cepacia* 2,2-dialkylglycine decarboxylase, which comprises:
- (A) providing a biomass comprised of *E. coli* cells as claimed in claim 27; and
- (B) culturing said *E. coli* cells in the presence of a transcriptional inducing agent selected from the group consisting of S-isovaline and 2-methylalanine;
- wherein said agent is employed in said biomass in an amount sufficient to induce transcription of said *Pseudomonas cepacia* 2,2-dialkylglycine decarboxylase gene.

32. A process for obtaining *Pseudomonas cepacia* 2,2-dialkylglycine decarboxylase, which comprises:
- (A) providing a biomass comprises of *E. coli* cells as claimed in claim 28; and
- (B) culturing said *E. coli* cells in the presence of a transcriptional inducing agent selected from the group consisting of S-isovaline and 2-methylalanine;
- wherein said agent is employed in said biomass in an amount sufficient to induce transcription of said *Pseudomonas cepacia* 2,2-dialkylglycine decarboxylase gene.

33. A process for obtaining *Pseudomonas cepacia* 2,2-dialkylglycine decarboxylase, which comprises:
- (A) providing a biomass comprised of *E. coli* cells as claimed in claim 28; and
- (B) culturing said *E. coli* cells in the presence of IPTG;
- wherein IPTG is employed in said biomass in an amount sufficient to induce transcription of said *Pseudomonas cepacia* 2,2-dialkylglycine decarboxylase gene.

34. A process for obtaining *Pseudomonas cepacia* 2,2-dialkylglycine decarboxylase, which comprises:
- (A) providing a biomass comprised of *E. coli* cells as claimed in claim 28;
- (B) culturing said *E. coli* cells in the presence of a transcriptional inducing agent selected from the group consisting of S-isovaline, 2-methylalanine, L-2-aminobutanoic acid, or 1-aminocyclopentanecarboxylic acid; and
- (C) culturing said *E. coli* cells in the presence of IPTG;
- wherein said agent and said IPTG are employed in said biomass in an amount sufficient to induce transcription of said *Pseudomonas cepacia* 2,2-dialkylglycine decarboxylase gene.

35. A process for obtaining *Pseudomonas cepacia* 2,2-dialkylglycine decarboxylase, which comprises:
- (A) providing a biomass comprised of *E. coli* cells as claimed in claim 29; and
- (B) culturing said *E. coli* cells in the presence of a transcriptional inducing agent selected from the group consisting of S-isovaline and 2-methylalanine;
- wherein said agent is employed in said biomass in an amount sufficient to induce transcription of said *Pseudomonas cepacia* 2,2-dialkylglycine decarboxylase gene.

36. A process for obtaining *Pseudomonas cepacia* 2,2-dialkylglycine decarboxylase, which comprises:
- (A) providing a biomass comprised of *E. coli* cells as claimed in claim 29; and
- (B) culturing said *E. coli* cells in the presence of IPTG;
- wherein IPTG is employed in said biomass in an amount sufficient to induce transcription of said *Pseudomonas cepacia* 2,2-dialkylglycine decarboxylase gene.

37. A process for obtaining *Pseudomonas cepacia* 2,2-dialkylglycine decarboxylase, which comprises:
- (A) providing a biomass comprised of *E. coli* cells as claimed in claim 29;
- (B) culturing said *E. coli* cells in the presence of a transcriptional inducing agent selected from the group consisting of S-isovaline, 2-methylalanine, L-2-aminobutanoic acid, or 1-aminocyclopentanecarboxylic acid; and
- (C) culturing said *E. coli* cells in the presence of IPTG;
- wherein said agent and said IPTG are employed in said biomass in an amount sufficient to induce transcription of said *Pseudomonas cepacia* 2,2-dialkylglycine decarboxylase gene.

38. A process for obtaining *Pseudomonas cepacia* 2,2-dialkylglycine decarboxylase, which comprises:
- (A) providing a biomass comprised of *E. coli* cells as claimed in claim 30; and
- (B) culturing said *E. coli* cells in the presence of a transcriptional inducing agent selected from the group consisting of S-isovaline, 2-methylananine, L-2-aminobutanoic acid, or 1-aminocyclopentanecarboxylic acid;
- wherein said agent is employed in said biomass in an amount sufficient to induce transcription of said *Pseudomonas cepacia* 2,2-dialkylglycine decarboxylase gene.

39. A process for obtaining *Pseudomonas cepacia* 2,2-dialkylglycine decarboxylase, which comprises:
- (A) providing a biomass comprised of *E. coli* cells as claimed in claim 30; and
- (B) culturing said *E. coli* cells in the presence of IPTG;
- wherein IPTG is employed in said biomass in an amount sufficient to induce transcription of said *Pseudomonas cepacia* 2,2-dialkylglycine decarboxylase gene.

40. A process for obtaining *Pseudomonas cepacia* 2,2-dialkylglycine decarboxylase, which comprises:
- (A) providing a biomass comprised of *E. coli* cells as claimed in claim 30;
- (B) culturing said *E. coli* cells in the presence of a transcriptional inducing agent selected from the group consisting of S-isovaline, 2-methylalanine, L-2-aminobutanoic acid, or 1-aminocyclopentanecarboxylic acid; and
- (C) culturing said *E. coli* cells in the presence of IPTG;
- wherein said agent and said IPTG are employed in said biomass in an amount sufficient to induce transcription of said *Pseudomonas cepacia* 2,2-dialkylglycine decarboxylase gene.

* * * * *

UNITED STATES PATENT AND TRADEMARK OFFICE
CERTIFICATE OF CORRECTION

PATENT NO.: 5,356,796

DATED: October 18, 1994

INVENTOR: John W. KELLER

It is certified that an error appears in the above-identified patent and that said Letters Patent is hereby corrected as shown below:

Column 1, line 1, before the text, insert the following paragraph:

This invention was made with government support under Grant No. DMB-8704139 of the National Science Foundation. The government has certain rights in the invention.

Signed and Sealed this

Seventeenth Day of December, 1996

BRUCE LEHMAN

*Attest:*

*Attesting Officer*  *Commissioner of Patents and Trademarks*